(12) United States Patent
Sumathy et al.

(10) Patent No.: US 11,406,698 B2
(45) Date of Patent: *Aug. 9, 2022

(54) VACCINE COMPOSITIONS

(71) Applicant: Bharat Biotech International Limited, Hyderbad (IN)

(72) Inventors: Kandaswamy Sumathy, Hyderbad (IN); Krishna Murthy Ella, Hyderbad (IN)

(73) Assignee: Bharat Biotech International Limited, Hyderabad (IN)

( * ) Notice: Subject to any disclaimer, the term of this patent is extended or adjusted under 35 U.S.C. 154(b) by 0 days.

This patent is subject to a terminal disclaimer.

(21) Appl. No.: 16/812,316

(22) Filed: Mar. 8, 2020

(65) Prior Publication Data
US 2021/0187093 A1    Jun. 24, 2021

Related U.S. Application Data

(63) Continuation of application No. 15/212,804, filed on Jul. 18, 2016, now Pat. No. 10,588,956.

(30) Foreign Application Priority Data

Jul. 16, 2015 (IN) ............................ 3652/CHE/2015

(51) Int. Cl.
| | |
|---|---|
| *A61K 39/12* | (2006.01) |
| *A61K 47/18* | (2017.01) |
| *A61K 47/42* | (2017.01) |
| *A61K 47/02* | (2006.01) |
| *C07K 16/10* | (2006.01) |
| *A61K 47/26* | (2006.01) |
| *A61K 9/00* | (2006.01) |
| *A61K 39/00* | (2006.01) |

(52) U.S. Cl.
CPC ............ *A61K 39/12* (2013.01); *A61K 9/0019* (2013.01); *A61K 47/02* (2013.01); *A61K 47/183* (2013.01); *A61K 47/26* (2013.01); *A61K 47/42* (2013.01); *C07K 16/1081* (2013.01); *A61K 2039/5252* (2013.01); *A61K 2039/5555* (2013.01); *A61K 2039/55505* (2013.01); *A61K 2039/55511* (2013.01); *A61K 2039/55561* (2013.01); *A61K 2039/55566* (2013.01); *A61K 2039/55572* (2013.01); *A61K 2039/55583* (2013.01); *A61K 2039/58* (2013.01); *A61K 2039/70* (2013.01); *C12N 2710/14143* (2013.01); *C12N 2770/24134* (2013.01); *C12N 2770/24151* (2013.01); *C12N 2770/36134* (2013.01); *Y02A 50/30* (2018.01)

(58) Field of Classification Search
CPC ...... A61K 39/12; A61K 9/0019; A61K 47/02; A61K 47/183; A61K 47/26; A61K 47/42; A61K 2039/5252; A61K 2039/55505; A61K 2039/55511; A61K 2039/5555; A61K 2039/55561; A61K 2039/55566; A61K 2039/55572; A61K 2039/55583; A61K 2039/58; A61K 2039/70; A61K 9/08; A61K 39/42; C07K 16/1081; C12N 2710/14143; C12N 2770/24134; C12N 2770/24151; C12N 2770/36134; C12N 7/00; Y02A 50/30; A61P 31/12; A61P 31/14; A61P 37/04

See application file for complete search history.

(56) References Cited

U.S. PATENT DOCUMENTS

| | | | |
|---|---|---|---|
| 2011/0236421 A1 | 9/2011 | Brown | A61K 39/12 424/218.1 |
| 2017/0340724 A1* | 11/2017 | Ciaramella | A61K 39/12 |
| 2020/0397887 A1* | 12/2020 | Galarza | C07K 14/005 |

FOREIGN PATENT DOCUMENTS

| | | | | |
|---|---|---|---|---|
| WO | WO-2012172574 A1 | | 12/2012 | ............ A61K 39/12 |
| WO | WO-2017109223 A1 | * | 6/2017 | ............... C12N 7/00 |

OTHER PUBLICATIONS

Kudchodkar SB, Choi H, Reuschel EL, Esquivel R, Jin-Ah Kwon J, Jeong M, Maslow JN, Reed CC, et. al. Rapid response to an emerging infectious disease—Lessons learned from development of a synthetic DNA vaccine targeting Zika virus. Microbes Infect. Dec. 2018;20(11-12):676-684. Epub Mar. 17, 2018. (Year: 2018).*

Ioos S, Mallet HP, Leparc Goffart I, Gauthier V, Cardoso T, Herida M. Current Zika virus epidemiology and recent epidemics. Med Mal Infect. Jul. 2014;44(7):302-7. Epub Jul. 4, 2014. (Year: 2014).*

Hamel R, Dejarnac O, Wichit S, Ekchariyawat P, Neyret A, Luplertlop N, Perera-Lecoin M, Surasombatpattana P, Talignani L, Thomas F, Cao-Lormeau VM, Choumet V, Briant L, Després P, et. al. Biology of Zika Virus Infection in Human Skin Cells. J Virol. Sep. 2015;89(17):8880-96. Epub Jun. 17, 2015. (Year: 2015).*

Servin-Blanco R, Zamora-Alvarado R, Gevorkian G, Manoutcharian K. Antigenic variability: Obstacles on the road to vaccines against traditionally difficult targets. HumVaccin Immunother. Oct. 2, 2016;12(10):2640-2648. Epub Jun. 13, 2016. (Year: 2016).*

(Continued)

*Primary Examiner* — Rachel B Gill
(74) *Attorney, Agent, or Firm* — Remenick PLLC

(57) ABSTRACT

The present disclosure provides vaccine compositions for prophylaxis and treatment of Zika virus infections comprising Zika virus antigens in immunogenic compositions, and in combination of Zika antigens with one or more arbovirus antigens such as Chikungunya virus and Japanese encephalitis virus antigens, methods of preparation and production of such compositions for use as vaccines for eliciting immune response in mammals against the above mentioned pathogens.

35 Claims, 12 Drawing Sheets

Specification includes a Sequence Listing.

(56) References Cited

OTHER PUBLICATIONS

Lowe I, Southern J. The antimicrobial activity of phenoxyethanol in vaccines. Lett Appl Microbiol. Feb. 1994;18(2):115-6.

Tripp RA, Ross TM. Development of a Zika vaccine. Expert Rev Vaccines. Sep. 2016;15(9):1083-5. Epub Jun. 6, 2016.

Shawan MMAK, Al Mahmud H, Hasan M, Parvin A, Rahman N, Rahman SMB. In Silico Modeling and Immunoinformatics Probing Disclose the Epitope Based PeptideVaccine Against Zika Virus Envelope Glycoprotein. Indian J Pharm Biol Res. 2014; 2(4): 44-57. Available online Dec. 31, 2014.

Kuno G, et. al. Zika virus strain MR 766, complete genome. GenBank: AY632535.2. Dep. May 21, 2004, Updated Nov. 23, 2010.

\* cited by examiner

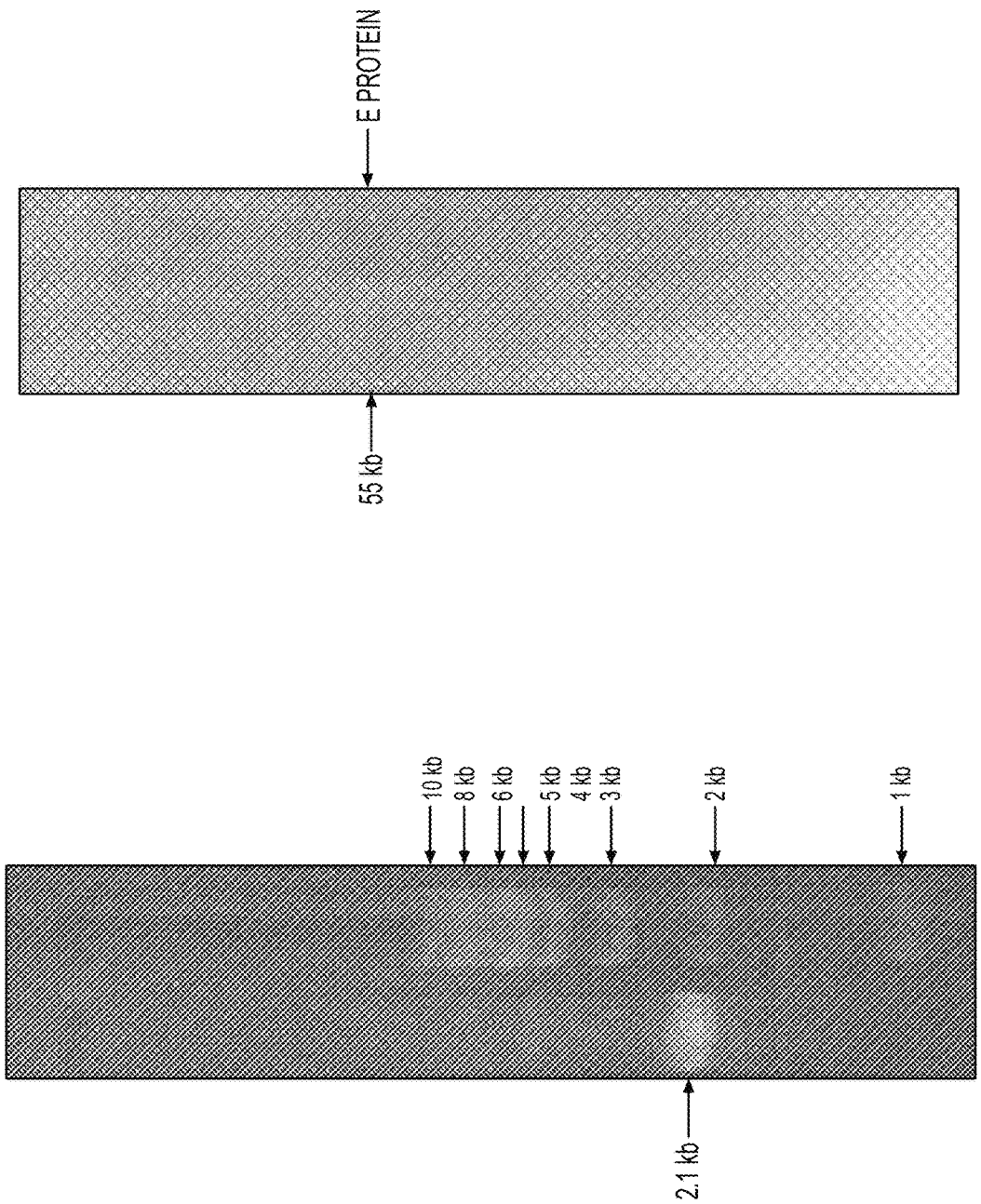

VACCINE COMPOSITIONS

CROSS REFERENCE

This Application is a Continuation of U.S. application Ser. No. 15/212,804 filed Jul. 18, 2016, which issued as U.S. Pat. No. 10,588,956 on Mar. 17, 2020, and claims priority from Indian Provisional Patent Application No. 3652/CHE/2015 filed in the Indian Patent Office on Jul. 16, 2015.

FIELD OF INVENTION

The present invention discloses vaccine compositions comprising Zika virus antigens for prophylaxis and treatment of Zika virus infections in mammals. The invention also discloses stable vaccine compositions comprising Zika virus antigens with one or more arbovirus antigens such as Chikungunya and/or Japanese encephalitis virus antigens. The present invention also relates to the methods of preparation, formulation and use of the same for simultaneously eliciting immune response to each of the above mentioned pathogens in mammals, and suitable for immunizing human subjects

BACKGROUND OF THE INVENTION

At present there is no vaccine available in the world for prophylaxis or treatment against Zika virus infections. Therefore, there is no prior art relevant to the invention disclosed in this application. However, for general understanding of the background and objectives behind this invention, the invention is discussed hereinafter in below paragraphs.

The Inventors of this patent application anticipated the epidemic potential of Zika virus in regions with high prevalence of *Aedes* mosquitoes, particularly *Aedes aegypti* that transmits the virus. The interest in initiating the Zika vaccine project early on, several months before the causal link of Zika virus infection to Guillain Bane Syndrome and to microcephaly became public knowledge in December 2015, was that there was no preparedness in any country in the world, nor measures initiated by anyone at that time to develop a vaccine to stop the ongoing virus transmission in countries such as Brazil, and to prevent further transmission in countries at risk for Zika virus. Increased International travel to and from regions with ongoing virus transmission impose a major risk to initiate an outbreak in countries with high prevalence of *Aedes* mosquitoes, particularly *Ae. aegypti* and those having a large naïve population hither to unexposed to the virus. The clinical picture of Zika virus infection in the early stages with characteristic high fever, maculopapular rashes and arthralgia is strikingly similar to the early onset symptoms of Chikungunya and Dengue virus infections that make differential diagnosis particularly challenging.

Zika virus vaccine project was initiated at the time when very little or no information was available on virus pathogenesis, genetic diversity, transmission, diagnosis, serological correlates for protection or animal models to test the vaccine concepts. From vaccine point of view, there was no information on whether the virus can be cultured in vitro in cell substrates and if yes, which cell substrates are best suitable, mechanism of adaptation to cells, potential virus titers and the feasibility to manufacture the vaccine product for human administration, as the published information at that time pertained to passaging the virus in mouse brain which is not suitable for vaccine production. Bharat Biotech initiated steps to start Zika vaccine project in late 2014, and commenced the experimental work soon thereafter resulting into this said patent application.

Arbovirus (arthropod-borne) infections are caused by viruses that are spread by arthropods such as mosquitoes. They cause significant human illness ranging from mild, asymptomatic infection to acute encephalitis or hemorrhagic fever that can prove fatal. The most significant arboviruses causing human illness belong to three viral families, Togaviridae, Flaviviridae, and Bunyaviridae. Arbovirus infections are rampant in developing countries and cause severe morbidity particularly in the elderly population. The common characteristic feature of arbovirus infections caused by Dengue, Chikungunya, Zika, Japanese encephalitis and West Nile viruses among others is fever, headache, myalgia, joint pains with swelling and maculopapular rashes during the acute phase of the viral infection. Arthralgia is particularly a characteristic feature of Chikungunya, Dengue and Zika virus fever. Co-infections are common as the arboviruses largely share the same mosquito vectors such as for example Dengue, Chikungunya and Zika viruses that are transmitted by *Aedes* mosquitoes. Japanese encephalitis virus and West Nile viruses are transmitted predominantly by *Culex* mosquitoes. The problem is acute in developing countries where mosquito vector control programs have been ineffective and largely unsuccessful. The problem is compounded by the fact that there are no robust diagnostic methods available for diagnosing the disease causing viruses with certainty. International travel has aided widespread dissemination of these infectious agents, and diseases like Dengue and Chikungunya hitherto confined to tropical countries are now spread geographically to new areas and to temperate regions. Zika virus is reportedly spread to over 65 countries in the last two years. Autochthonous epidemic outbreaks reported in few countries in these regions are sustained by the local population of mosquito vectors.

Zika virus (ZIKV) is an emerging zoonotic arbovirus, belonging to the Flaviviridae family. Like Dengue and Chikungunya viruses, Zika virus can also be transmitted by *Aedes* mosquitoes more specifically *A. furcifer, A. taylori, A. luteocephalus, A. africanus, A. albopictus* and predominantly by, *A. aegyph*. Travel tourism to nations where the recent epidemics were reported such as Polynesia has aided the geographical spread of the virus infection to Brazil, Columbia, Italy and to other countries. An autochthonous outbreak of the virus was reported in Italy caused by the locally established *Aedes* mosquitoes. In Asia, Zika virus infection has occurred sporadically in Cambodia, Thailand, Indonesia, Malaysia and Bangladesh although large epidemic outbreaks have not been reported in these regions.

Chikungunya virus (CHIKV) is an Alphavirus of the family Togaviridae. The virus causes self-limiting febrile infection characterized by acute onset of high fever, headache, myalgia, arthralgia, swelling in joints and maculopapular rashes. Severe symptoms such hemorrhagia, fulminant hepatitis and neurological symptoms were reported in the more recent epidemics. Chikungunya virus is transmitted by both the *Aedes aegypti* and *Aedes albopictus* mosquitoes. Japanese encephalitis virus (JEV) is also a flavivirus of the family Flaviviridae and is transmitted largely by the *Culex* mosquitoes. JEV is related to Dengue, Yellow fever virus, Zika and West Nile viruses. JEV infection is largely asymptomatic, but in general it causes malaise with fever, headache and other flu-like symptoms. Rarely, the clinical infection progresses to encephalitis with seizures, spastic paralysis, coma and death. Children are particularly susceptible. In the countries endemic for JEV, most adults have natural immunity after childhood infection. Adults not exposed to the infection during childhood are susceptible at any age. The case-fatality rate in JEV caused by encephalitis can be as high as 30%. Neurological complications or psychiatric sequelae occur in high proportion of the cases with encephalitis. Globally, about 3 billion population is at risk for JEV infection. A few vaccines for prophylaxis of JEV infection have been successfully commercialized. Dengue virus (DENY) is a member of Flaviviridae family. The arbovirus infections can no longer be considered region specific as they are now geographically widespread and are significant public health problem in many parts of the world. The morbidity caused by the aforementioned arbovirus infections is usually high, and arthralgia in particular, adversely impacts physical mobility of the patients. Zika virus causes more serious congenital birth deformities during infection in pregnancy, and Zika related Guillain Barre syndrome have been confirmed in the ongoing epidemics. Like any other viral infections, no specific therapeutics is available. Prophylactic vaccination can effectively interrupt Zika virus transmission and a vaccine would be the front line of defense from the Zika virus disease.

With this in mind, an effective strategy was developed to prevent further transmission of Zika virus to protect naïve population in countries with ongoing epdiemics and in countries where active Zika virus transmission has not been reported as yet. A combination vaccine for arbovirus infections is good strategy to protect vulnerable population from debilitating illnesses caused by Dengue, Chikungunya, Zika, Japanese encephalitis, West Nile and Yellow Fever viruses. Vaccines for JEV, Yellow Fever and one for Dengue serotypes has been commercialized and those for West Nile and CHIKV are in clinical development. There is no vaccine for Zika virus infection as yet, and the current invention discloses the methods for development of the first candidate Zika vaccines.

However, the choice of antigens to include in such a vaccine kit depends on several factors. The antibody dependent enhancement of virus caused by the Dengue serotypes is well researched and published and so also the cross reactivity of flavivirus antibodies. But what was not clear is that if there would be such interference or cross reactivity of prevalent Chikungunya antibodies in the same population that is affected by Zika virus. Similarly, it was not known if antibodies to Japanese encephalitis virus could cause antigenic interference in developing immunity to Zika virus and it was an interesting thought to study the same. The proposed work provides an insight to any possible immune interference caused by prevalent JE and CHIKV antibodies to candidate Zika vaccine.

In the current invention, candidate Zika virus vaccines have been developed and tested for potency with various formulations to elicit the appropriate level of immune response to protect against Zika virus disease. As there was no significant antigenic interference to Zika induced immune response by Japanese encephalitis virus vaccine and Chikungunya virus vaccine when co-administered or combined as a combination vaccine, the formulations were effective in eliciting high level of neutralizing antibodies capable of conferring protection against each of the viruses.

OBJECTS OF THE INVENTION

One object of the invention is to provide stable immunogenic compositions for prophylaxis and treatment of Zika virus infections.

Another object of the invention is to provide methods for adaption and growth of Zika virus in Vero cells.

Another object of the invention is to provide methods for the preparation of inactivated Zika virus vaccine Another object of the invention is to provide methods for the purification of Zika virus bulk antigen.

One more object of the invention is to provide methods for Zika virus inactivation by chemical means with formalin, beta propiolactone and hydrogen peroxide Yet another object of the invention is to provide methods for Zika virus inactivation by physical means such as heat, gamma irradiation and ultraviolet light Yet another object of the invention is to provide methods for the preparation and formulation of recombinant Zika virus antigens comprising the prME protein and testing for immunogenicity in animals A further object of the invention is to provide methods for formulations of Zika virus antigens with different adjuvants and estimation of immune response to the formulations in animals.

Yet another object of the invention is to provide kinetics of immune response to single dose, two and three doses of formalin and BPL inactivated Zika virus vaccine in animals.

One more object of the invention is to provide immunogenic compositions for prophylaxis of Zika and Chikungunya virus infections Yet another object of the invention is to provide immunogenic compositions for prophylaxis of Zika and Japanese encephalitis virus infections Another object of the invention is to provide immunogenic compositions for prophylaxis of Zika, Chikungunya and Japanese encephalitis virus infections.

SUMMARY OF THE INVENTION

The present invention is directed to compositions and methods of manufacture of vaccine formulations for prophylaxis and treatment of Zika virus infections as well as infections caused by other arboviruses such as Chikungunya virus and Japanese encephalitis virus.

In one aspect, the invention is directed to vaccine compositions for prophylaxis and treatment of Zika virus infections, wherein the said compositions comprise Zika virus antigens in immunogenic compositions and may also comprise one or more arbovirus antigens such as Chikungunya virus and Japanese encephalitis virus antigens, along with suitable adjuvants and excipients.

In another aspect, the invention is directed to a method of obtaining the vaccine formulations by a process which comprises:
 (a) Using Vero cell line as cell substrate for Zika virus culture
 (b) Scaling up the Zika virus culture upto a harvest volume of 10 L
 (c) Inactivating the virus culture either before or after purification of the virus
 (d) Purifying the virus culture
 (e) In another aspect, recombinant cloning and expressing Zika virus prME protein.

In one embodiment of the invention, Vero cell line was used as the cell substrate for culture of Zika virus and was grown in culture medium with or without the use of serum.

In another embodiment of the invention, the Zika virus was adapted by repeated serial passage in Vero cells to obtain higher titers.

In another embodiment of the invention, Zika virus was passaged in C6/36 *Ae. albopictus* cells followed by growth in Vero cells to increase the titer.

In another embodiment of the invention, processes for scaling up the virus culture and further purifying the scaled up virus cultures is disclosed, wherein the harvest volume was about 8-10 L. The virus was purified by Capto Core 700 column chromatography and then inactivated. Alternately, the viral harvest was inactivated using various methods. The virus was then purified.

In another embodiment of the invention, inactivation method is selected from a group of Formalin inactivation, Beta Propiolactone (BPL) inactivation, heat inactivation, UV inactivation, gamma inactivation, in the presence or absence of virus stabilizing agents and amino acids.

In a preferred embodiment of the invention, amino acids were selected individually or in combination, from a group L-Histidine, L-Glutamic acid, L-Glycine and L-Aspartic acid and L-Glutamine and human serum albumin.

In another preferred embodiment of this invention, the purification method is selected by use of cellufine sulphate, DEAE-Sephadex CM-sephadex with salt gradient, by gel filtration on Captocore-700, Sepharose CL-4B, ceramic hydroxyapatite column with gradient of 0.2M to 0.8M phosphate followed by diafiltration, and ultracentrifugation on a 20-60% sucrose gradient, most preferably by Capto Core 700 column.

Another embodiment of the invention is directed to recombinant cloning and expression of Zika virus prME protein is provided. The method of recombinant cloning utilizes a site specific transposition of the expression cassette with the cloned inserts into a baculovirus shuttle vector propagated in *E. coli* and expressed in insect cells.

In another embodiment of the invention, vaccine formulations are provided. The vaccine may comprise of one or more arbovirus antigens selected from Zika virus, Chikungunya virus and Japanese encephalitis viruses.

In another embodiment, adjuvants can be selected from a group of aluminium salts, inulin, algammulin, combination of inulin and aluminium hydroxide, monophosphoryl lipid A (MPL), resiquimoid, muramyl dipeptide (MDP), N-glycolyl dipeptide (GMDP), poly IC, CpG oligonucleotide, resiquimod, aluminium hydroxide with MPL, any water in oil emulsion, any oil in water emulsion that contains one or more of the following constituents: squalene or its analogues or any pharmaceutically acceptable oil, tween-80, sorbitan trioleate, alpha-tocopherol, cholecalciferol or any of the analogues and derivatives of the molecules thereof, or calcium phosphate or any combination of the adjuvants.

In another embodiment of the invention, the formulations are prepared with excipients and preservatives.

In another embodiment of the invention, stabilizing agents in the vaccine formulation were used individually or in combinations of sorbitol, L-glycine, mannitol, L-glutamic acid and human serum albumin in various concentration was used to study the same.

In another embodiment of the invention, the potency of the vaccine formulations have been tested in animal models to show complete protection from viremia over a wide range of doses.

In another embodiment of the invention, the combination vaccine formulations were also effective in providing adequate protection against Zika, Japanese Encephalitis as well as Chikungunya viruses.

In another embodiment of the invention, the Zika polyclonal antisera confers passive immunity in mice against Zika virus infection by protecting against viremia, while viremia was detected in the control animals that persisted up to 6 days after virus challenge.

In another embodiment of the invention, the candidate inactivated Zika virus vaccine can be administered either as a single dose, or in two or more doses by intramuscular route In another embodiment of the invention, assays for neutralizing antibody titers were conducted to check the antibody levels against vaccine formulations of the present invention which has shown to elicit high level of neutralizing antibodies.

In another embodiment of the invention, cross neutralization studies exhibited that inactivated vaccine formulations of the present invention would be equally protective and potent against any Zika virus strain.

In another embodiment of the invention, prME antisera of the present invention cross neutralized the MR766 strain of the African genotype indicating that no serotypes of Zika virus exist.

In another preferred embodiment of the invention, antibody titers to both BPL inactivated and formalin inactivated Zika vaccine formulations were higher with aluminium hydroxide than with antigens alone.

In another embodiment of the invention, quality of antibody responses to the vaccine formulations of the present invention by antibody avidity assays indicated that high affinity antibodies were elicited by the vaccine formulations.

Accordingly, the invention provides a stable vaccine composition comprising one or more arbovirus antigens selected from Zika virus, Chikungunya virus and Japanese encephalitis virus, said antigens being formulated with or without an adjuvant in pharmaceutically acceptable buffer, wherein the vaccine composition elicits protective immune response to each of the viruses in mammals. The Zika virus antigen of the composition is effective for treatment, diagnosis and prophylaxis against any genotype/genotypic variants/strains of Zika virus, wherein the composition is effective against any genotype/genotypic variants/strains/ synthetic Zika viruses that share anywhere between 50% to 100% identity at the amino acid level in any region of the genome. The composition of the invention comprises Zika virus antigens of any genotype/genotypic variant/strains/ synthetic Zika virus, wherein the antibodies against any of the aforementioned Zika virus types cross neutralizes the homologous virus or any heterologous Zika virus strain that shares at least 50%-100% amino acid identity in any region of its whole genome, particularly the envelope E protein.

The antigens of Zika virus, Chikungunya virus and Japanese encephalitis virus of the composition are inactivated whole virion (virus) antigens. Whereas, in another embodiment, the Zika and Chikungunya virus antigens are purified recombinant antigens.

The Zika virus antigen of the invention is prepared using Vero cells as cell substrate by adapting the virus to Vero cells.

The Zika virus antigen of the composition of the invention is a purified and concentrated antigen obtained from one or more methods selected from:
  a. ultracentrifugation;
  b. density gradient centrifugation;
  c. clarification of the viral harvest using membrane filtration, followed by purification by column chromatography; and
  d. tangential flow filtration using membranes with cut off from 100 kDa to 300 kDa, wherein tangential filtration is carried out either before or after virus inactivation.

Wherein the purification by column chromatography comprises gel filtration, mixed mode resin column chromatography, ion exchange column chromatography, affinity matrix chromatography and hydrophobic interaction chromatography. The column chromatography elutes majority of the virus antigen in the flow through such as Capto Core 700, most preferably Capto Core 700 wherein the virus sample is purified on Capto Core 700 column and is eluted in the flow through.

The Zika virus of the composition is inactivated by at least one or more of a chemical inactivating agent, a physical inactivating agent and an irradiating agent, wherein the inactivation of Zika virus is carried out before or after purification of the virus. In an exemplary embodiment, the Zika virus is inactivated by chemical inactivating agent selected from formalin (formaldehyde), beta propiolactone (BPL) and hydrogen peroxide.

In one preferred embodiment the Zika virus is inactivated by any one of the following methods selected from:
  a. Formalin treatment at any concentration ranging from 1:500 up to 1:4000 v/v of formalin:virus, at 8° C. to 37° C., preferably 25±3° C., for at least 1 to 7 days;
  b. Formalin treatment at any concentration ranging from 1:500 up to 1:4000 v/v of formalin:virus, at 2° C. to 8° C. for at least 10 to 30 days;
  c. Beta propiolactone (henceforth BPL) at any concentration ranging from 1:500 up to 1:4000 v/v of BPL:virus, for at least 24 to 48 hours at temperatures ranging from 8° C. to 30° C., preferably 25±3° C., for 48 hours;
  d. Beta propiolactone at any concentration ranging from 1:500 up to 1:4000 (BPL:virus, v/v), at 2° C. to 8° C. for at least 3-7 days;
  e. A combination of BPL and formalin at any of the aforementioned conditions, preferably BPL inactivation at 1:3000 (BPL:virus, v/v) for 24 hours followed by formalin inactivation at 1:3000 (formalin:virus, v/v) for 24 to 48 hours at 15° C. to 30° C., preferably 25±3° C.;
  f. Hydrogen peroxide at any concentration from 0.1 to 3%, preferably 0.1 to 1% at any temperature from 20-30° C. for 5 minutes to 120 minutes.

In one embodiment, the inactivation of the Zika virus by irradiating agent comprises inactivation by gamma irradiation by exposure from 20 kGy (Kilo Gray) up to 35 kGy, preferably 25 kGy to 30 kGy from a $^{60}$Co source.

In another embodiment, the inactivation of the Zika virus by irradiating agent comprises inactivation by UV irradiation by exposure to 254 nm for 30-60 minutes.

In a further embodiment, the virus is inactivated by heat treatment at a temperature between 50° C. to 65° C. for 30 min up to 2 hrs.

The buffer used in the invention may be selected from the list comprising of phosphate buffer, citrate buffer, phosphate citrate buffer, borate buffer, tris(hydroxymethyl) aminomethane (Tris) containing buffer, succinate buffer, buffers containing glycine or histidine as one of the buffering agents, wherein phosphate buffer is sodium phosphate buffer at concentration of 5 mM up to 200 mM of phosphate ions of any pH between 6.50 to pH 9, and optionally containing sodium chloride at a concentration of 50 to 200 mM. The buffer maintains the pH in a liquid composition above pH 6.5, preferably above pH 7.0 throughout the bioprocess from viral culture up to preparation of purified inactivated virus bulk.

In one embodiment, the inactivation of Zika virus is carried out in the presence of a stabilizing agent selected from lactose, sucrose, trehalose, maltose, mannose, isomaltose, raffinose, stachyose, lactobiose, sorbitol, mannitol, lactobionic acid, dextran, L-glycine, L-histidine, L-glutamic acid, L-aspartic acid and human serum albumin or combinations thereof. However, in one preferred embodiment, the stabilizing agent may be selected from:
  a. 2% sorbitol and 1% L-glycine;
  b. 1% sorbitol and 0.5% L-glycine;
  c. 1% mannitol and 0.5% L-glycine;
  d. 1% mannitol and 0.5% L-glutamic acid; and
  e. 1% sorbitol and 0.5% L-glycine, 1% human serum albumin.

In an exemplary embodiment, the inactivation of Zika virus comprises inactivation of any genotype/strain, live attenuated Zika virus, deactivated virus, virus like particles, chimeric virus particles that carry any Zika virus antigens particularly the E protein in any heterologous virus backbone, in vectored vaccines and infectious synthetic virus particles derived in vitro or in vivo using the sequence of any Zika virus genome.

The purified recombinant Zika virus of the invention comprises antigens of Zika virus comprising the envelope (E) protein, membrane (M) protein expressed as prME and optionally the non-structural 1 (NS1) protein as vaccine antigens for eliciting immune response for prophylaxis of Zika virus infections, wherein the Zika virus has the structural protein sequences as disclosed in SEQ. ID NO:3 and SEQ ID NO:4 corresponding to nucleotide sequences of SEQ ID NO:1 and SEQ ID NO:2 respectively, for use as vaccine antigens against Zika virus infections caused by genotypes or variants thereof. The Recombinant DNA constructs comprises a (i) vector (ii) at least one nucleic acid fragment corresponding to SEQ ID NO:1 or SEQ ID NO:2 encoding the amino acid sequence of the proteins of SEQ ID NO:3, SEQ ID NO:4 respectively which is applicable to any Zika virus protein sequences that share at least 70% amino acid identity to the aforementioned SEQ ID NO:3 and SEQ ID NO:4. The composition of the invention comprises recombinant DNA construct, wherein the vector is an eukaryotic plasmid vector being cloned in a eukaryotic host such as baculovirus for expression in insect cells as virus like particles (VLPs).

The recombinant protein of Zika virus is obtained by the process comprising the steps of:
  a. transfecting the recombinant plasmid DNA in insect cells;
  b. harvesting the cells and isolating the recombinant protein therefrom;
  c. purifying the protein by a method selected from ion exchange chromatography, gel filtration, affinity chromatography, hydrophobic column chromatography, mixed mode resin chromatography, diafiltration, ultracentrifugation, density gradient centrifugation and fractionation with salt.

The structural antigens of Zika virus are expressed in any prokaryotic or eukaryotic expression system including baculovirus mediated expression in insect cells.

The vaccine composition of the invention is obtained by a process wherein neutralizing antibodies are largely elicited against the Envelope protein such as in optimally inactivated virus, live attenuated virus, deactivated virus, DNA vaccine, virus like particles, chimeric virus particles that display the Zika virus E protein in any heterologous virus backbone such as in vectored vaccines and synthetic virus particles derived from any Zika virus genomic RNA sequence.

The vaccine composition of the invention may further comprise an adjuvant, wherein the adjuvant is selected from the group consisting of a) aluminum salts comprising aluminum hydroxide, aluminum phosphate, aluminum sulphate phosphate; b) inulin; c) algammulin which is a combination of inulin and aluminum hydroxide; d) monophosphoryl lipid A (MPL); e) resiquimod; f) muramyl dipeptide (MDP); g) N-glycolyl dipeptide (GMDP); h) polyIC; i) CpG oligonucleotide; j) aluminum hydroxide with MPL; k) any water in oil emulsion; 1) any oil in water emulsion that contains one or more of the following constituents: squalene or its analogues or any pharmaceutically acceptable oil, tween-80, sorbitantrioleate, alpha-tocopherol, cholecalciferol and aqueous buffer, or any of the analogues and derivatives of the molecules thereof, wherein one or two or more combination of any of the aforementioned adjuvants when formulated with Zika virus antigens elicits immune response against the virus.

In one preferred embodiment the composition comprises aluminum hydroxide in a concentration range of 0.1 mg to 1.5 mg of aluminum per vaccine dose, preferably 0.25 mg to 0.5 mg aluminum per vaccine dose, The adjuvant of the composition of the invention confers mucosal immunity and systemic immunity when administered in mammals.

The vaccine composition with Zika virus antigen is administered at any dose ranging from 0.125 µg to 100 µg per dose with or without an adjuvant, either as a single dose or in two or more doses to elicit an immune response in a mammal.

In one embodiment the invention provides a method of eliciting a protective immune response in mammals including humans comprising administering the vaccine composition of claim 1 by any route comprising intramuscular, intradermal, subcutaneous, intravenous, oral, intranasal or transcutaneous routes.

The composition of the invention may be administered by any method comprising needles and syringes including pre-filled syringes, microneedle patch, needle-free patch, inhalation and nasal sprays.

The invention also provides a method of in vitro or in vivo use of the Zika virus antibodies of the composition for preparation of immunodiagnostic and immunotherapeutic agents for Zika virus infections.

In one embodiment the vaccine composition comprises Zika virus and Japanese encephalitis virus antigens in a combination vaccine that elicits protective immune response in mammals against each of the viruses, wherein the Zika virus antigen and Japanese encephalitis virus inactivated antigens are present in the combination vaccine at concentrations ranging 5 µg to 50 µg of each antigen in a pharmaceutically acceptable formulation without an adjuvant, or with an adjuvant.

The adjuvant may be selected from the group consisting of a) aluminum salts comprising aluminum hydroxide, aluminum phosphate, aluminum sulphate phosphate; b) inulin; c) algammulin which is a combination of inulin and aluminium hydroxide; d) monophosphoryl lipid A (MPL); e) resiquimod; f) muramyl dipeptide (MDP); g) N-glycolyl dipeptide (GMDP); h) polyIC; i) CpG oligonucleotide; j) aluminum hydroxide with MPL; k) any water in oil emulsion; l) any oil in water emulsion that contains one or more of the following constituents: squalene or its analogues or any pharmaceutically acceptable oil, tween-80, sorbitantrioleate, alpha-tocopherol, cholecalciferol and aqueous buffer, or any of the analogues and derivatives of the molecules thereof wherein one or two or more combination of any of the aforementioned adjuvants when formulated with Zika virus and Japanese encephalitis virus antigens elicits immune response against the virus. In one preferred embodiment, the adjuvant is aluminum hydroxide with 0.25 mg to 1.0 mg of aluminum content per vaccine dose.

In another embodiment, the vaccine composition comprises Zika virus and Chikungunya virus antigens in a combination vaccine that elicits protective immune response in mammals against each of the viruses, wherein Zika and Chikungunya virus antigens are present in a combination vaccine at concentrations ranging from 5 µg to 50 µg of each antigen in a pharmaceutically acceptable formulation without an adjuvant, or with an adjuvant.

The adjuvant may be selected from the group consisting of a) aluminum salts comprising aluminum hydroxide, aluminum phosphate, aluminum sulphate phosphate; b) inulin; c) algammulin which is a combination of inulin and aluminium hydroxide; d) monophosphoryl lipid A (MPL); e) resiquimod; f) muramyl dipeptide (MDP); g) N-glycolyl dipeptide (GMDP); h) polyIC; i) CpG oligonucleotide; j) aluminum hydroxide with MPL; k) any water in oil emulsion; l) any oil in water emulsion that contains one or more of the following constituents: squalene or its analogues or any pharmaceutically acceptable oil, tween-80, sorbitantrioleate, alpha-tocopherol, cholecalciferol and aqueous buffer, or any of the analogues and derivatives of the molecules thereo, wherein two or more combination of any of the aforementioned adjuvants when formulated with Zika virus and Chikungunya virus antigens elicits immune response against the virus. In one preferred embodiment, the adjuvant is aluminum hydroxide at 0.25 mg to 1.5 mg of aluminum content per vaccine dose.

In another embodiment, the vaccine composition comprises Zika virus, Chikungunya virus and Japanese encephalitis virus antigens in a combination vaccine that elicits protective immune response in mammals against each of the viruses, wherein Zika virus, Chikungunya virus and Japanese encephalitis virus antigens are present in a combination vaccine at concentrations ranging from 5 µg to 50 µg of each antigen in a pharmaceutically acceptable formulation without an adjuvant, or with an adjuvant.

The adjuvant may be selected from the group consisting of a) aluminum salts comprising aluminum hydroxide, aluminum phosphate, aluminum sulphate phosphate; b) inulin; c) algammulin which is a combination of inulin and aluminum hydroxide; d) monophosphoryl lipid A (MPL); e) resiquimod; f) muramyl dipeptide (MDP); g) N-glycolyl dipeptide (GMDP); h) polyIC; i) CpG oligonucleotide; j) aluminum hydroxide with MPL; k) any water in oil emulsion; l) any oil in water emulsion that contains one or more of the following constituents: squalene or its analogues or any pharmaceutically acceptable oil, tween-80, sorbitantrioleate, alpha-tocopherol, cholecalciferol and aqueous buffer, or any of the analogues and derivatives of the molecules thereof wherein one or two or more combination of any of the aforementioned adjuvants when formulated with Zika, Chikungunya and Japanese encephalitis virus antigens elicits immune response against the virus. Preferably, the adjuvant is aluminium hydroxide at 0.25 mg to 1.0 mg of aluminium content per vaccine dose.

The vaccine composition of the invention optionally comprises 2-phenoxyethanol preservative at a concentration of 2.5 to 5 mg/mL.

The vaccine composition when administered in a single dose or in two or more doses in mammals elicits Th1 and Th2 immune response against any of the arbovirus antigens comprising Zika Virus, Chikungunya virus and Japanese Encephalitis virus and is suitable for administration to humans.

In one embodiment the invention provides a method for preparation of a vaccine composition comprising one or more arbovirus antigens selected from Zika virus, Chikungunya virus and Japanese encephalitis virus, the method comprising one or more steps of inactivation, producing recombinant protein, expressing structural antigens, purification and concentration of the virus antigen wherein said purification and concentration of Zika virus comprises one or more steps selected from:
a. ultracentrifugation;
b. density gradient centrifugation;
c. clarification of the viral harvest using membrane filtration;
d. purification by column chromatography;
e. tangential flow filtration using membranes with cut off from 100 kDa to 300 kDa, wherein tangential filtration is carried out either before or after virus inactivation.

The column chromatography method comprises gel filtration, mixed mode resin column chromatography, any ion exchange column chromatography, affinity matrix chromatography and hydrophobic interaction chromatography, wherein the column chromatographic method elutes majority of the virus antigen in the flow through such as Capto Core 700, most preferably Capto Core 700 wherein the virus sample is purified on Capto Core 700 column and is eluted in the flow through.

The Zika virus is inactivated by one or more inactivating agents selected from a chemical inactivating agent, a physical inactivating agent and an irradiating agent.

The preparation method comprises inactivation of Zika virus which may be carried out before or after purification of the virus, wherein the Zika virus may be inactivated by chemical inactivating agent selected from formalin (formaldehyde), beta propiolactone (BPL) and hydrogen peroxide.

In one embodiment, the preparation method comprises inactivation of the Zika virus bulk which is inactivated by any one of the following methods selected from:
a. Formalin treatment at any concentration ranging from 1:500 up to 1:4000 v/v of formalin:virus, at 8° C. to 37° C., preferably 25±3° C., for at least 1 to 7 days;
b. Formalin treatment at any concentration ranging from 1:500 up to 1:4000 v/v of formalin:virus, at 2° C. to 8° C. for at least 10 to 30 days;
c. Beta propiolactone (henceforth BPL) at any concentration ranging from 1:500 up to 1:4000 v/v of BPL:virus, for at least 24 to 48 hrs, if not more, at temperatures ranging from 8° C. to 30° C., preferably 25±3° C., for 48 hours;
d. Beta propiolactone at any concentration ranging from 1:500 up to 1:4000 (BPL:virus, v/v), at 2° C. to 8° C. for at least 3-7 days;
e. a combination of BPL and formalin at any of the aforementioned conditions, preferably BPL inactivation at 1:3000 (BPL:virus, v/v) for 24 hours followed by formalin inactivation at 1:3000 (formalin:virus, v/v) for 24 to 48 hours at 15° C. to 30° C., preferably 25±3° C.;
f. hydrogen peroxide at any concentration from 0.1 to 3%, preferably 0.1 to 1% at any temperature from 20-30° C. for 5 minutes to 120 minutes.

In embodiment of preparation method, the virus is inactivated by gamma irradiation by exposure from 20 kGy (Kilo Gray) up to 35 kGy, preferably 25 kGy to 30 kGy from a $^{60}$Co source.

In another embodiment of preparation method, the Zika virus is inactivated by UV irradiation by exposure to 254 nm for 30-60 minutes.

In another embodiment of the preparatory method, the Zika virus is inactivated by heat treatment from 50° C. to 65'C for 30 min up to 2 hrs, preferably, 65° C. for 1 hr.

In one embodiment of the preparation method, the inactivation is carried out in the presence of stabilizing agent selected from lactose, sucrose, trehalose, maltose, mannose, iso-maltose, raffinose, stachyose, lactobiose, sorbitol, mannitol, lactobionic acid, dextran, L-glycine, L-histidine, L-glutamic acid, L-aspartic acid and human serum albumin or combinations thereof. In one preferred embodiment the stabilizing agent is selected from:
a. 2% sorbitol and 1% L-glycine;
b. 1% sorbitol and 0.5% L-glycine;
c. 1% mannitol and 0.5% L-glycine;
d. 1% mannitol and 0.5% L-glutamic acid; and
e. 1% sorbitol and 0.5% L-glycine, 1% human serum albumin.

The inactivation methods described hereinabove are applicable to Zika virus of any genotype/strain, live attenuated Zika virus, deactivated virus, virus like particles, chimeric virus particles that carry any Zika virus antigens particularly the E protein in any heterologous virus backbone, in vectored vaccines and infectious synthetic virus particles derived in vitro or in vivo using the sequence of any Zika virus genome.

In one embodiment the invention discloses a method of producing the recombinant protein comprising the steps of:
a. transfecting recombinant plasmid DNA in insect cells;
b. harvesting the cells and isolating the recombinant protein therefrom;
c. purifying the protein by at least one of the methods comprising of ion exchange chromatography, gel filtration, affinity chromatography, hydrophobic column chromatography, mixed mode resin chromatography, diafiltration, ultracentrifugation, density gradient centrifugation, fractionation with salt.

In another embodiment, the invention discloses method of expressing the structural antigens of Zika virus comprising expression system is any prokaryotic or eukaryotic expression system including baculovirus mediated expression in insect cells.

In another embodiment the invention discloses a method wherein the method comprises neutralizing antibodies that are largely elicited against the Envelope protein such as in optimally inactivated virus, live attenuated virus, deactivated virus, DNA vaccine, virus like particles, chimeric virus particles that display the Zika virus E protein in any heterologous virus backbone such as in vectored vaccines and synthetic virus particles derived from any Zika virus genomic RNA sequence.

The vaccine composition of the invention may be administered in a prime boost strategy, wherein the prime is the candidate inactivated vaccine and the boost is either the same vaccine or any other vaccine such as DNA vaccine, Chimeric Zika virus vaccine, virus like particles, deactivated Zika vaccine, live attenuated virus vaccine, recombinant subunit vaccine, vectored vaccine or any vaccine derived from synthetic Zika virus, wherein the neutralizing antibodies in each of them are elicited against Zika virus Envelope protein.

Figure 1:
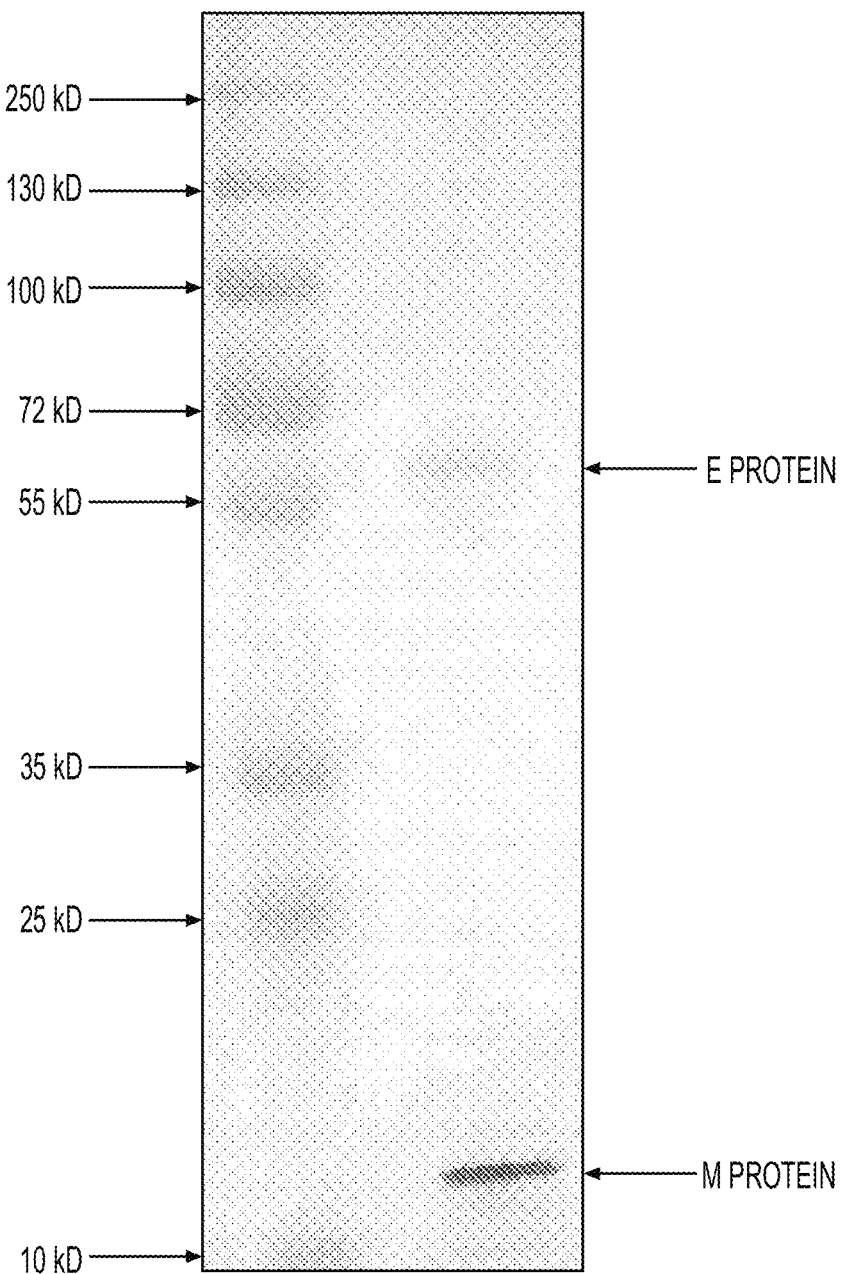
FIG. 1: Purified Zika virus bulk in 12.5% SDS-PAGE gel detected by silver staining. The Envelope (E) protein and the Membrane (M) proteins are the major proteins detected in the purified antigen
Figure 2A:
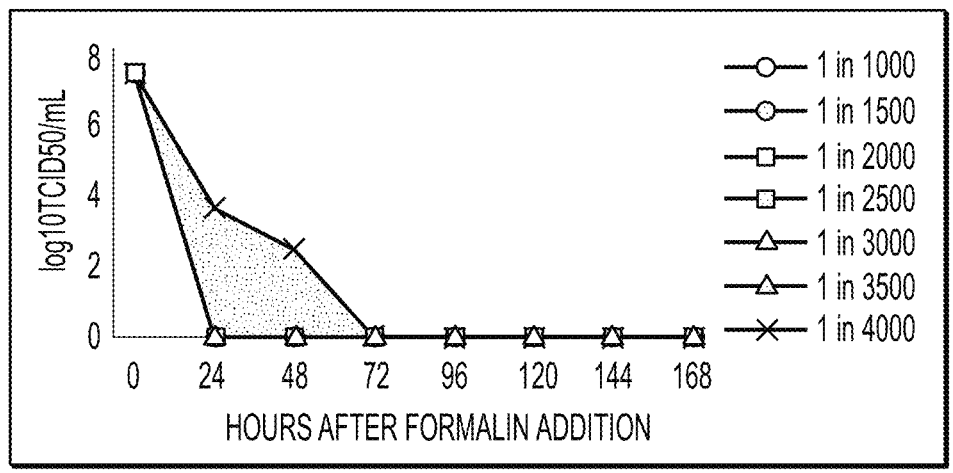
FIG. 2A: Inactivation kinetics of Zika virus by formalin at concentrations ranging from 1:1000 v/v of formalin:virus up to 1:4000 v/v of formalin:virus at 25±3° C.
Figure 2B:
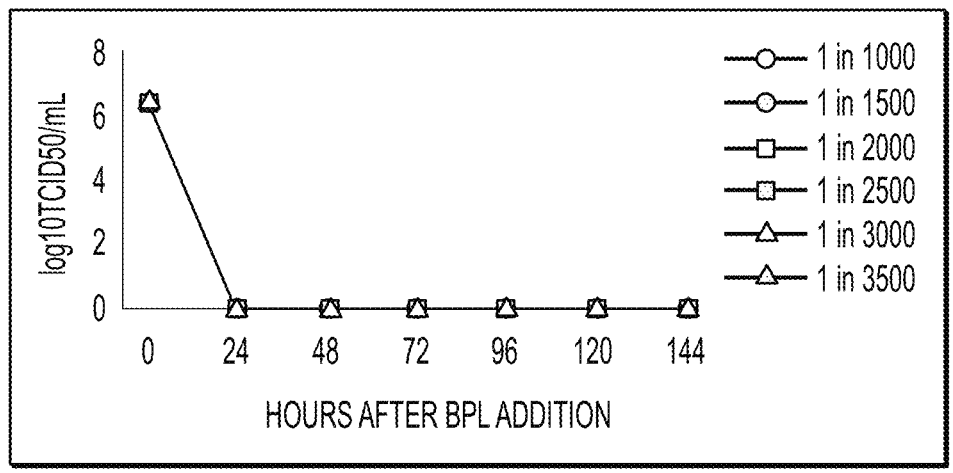
FIG. 2B: inactivation kinetics of Zika virus by beta-propiolactone at concentrations ranging from 1:1000 up to 1:3500 v/v of BPL:virus at 25±3° C.

In both the inactivation procedures, of FIG. 2A and FIG. 2B, 1% sorbitol ad 0.5% L-glycine (final concentration) were added as stabilizers, which had no effect on the inactivation kinetics. The inactivated samples were serially amplified three times in vitro in Vero cells, and assayed at the end of three passages by TCID50.

FIG. 3A: The ~2.1 kb Zika virus prME gene of SEQ ID NO.1 was amplified by gene specific primers for initiating cloning in pFastBac vector for expression in insect cells.

FIG. 3B: The Sf9 cell lysate was probed by Western for detection of expression of the prME protein using Zika rabbit polyclonal antisera by standard procedures. The envelope protein of 55 kD could be detected as the major band.

Figure 4:
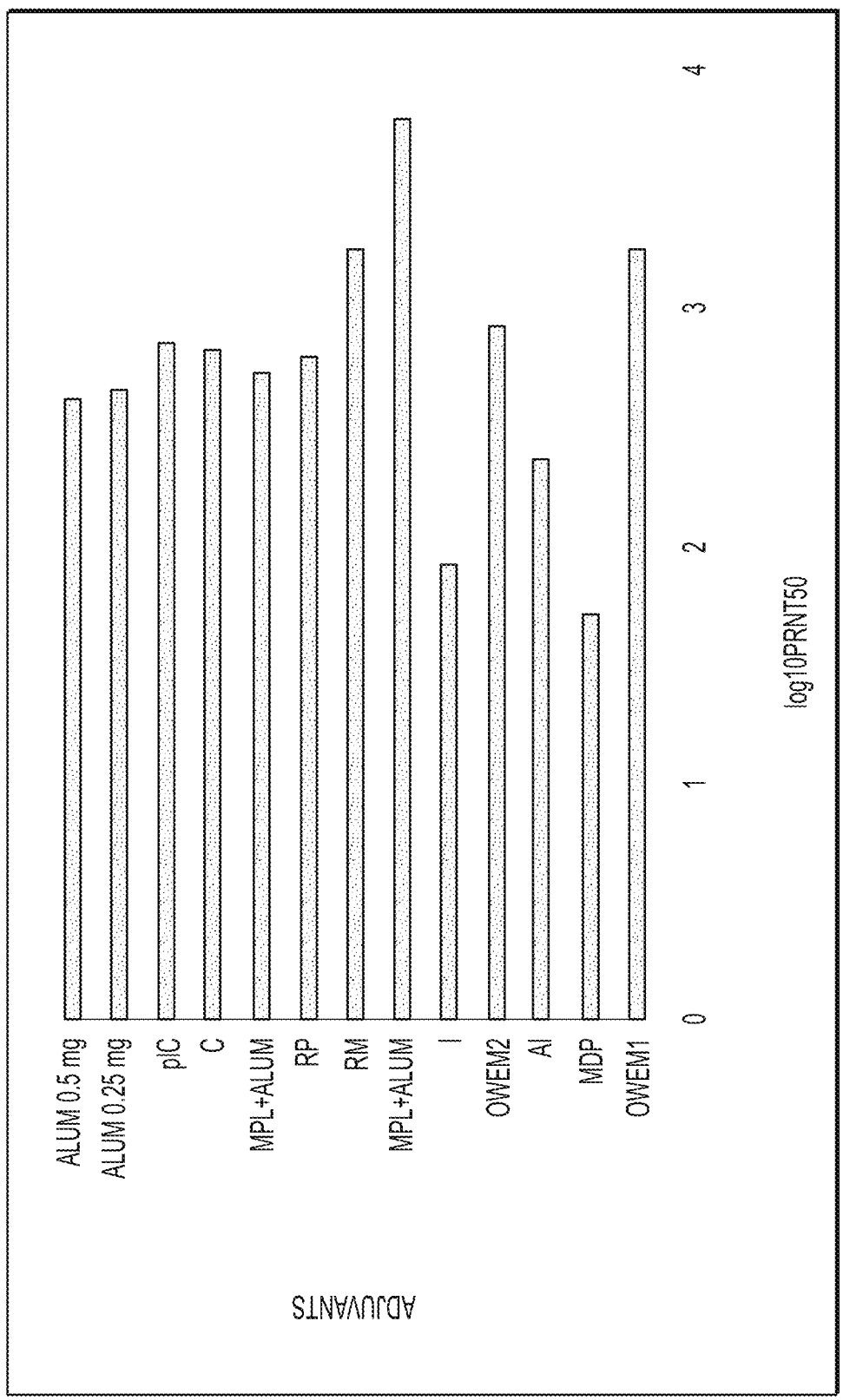

FIG. 4: Estimation of neutralizing antibody titers elicited by Zika vaccine formulations with different adjuvants. Adjuvants are abbreviated as follows: pIC (polyIC); C—cholecalciferol; MPL (lipid A; monophosphoryl); RP (resiquimod+polyIC); RM (resiquimod+OWEM2); I (inulin); OWEM2 (oil in water emulsion 2); AI (aluminum hydroxide+inulin); MDP (muramyldi peptide); OWEM1 (oil in water emulsion 1). No significant antibody titers could be detected in the respective control groups and hence not depicted in the figure. In all cases, 10 µg of two doses of Zika vaccine antigen was formulated for administration in Balb/c mice by IM route.

Figure 5A:
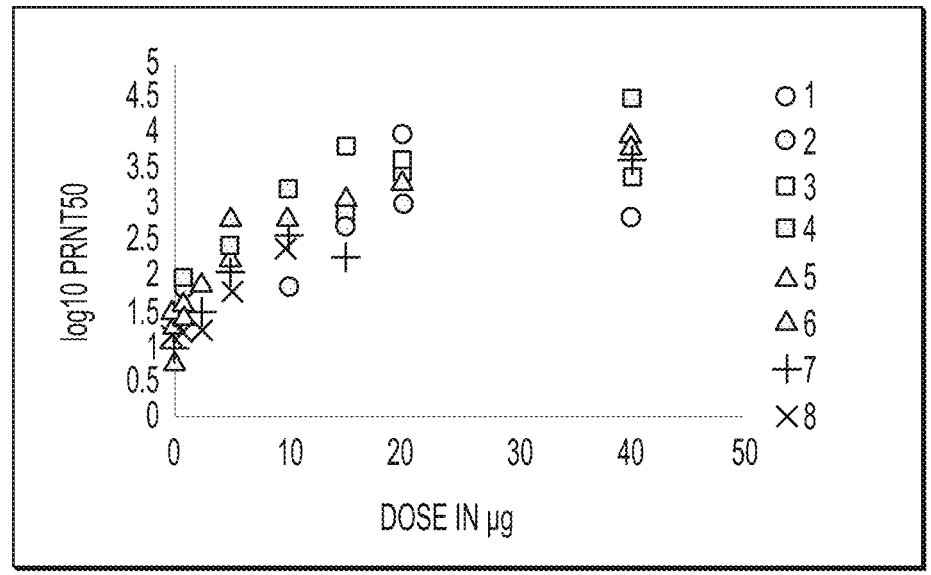

FIG. 5A: Estimation of neutralizing antibody titers by $PRNT_{50}$ in dose ranging studies from 0.125 µg up to 40 µg per dose of the aluminum hydroxide adjuvanted formalin inactivated Zika virus vaccine administered by IM route in Balb/c mice in two doses.

Figure 5B:
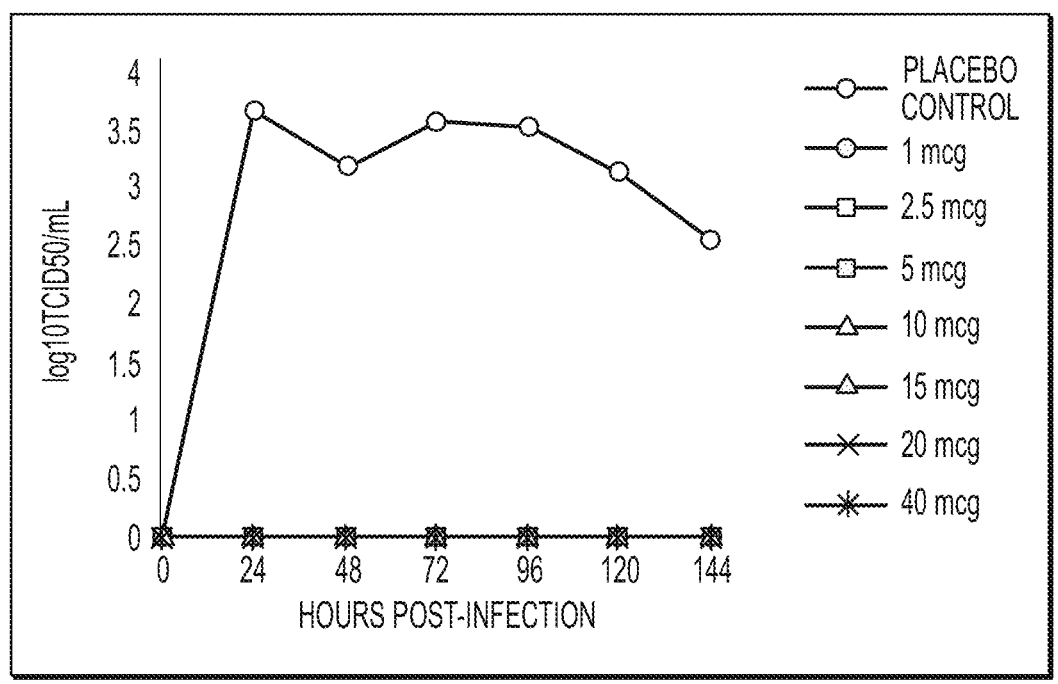

FIG. 5B: the vaccinated animals were challenged intravenously with 10e5 PFU/animal of the Zika virus strain 7 days after the booster dose, and viremia was monitored every 24 hours for 7 days (depicted in the graph for 6 days). All the animals showed complete protection from viremia whereas the animals administered the placebo control showed viremia that persisted up to 6 days. The infectious virus was estimated in the blood samples by $TCID_{50}$.

Figure 6:
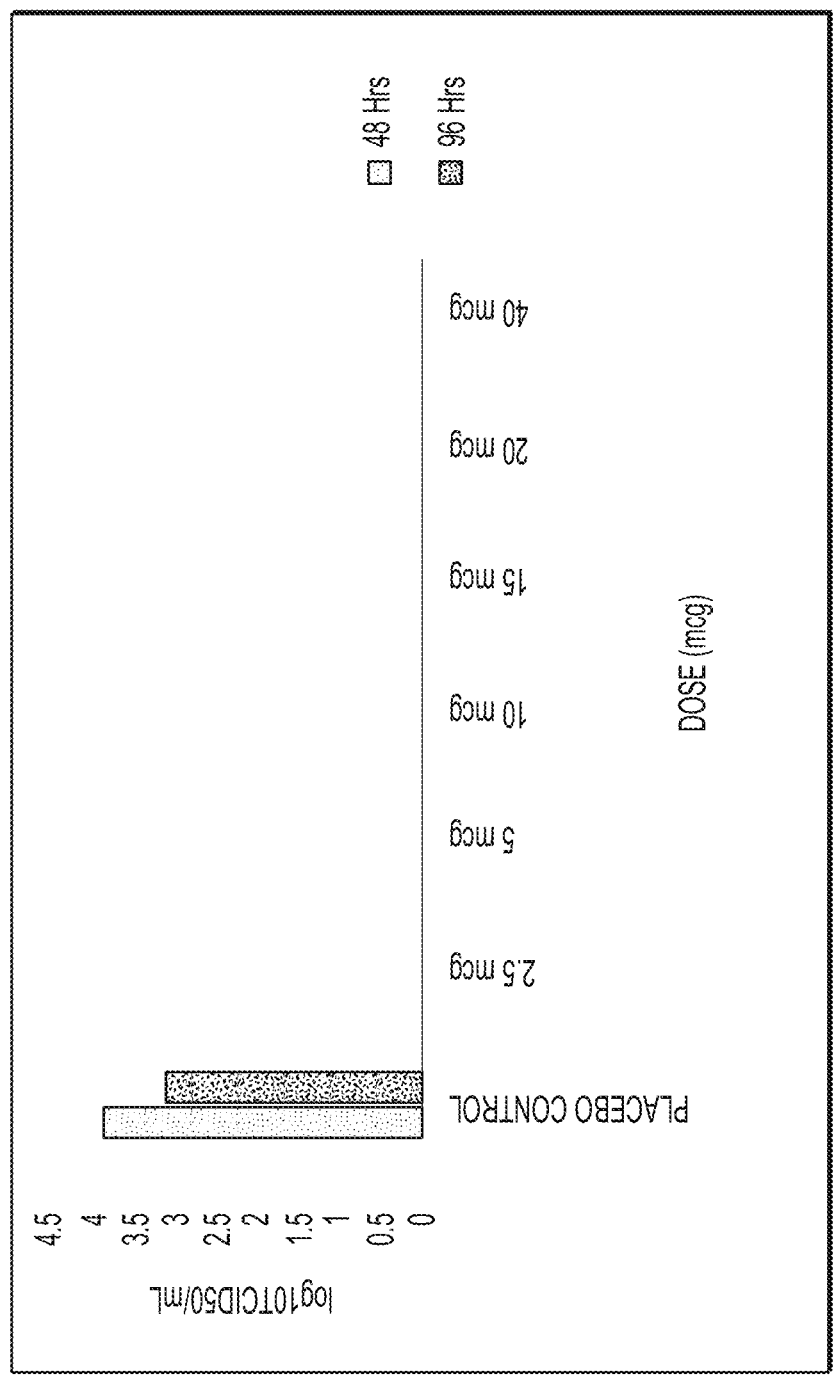

FIG. 6: Virus challenge in 4-6 week old Balb/c mice after administration of 1 µg to 40 µg of BPL inactivated, alum adsorbed Zika virus vaccine. Animals of all the vaccine dose groups and the placebo group were challenged with 10e5 PFU of Zika virus MR766 strain 7 days after administration of the booster dose. Viremia was monitored at 48 and 96 hours after virus challenge, and the titers of infectious particles in blood were estimated by $TCID_{50}$. The candidate Zika vaccine offered complete protection from virus challenge in all the dose groups.

Figure 7:
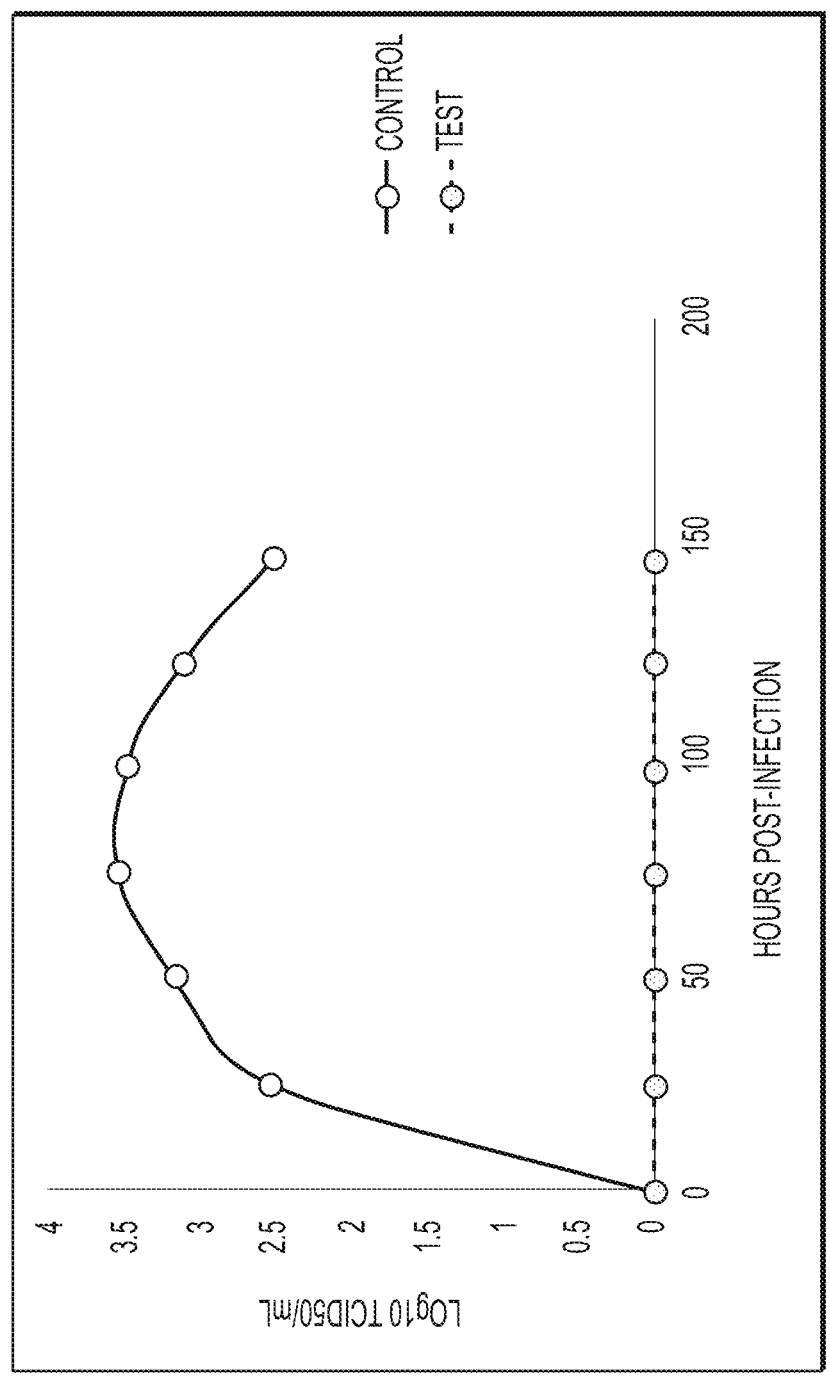

FIG. 7: Passive immunization offered complete protection against viremia and infectious virus could not be detected by $TCID_{50}$ in the animals that received Zika rabbit polyclonal antisera intraperitoneally and challenged 24 later with 10e5 PFU of Zika virus. Infectious virus particles could not be detected by $TCID_{50}$ in the blood, when monitored every 24 hours for 6 days, whereas the control animals that received equal volume of PBS showed persistent viremia up to 6 days when challenged with the same dose of the virus.

Figure 8A:
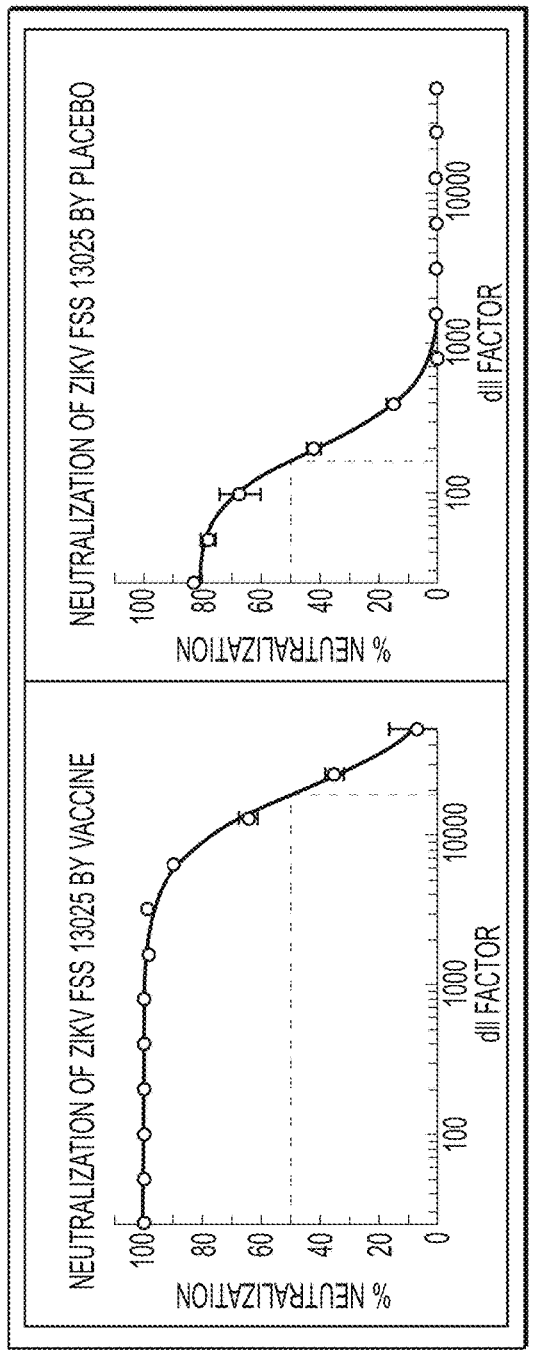

FIG. 8A: Neutralization of FSS 13025 Zika virus strain by vaccine and placebo.

Figure 8B:
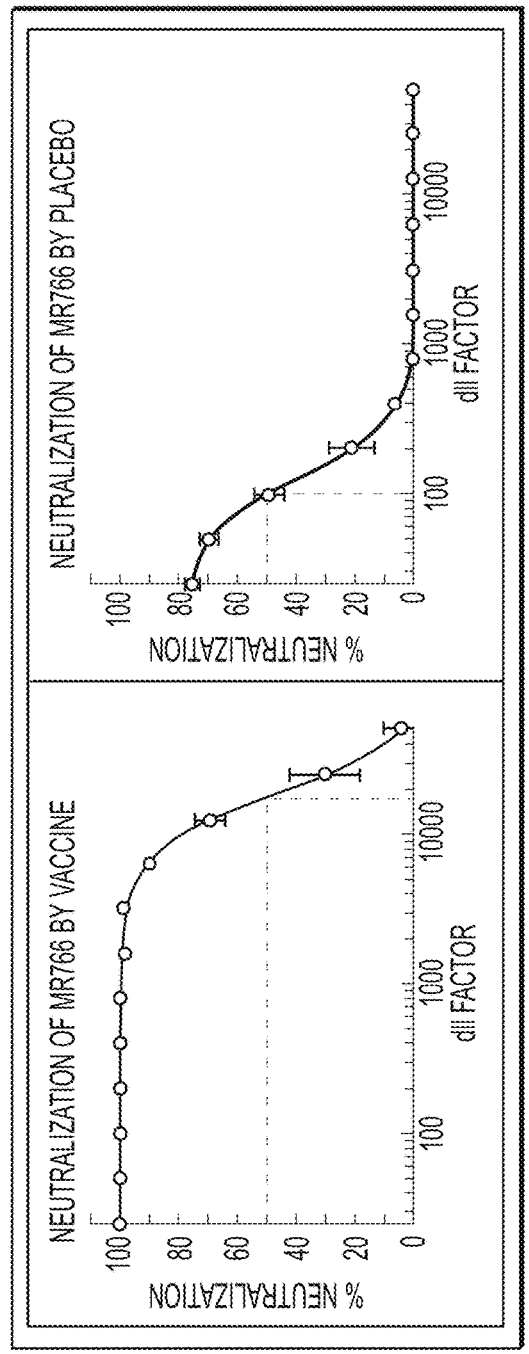

FIG. 8B: Neutralization of MR766 Zika virus strain by vaccine and placebo.

Formalin inactivated, alum adsorbed Zika virus vaccine antisera from vaccinated mice neutralized the homologous MR766 Zika virus strain (FIG. 8B) and cross neutralized the heterologous Asian genotype FSS 13025strain (FIG. 8A) with equal efficiency with $PRNT_{50}$ titers of 18105 and 18325 respectively. The values for the placebo (alum only) are also depicted in the graph alongside.

Figure 9A:
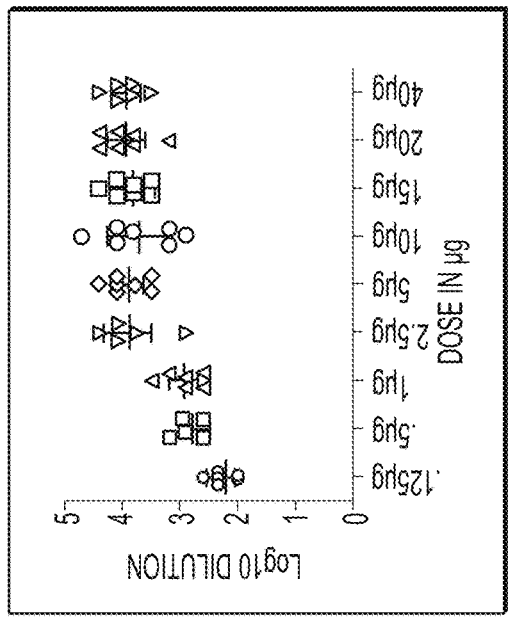

FIG. 9A: Antibody titers expressed as log 10 of reciprocal of serum dilutions from the dose ranging studies with single dose of formalin inactivated vaccine administered in 4-6 week old Balb/c mice as described in Example 7.

Figure 9B:
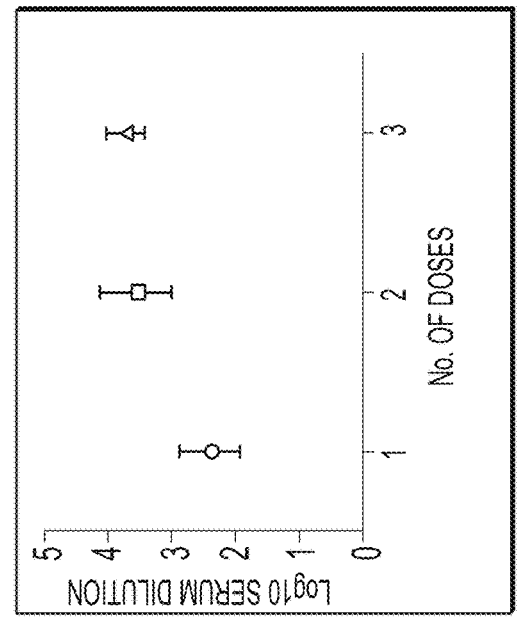

FIG. 9B: Antibody titers expressed as log 10 of reciprocal of serum dilutions from the dose ranging studies with two doses of formalin inactivated vaccine administered in 4-6 week old Balb/c mice as described in Example 7.

Figure 9C:
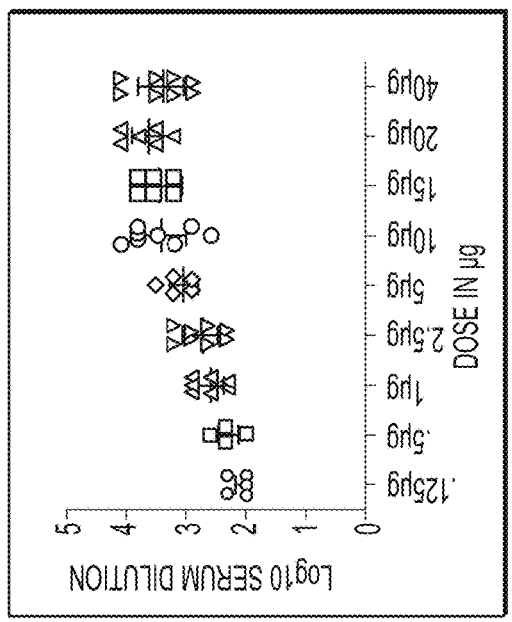

FIG. 9C: Antibody titers expressed as log 10 of reciprocal of serum dilutions from the dose ranging studies with three doses of formalin inactivated vaccine administered in 4-6 week old Balb/c mice as described in Example 7.

Figure 9D:
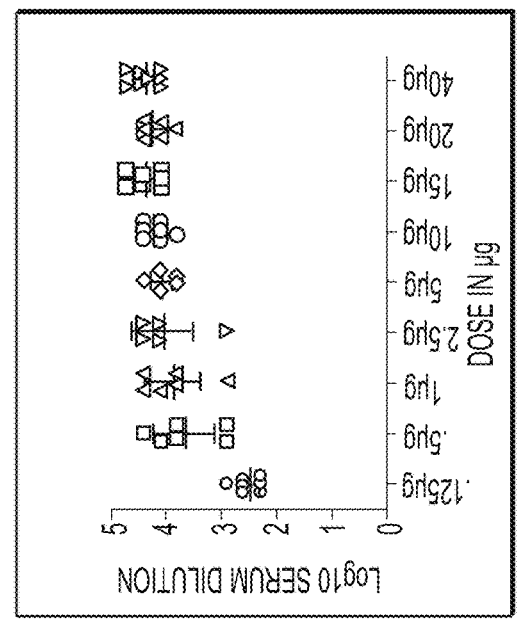

FIG. 9D: Antibody titers with a single, two and three doses of 10 µg of vaccine antigen without alum. All values are expressed as Geometric Mean Titers with 95% CI.

In 9A-9D, individual animal data is plotted. Zika virus antigen was immunogenic even without an adjuvant. Data from other dose ranges were estimated but not included in the graph.

Figure 10:
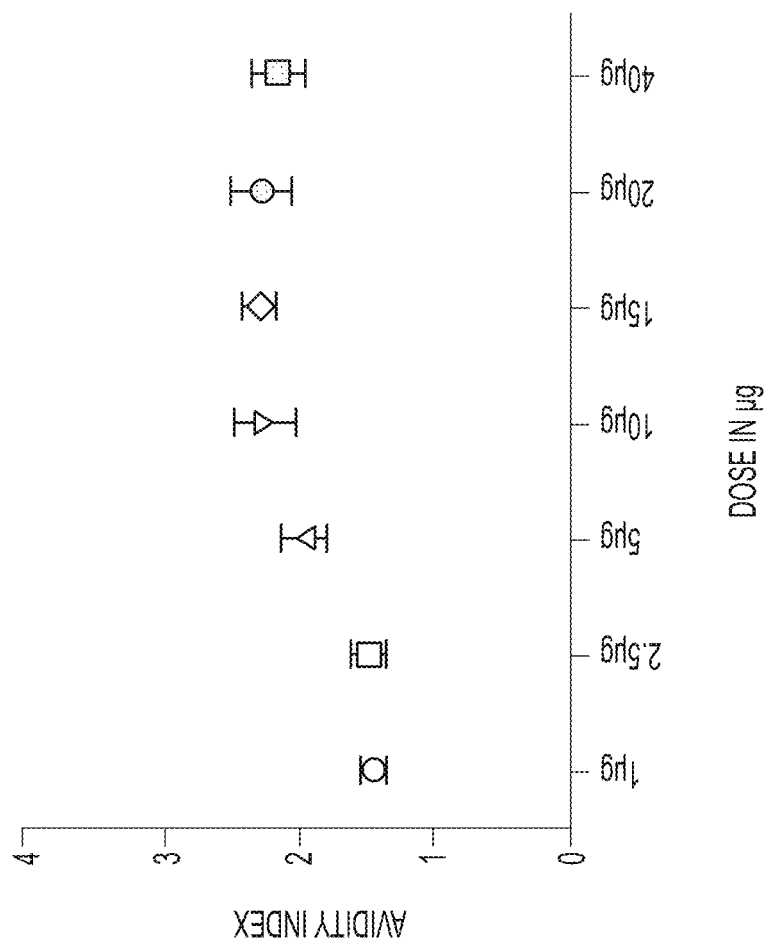

FIG. 10: High affinity antibodies could be elicited by single dose of formalin inactivated alum adsorbed Zika virus vaccine in Balb/c mice even at low doses of the vaccine antigen up to 1 µg. Antibody avidity was expressed as avidity index and estimated by methods described in Example 12.

Figure 11A:
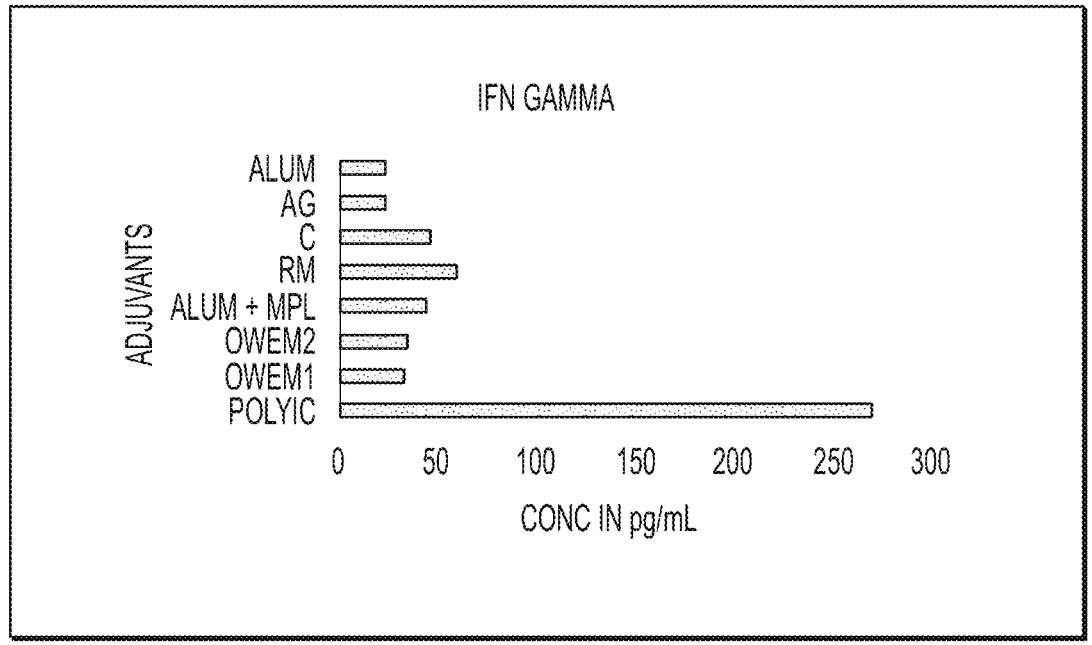

FIG. 11A: Estimation of Th1 cytokine, IFN gamma, in mice vaccinated with Zika vaccine formulations with different adjuvants.

Figure 11B:
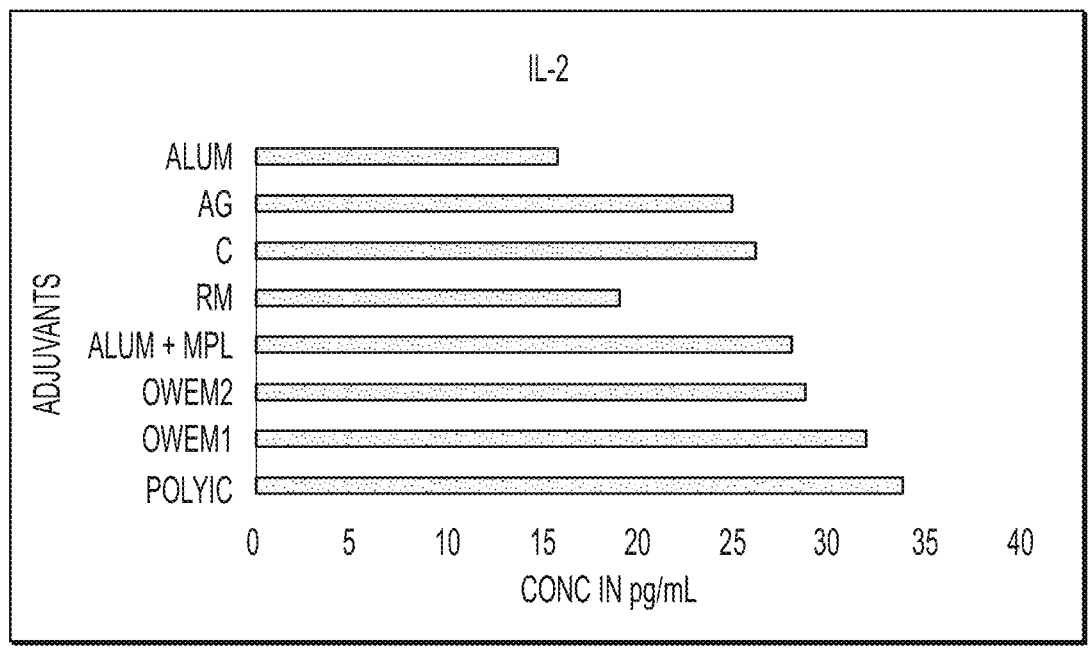

FIG. 11B: Estimation of Th1 cytokine, IL-2, in mice vaccinated with Zika vaccine formulations with different adjuvants.

In all cases, in FIG. 11A and FIG. 11B, it was 10 µg of vaccine antigen per dose. Adjuvants are abbreviated as follows: pIC (polyIC); C—cholecalciferol; MPL (lipid A; monophosphoryl); RP (resiquimod+polyIC); RM (resiquimod+OWEM2); I (inulin); OWEM2 (oil in water emulsion 2); AI (aluminum hydroxide+inulin); MDP (muramyl di peptide); OWEM1 (oil in water emulsion 1) as described in Example 5. Oil based adjuvants and polyIC elicited a strong Th1 response compared to other adjuvants tested.

Figure 12A:
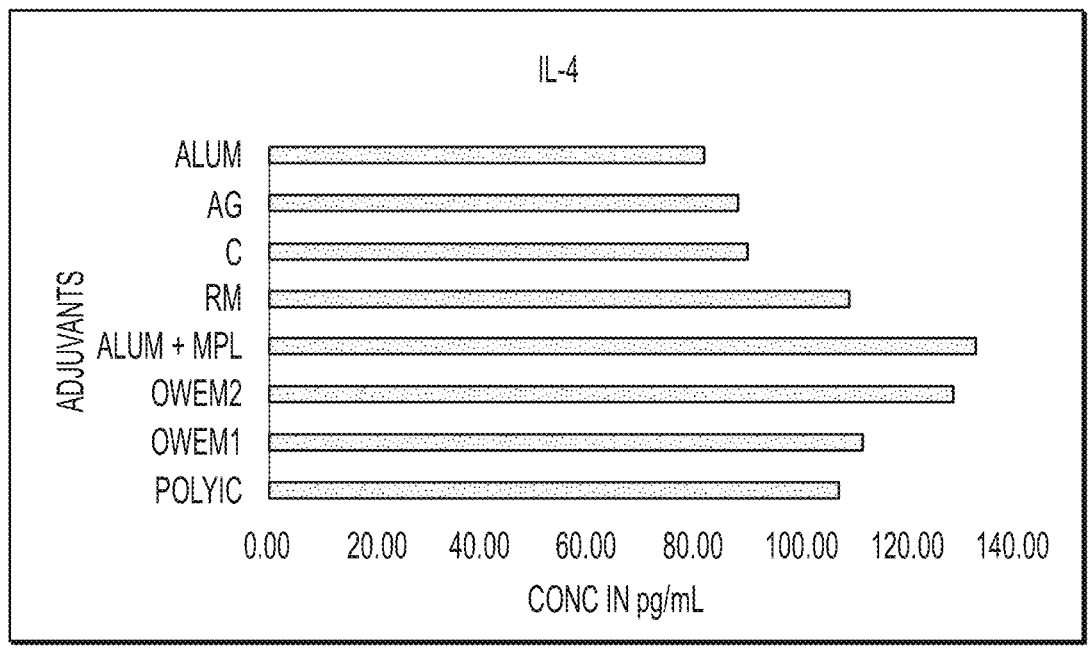

FIG. 12A: Estimation of Th2 cytokine, IL-4, in mice vaccinated with Zika vaccine formulations with different adjuvants.

Figure 12B:
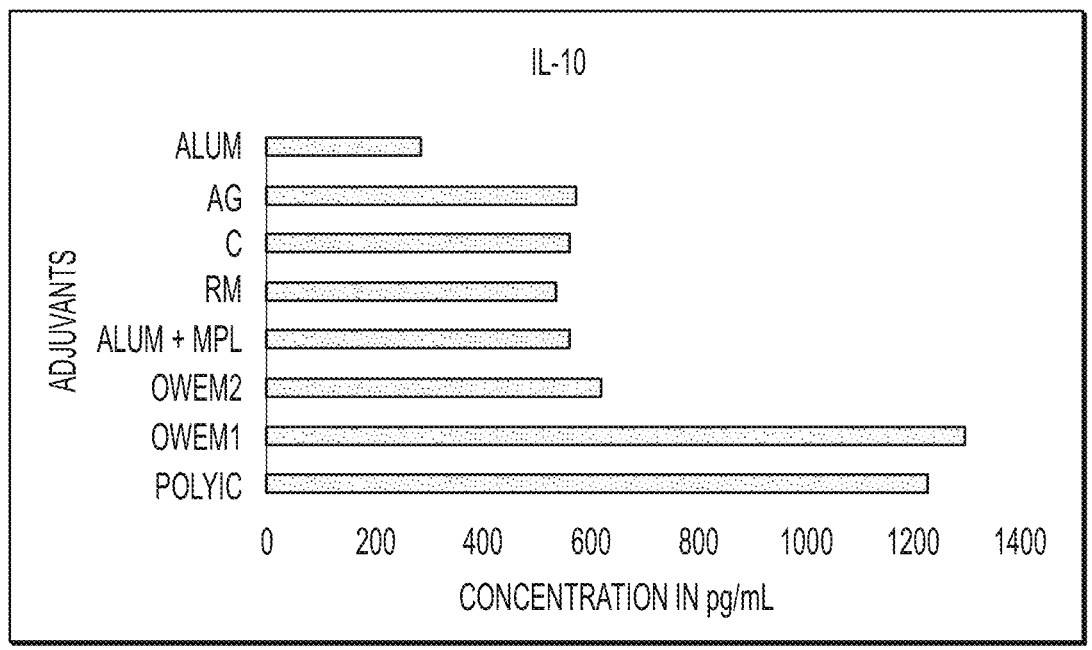

FIG. 12B: Estimation of Th2 cytokine, IL-10, in mice vaccinated with Zika vaccine formulations with different adjuvants.

In all cases, in FIG. 12A and FIG. 12B, it was 10 µg of vaccine antigen per dose. Adjuvants are abbreviated as follows: pIC (polyIC); C—cholecalciferol; MPL (lipid A; monophosphoryl); RP (resiquimod+polyIC); RM (resiquimod+OWEM2); I (inulin); OWEM2 (oil in water emulsion 2); AI (aluminum hydroxide+inulin); MDP (muramyl di peptide); OWEM1 (oil in water emulsion 1) as described in Example 5. Oil based adjuvants and polyIC elicited strong Th2 response in addition to Th1 response.

DETAILED DESCRIPTION OF THE INVENTION

This disclosure concerns formulation of vaccine compositions. The invention discloses in particular, preparation and formulation of vaccine antigens of Zika virus in monovalent compositions and in combination with other arboviruses such as Chikungunya and/or Japanese encephalitis viruses. In particular, the invention discloses compositions for prophylaxis and treatment of Zika virus infections.

One aspect of the invention is that the methods of preparation, formulation and use of Zika antigens as vaccine for eliciting immune response is applicable to any genotype, genotypic variants or any strain of Zika virus wherein one genotype of Zika virus cross neutralizes a heterologous strain efficiently. The Zika virus can be selected from Asian, West African or East African genotype of the virus. Therefore, the methods described in the current invention herein are applicable to Zika virus of any genotype/strain, live attenuated Zika virus, deactivated virus, virus like particles, chimeric virus particles that carry any Zika virus antigens particularly the E protein and the M protein in any heterologous virus backbone, in vectored vaccines and infectious synthetic virus particles derived in vitro or in vivo using the sequence of any Zika virus genome. A chimeric virus has the nucleic acid of a heterologous virus and nucleic acid of Zika virus.

In the context of the immunogenic compositions disclosed herein, in particular the bulk antigen used for preparation of immunogenic compositions, the methods of preparation, formulations and use of Zika vaccine antigens are applicable to any of the aforementioned Zika virus types, that share at least 50% amino acid identity and up to 100% amino acid identity across any region of the genome. In the context of the immunogenic compositions disclosed herein, sequence of Zika virus MR766 strain of African genotype (SEQ ID NO:5 for genomic nucleotide sequence and SEQ ID NO:6 for complete ORF) shares more than 96.5% amino acid identity in the structural Envelope protein with the Asian genotype strain FSS13025 and whose sequence is disclosed in SEQ ID NO:7 and SEQ ID NO:8 for the nucleotide and protein sequences respectively. Vaccine antisera of the MR766 strain cross neutralized the FSS13025 strain with 100% equivalent potency as the homotypic MR766 strain. Also in the context of the disclosure herein, Zika virus prME (SEQ ID NO:3) antisera efficiently cross neutralized the MR766 strain confirming that all Zika viruses are serotypically similar. In the context of the disclosure herein, the vaccine methods developed using any one of the Zika virus strains is applicable to homologous and any heterologous Zika virus strains for use as candidate vaccine.

A cell line that can be propagated in vitro in culture can be used as a host for Zika virus culture. For propagating Zika virus strains, preferably permissive cells which allow the virus to grow well are selected. For example, diploid cell lines such as MRC-5 and WI-38, and serially passaged cell lines such as Vero, BHK-21, CHO cells etc. can be used. For example, Vero cells (ATCC No. CCL-81), BHK-21 (ATCC No. CCL-10), C6/C3 (ATCC No. CRL-1660) etc. can be used. In a preferred embodiment, one such cell line used in the current invention is Vero cells (ATCC No. CCL-81) which has been validated for use as a host cell for vaccine production. The validated Vero cell lines conforms to the Requirements for Biological Substances No. 50 regarding requirements for use of cells for the production of biologicals recommended by the World Health Organization (WHO) thereby confirming these cell lines as qualified for producing a vaccine (WHO Technical Report Series, No. 878, pp 19-52, 1998).

In one aspect of the invention, the method of adaptation of Zika virus to Vero cells increases the virus titer. Zika virus passaged repeatedly in Vero cells increases the virus titer. In the context of virus growth in Vero cells disclosed herein, Zika virus passaged initially in mouse brain or *Ae. albopictus* C6/36 cells (ATCC No. CRL-160) and then adapted to Vero cells increases virus titers suitable for vaccine production.

For maintenance in cell culture of the above-mentioned cell lines, Vero cells in particular, stationary culture in monolayers, perfusion system culture, shake flasks, roller tube/bottle culture, suspension culture with and without microcarriers, cell factories and cell stacks, bioreactors and disposable bioreactors, wave bioreactors and the like can be adopted. For example, various types of microcarriers are commercially available. Commercially available animal cell culture devices can be used to facilitate the growth of cells to high cell density.

In one aspect of the invention and disclosed herein, the Zika virus is purified for use as candidate vaccine. Purification is achieved by a combination of both physical and chemical methods either before or after inactivation of the virus. Physical methods include any of the following techniques but not limited to: ultracentrifugation, density gradient centrifugation, ultrafiltration, diafiltration and concentration using semi-permeable membranes with suitable molecular cut-off sizes. Purification through chemical means employs methods such as adsorption/desorption through chemical or physiochemical reactions such as ion exchange chromatography, affinity chromatography, hydrophobic interaction chromatography, gel filtration chromatography such as for example Captocore700™, hydroxyapatite matrix, salting with inorganic salts, one such example being ammonium sulphate.

In a preferred embodiment, the virus is purified on Capto core 700 (GE Healthcare Life Sciences) column chromatography. Inactivation of the virus is achieved either before purification or after purification on Capto core 700 column. The virus harvest before Capto core 700 column can be clarified using membrane filters with different pore sizes, preferably not less than 0.45 µM low protein binding membrane. In a preferred embodiment, the virus harvest can be clarified with a dual membrane of two different pore sizes, for example 1.2 µM followed by 0.45 µM, or 0.8 µM followed by 0.45 µM. The clarified virus harvest is suitable for purification on Capto Core 700 column. The buffers used for purification on Capto core 700 is of optimal pH and ionic strength to maximize the binding of the impurities on the column and elute the virus in the flow through. The virus sample is further concentrated by diafiltration before or after virus inactivation. Diafiltration of the virus sample after inactivation removes the virus inactivating agent from the bulk antigen, and is suitable for formulation.

In one embodiment of the invention, Zika virus in inactivated (killed) for use as a vaccine antigen. Inactivation can be carried out either before or after purification of the virus. In a preferred embodiment, inactivation of Zika virus is carried out after purification of the virus.

Zika virus can be inactivated either by heat, gamma irradiation, ultraviolet light or by chemical means. In a preferred embodiment disclosed herein, Zika virus is chemically inactivated. Chemical inactivating agents were selected from the following list which includes but is not limited to: formalin, beta-propiolactone, glutaraldehyde, N-acetylethyleneimine, binary ethyleneimine, tertiary ethyleneimine, ascorbic acid, caprylic acid, psolarens, detergents including non-ionic detergents etc. wherein the chemical inactivating agent is added to a virus suspension to inactivate the virus.

In a preferred embodiment of the invention, the chemical inactivating agent selected is formalin and/or beta propiolactone (BPL). Formalin is used at any concentration ranging from 1:1000 to 1:4000 v/v of formalin:virus. Beta propiolactone is used at any concentration ranging from 1:1000 to 1:4000 v/v of BPL:virus. The temperature and duration of inactivation is optimized to complete virus inactivation with minimal adverse effect on immunogenicity. This can be achieved with shorter duration of exposure with minimum quantity of the inactivating agent. In the context of virus inactivation, the disclosure herein describes the concentration, temperature and time of exposure of Zika virus to formalin and BPL. In the preferred embodiment of the invention, the inactivation temperature is 25±3° C., most preferably 22° C. for 7 days. At lower temperatures of 2° C. to 8° C., the duration of formalin exposure is longer than 7 days to achieve complete virus inactivation at the aforementioned concentration ranges. Duration of virus exposure to formalin can be reduced to below 48 hours by increasing the temperature of exposure up to 37° C. Hence, effective formalin inactivation of Zika virus can be achieved at any concentration range of formalin from 1:1000 v/v formalin:virus up to 1:4000 v/v formalin:virus by choosing any temperature range from 2° C. to 37° C. and varying the exposure time from 24 hours to more than 10 days at any of the aforementioned concentrations, time and temperature of exposure.

In one embodiment of the disclosure, BPL is used as virus inactivating agent for Zika virus. In a preferred embodiment of the invention, BPL is used at concentrations ranging from 1:1000 v/v BPL:virus up to 1:4000 v/v BPL:virus. At lower temperatures of 2 to 8° C., the duration of BPL exposure is preferred for 3 to 7 days to achieve complete virus inactivation at the aforementioned concentration ranges. Duration of virus exposure to BPL can be reduced to 48 hours or below by increasing the temperature of exposure up to 25±3° C. or even up to 37° C. Hence, effective BPL inactivation of Zika virus can be achieved by choosing any concentration range of BPL from 1:1000 v/v BPL:virus to 1:4000 v/v BPL:virus by choosing any temperature range from 2 to 37° C. and varying the exposure time from 24 hours to more than 10 days at any of the aforementioned concentrations, time and temperature of exposure.

One of embodiments of the current invention disclosed herein is the use of a combination of BPL and formalin at any of the aforementioned conditions, preferably BPL inactivation at 1:3000 v/v of BPL:virus for 24 hours followed by formalin inactivation at 1:3000 v/v formalin:virus for 24 to 48 hours at 15° C. to 30° C., preferably 25±3° C. The use of BPL and formalin combination for Zika virus inactivation is that the mechanism of inactivation being different for formalin and BPL, their combined use reduces their overall concentration and exposure to both the inactivating agents, and also the use of low concentrations of formalin promotes stability of the virus bulk by promoting cross linking of virus epitopes. In another embodiment of the invention, hydrogen peroxide is used for inactivating the Zika virus at concentrations ranging from 0.1 to 3%, preferably 0.1 to 1% at any temperature from 20° C. to 30° C. for 5 to 120 minutes, if not more.

An embodiment of the current invention discloses the use of the prME (pre-membrane and the Envelope protein) of Zika virus as the candidate vaccine antigen to elicit immune response against the Zika virus. The disclosure is applicable to any method of vaccine design wherein the prME or the E protein is expressed in such a manner that the neutralizing Zika antibodies are directed against the said antigens. In a preferred embodiment of the invention, the prME protein is expressed as recombinant virus like particles (VLP) in baculovirus mediated expression in insect cells. Anyone skilled in the art will derive additional embodiments using the above disclosure to design a vaccine candidate using the prME protein as the target Zika antigen such as a DNA vaccine, Virus like particles comprising prME proteins, subunit vaccine comprising the Envelope (E) antigen, live vectored vaccines, chimeric vaccines using the Zika prME on a heterologous nucleic acid backbone wherein in all the above, the anti-Zika antibodies are largely directly against the E protein.

In the current invention disclosed herein, are immunogenic compositions comprising purified recombinant Zika virus antigens comprising the envelope (E) protein, membrane (M) protein and optionally the non-structural 1 (NS1) protein as vaccine antigens for eliciting immune response for prophylaxis of Zika virus infections. In a preferred embodiment, the use of the Zika virus having of the prME gene of sequences SEQ ID NO:1 and SEQ ID NO:2 encoding the structural protein of SEQ ID NO:3 and SEQ ID NO:4 respectively, wherein the expressed and purified prME protein can be used as vaccine antigen for prophylaxis of Zika virus infections.

In a preferred embodiment, Zika virus prME gene is used to generate a recombinant gene construct that can be used to express the prME protein in prokaryotic or eukaryotic expression systems as virus like particles (VLPs), preferably baculovirus mediated expression in insect cells. The methods disclosed herein are applicable to any Zika virus strain that share at least 70% amino acid identity to the aforementioned SEQ ID NO:3 and SEQ ID NO:4

An embodiment of the current disclosure is the choice of pharmaceutically acceptable buffer throughout the bioprocess wherein the buffering agent is selected from a list consisting of any one or more of the following, but not limited to: phosphate buffer; citrate buffer; phosphate citrate buffer; borate buffer; tris(hydroxymethyl)aminomethane (Tris) containing buffer; succinate buffer; buffers containing glycine or histidine as one of the buffering agents. In the most preferred embodiment, phosphate buffer is used, wherein phosphate buffer is sodium phosphate buffer at concentration of 5 mM up to 200 mM of phosphate ions, preferably 10 mM to 100 mM phosphate buffer, most preferably 10 mM to 50 mM phosphate buffer of any pH above 6.50 to pH 9, preferably pH 6.8 to pH 7.8 is used for the upstream and downstream processes. In a preferred embodiment, 10 mM sodium phosphate buffer of pH 7.4±0.2 is used in the preparation of the purified inactivated vaccine bulk of Zika virus antigen, and optionally containing sodium chloride at a concentration from 50 to 200 mM. In another preferred embodiment, sorbitol and L-glycine are optionally added to a final concentration of 1% and 0.5% respectively.

An embodiment of the current invention also discloses the choice of adjuvants that is compatible for formulation with Zika virus antigen.

The antigenic compositions of Zika virus as monovalent vaccine, and with Chikungunya virus and Japanese encephalitis viruses in combination vaccine were formulated in pharmaceutically acceptable carrier for immunization. The use of adjuvant(s) can reduce the amount of antigen required in the formulation Furthermore, for adjuvanted vaccine formulations, suitable adjuvant(s) were selected from the following list, which includes but is not limited to: alum such as aluminum hydroxide, aluminum phosphate, or amorphous aluminum sulphate phosphate; calcium phosphate; inulin of any polymorphic form, preferably gamma inulin;

adjuvants containing inulin in combination with other organic and inorganic compounds such as aluminum hydroxide, aluminum phosphate, aluminum sulphate phosphate and calcium phosphate; liposomes, chitosan and complex carbohydrates such as dextran, dextrins, starch, mannans and glucomannans, galactomannans, beta-glucans, heparin, cellulose, hemicellulose, pectins and pectinates, lectins and any other carbohydrates either synthetic or derived from any source, any biodegradable and biocompatible polymers, such as poly lactide and polylactide co-glycolides, (PLG or PLGA); any emulsions including but not limited to oil in water emulsions one such example being squalene or squalene analogues containing oil in water adjuvants, oil in water emulsions containing vegetable oils; any water in oil emulsion; liposomes prepared with cholecalciferol as one of the ingredients along with other lipid soluble compounds; liposomes of other compositions; RIBI adjuvant systems, saponins including but not limited to QS-21, QuilA, tomatine, ISCOMs, ISCOMATRIX etc, lipopeptides, glycopeptides and their analogues, resiquimoid, lipopolysaccharides, lipid A, muramyl dipeptides or their analogues and any peptide based adjuvants, oligonucleotides, any TLR ligands and their analogues as adjuvants, any cytokine, vitamins and non-toxic bacterial toxins, indeed any analogues of all the aforementioned adjuvants and combination of two or more of the aforementioned adjuvants or their analogues that are compatible in vaccine formulation(s). and tested for enhanced immunogenicity. In addition to the above, any other organic and inorganic substances that have good immunopotentiating activity are suitable to be used as adjuvant either singly or in adjuvant combinations to enhance the immunogenicity of the arboviral antigens. The use of adjuvant in the vaccine formulations can reduce the amount of antigen required.

In a preferred embodiment of the invention, aluminum hydroxide was used for dose ranging studies of both formalin and BPL inactivated Zika antigens as well in vaccine combinations of Zika, CHIKV and JEV vaccines due its safety profile for use in target population. Oil based emulsions and polyIC gave good immunopotentiating effect to Zika antigen when used as adjuvants. In one embodiment of invention, polyIC and other adjuvants that offer both systemic mucosal immunity is particularly advantageous for protection against disease caused by Zika virus infections. PolyIC and the oil based emulsions and the adjuvant combinations disclosed in the invention elicited both Th1 and Th2 responses estimated by the measurement of the Th1 and Th2 cytokines after vaccination. Several of the above mentioned adjuvants also elicit strong mucosal immunity in addition to systemic immunity, one such example being polyIC. Zika vaccine antigens either the inactivated or purified recombinant prME proteins are formulated with any of the adjuvants that elicit both systemic and mucosal immunity.

In one embodiment of the current invention, a vaccine preservative is used in the vaccine formulations. The preferred embodiment is 2-phenoxy ethanol at a concentration of 2.5 to 5 mg per dose 2.5 to 5 mg per mL In one aspect of the current invention disclosed herein are the use of stabilizing agents selected from one or more of the following, but not limited to: lactose, sucrose, trehalose, maltose, mannose, iso-maltose, raffinose, stachyose, lactobiose, sorbitol, mannitol, lactobionic acid, dextran, L-glycine, L-histidine, L-glutamic acid, L-aspartic acid, human serum albumin and combinations thereof, at any suitable concentration that are used to confer stability during the inactivation of Zika virus by any of the aforementioned methods. In a preferred embodiment, the stabilizing agents are selected from any of the following combinations but not limited to: 2% sorbitol and 1% L-glycine; 1% sorbitol and 0.5% L-glycine; 1% mannitol and 0.5% L-glycine; 1% mannitol and 0.5% L-glutamic acid; 1% sorbitol, 0.5% L-glycine, 1% human serum albumin. In a preferred embodiment, the combination of 1% sorbitol and 0.5% L-glycine and 1% mannitol and 0.5% L-glycine are preferred combinations, most preferably, 1% sorbitol and 0.5% L-glycine. One skilled in the art will recognize further embodiments based on the above disclosures.

Lyophilized formulations are one of the methods for preparation of vaccine product. Lyophilized preparations of Zika virus vaccine typically contain purified inactivated Zika virus, a sugar polyol, preferably sorbitol and mannitol, most preferably sorbitol in combination with a glass forming sugar, which is preferably a disaccharide or an oligosaccharide. The preferred disaccharide is selected from the following list but is not limited to: sucrose, trehalose, maltose, mannose, lactose, raffinose, isomaltose, stachyose etc. the preferred embodiment of the disclosure is a combination of 1% sorbitol with 5% sucrose, 1% mannitol with 5% sucrose, and 3% sucrose and 2% trehalose, 1% mannitol with 1% L-glycine and or 2% trehalose. Any one of the ordinary skill in the art will devise further embodiments and based on the disclosures above.

The lyophilized formulations can be re-suspended in water for injection or an aqueous buffer that is pharmaceutically acceptable for administration. e.g. as an injectable liquid to a human subject. The lyophilized formulation can also be used as an inhalable powder which will be suitable for inducing mucosal immunity. Additionally, the lyophilized formulation of Zika virus can comprise an adjuvant that confers mucosal immunity preferably from a list of those adjuvants tested in the current invention for Zika virus such as polyIC for example.

In the current invention, the disclosure provided herein on the optimal use of Zika virus antigen to elicit robust immune response, the vaccine antigen can be used at 0.10 µg up to 100 µg per dose, wherein the preferred embodiment is any concentration from 0.125 µg up to 40 µg per dose such that the administered vaccine doses elicit antibody titers measurable by assays such as ELISA and $PRNT_{50}$. The vaccine can be administered with and without an adjuvant as both the inactivated vaccine and the adjuvanted formulations elicit good immune response.

In yet another disclosure of the invention, the inactivated Zika vaccine candidate inactivated by any of the disclosed methods can be administered as a single dose or in two or more doses to elicit immune response. The methods disclosed in the invention provide the kinetics of immune response after each dose of the vaccine, at dose ranges from 0.125 µg up to 40 µg per dose that offers the flexibility of the choice of the vaccine dose range concentrations and number of doses to suit the target population for vaccination.

The route of vaccine administration can be by any route selected from, but not limited to intramuscular, intradermal, subcutaneous, intravenous, oral, intranasal and transcutaneous routes. In a preferred embodiment of the invention, the preferred route of vaccine administration is intramuscular (IM) route.

The vaccine formulations can be presented in glass vials and injected by needle and syringes, presented in pre-filled syringes in a ready to use presentation or administered by electroporation, microneedle patches, needle free patch, by inhalation or by nasal sprays.

The current invention discloses methods for preparation and use of formulations comprising one or more arbovirus antigens selected from a list that includes Zika virus, Chikungunya virus (CHIKV), and Japanese encephalitis virus (JEV). When used in vaccine combination, the vaccine can elicit immune response against each of the viruses present in a combination vaccine. In a preferred embodiment of the invention comprising a vaccine composition wherein Zika virus antigens and Japanese encephalitis virus antigens are present in a combination vaccine at concentrations ranging from 5 µg to 50 µg of each antigen in a pharmaceutically acceptable formulation without an adjuvant, or preferably with an adjuvant selected from the list of adjuvants disclosed in the current invention, preferably aluminum hydroxide with 0.25 mg to 1.5 mg of aluminum content per vaccine dose is disclosed. In yet another preferred embodiment of the invention a vaccine composition comprising Chikungunya and Zika virus antigens in a formulation comprising 5 µg to 50 µg of each antigen in a pharmaceutically acceptable formulation without an adjuvant, or preferably with an adjuvant selected from the list of adjuvants disclosed in the current invention, preferably aluminum hydroxide with 0.25 mg to 1.5 mg of aluminum content per vaccine dose is disclosed.

In yet another preferred embodiment of the invention, a vaccine composition comprising Chikungunya, Zika and JEV virus antigens in a formulation comprising 5 µg to 50 µg of each antigen in a pharmaceutically acceptable formulation without an adjuvant, or preferably with an adjuvant selected from the list of adjuvants disclosed in the current invention, preferably aluminum hydroxide with 0.25 mg to 1.5 mg of aluminum content per vaccine dose is disclosed. The use of vaccine combination confers a distinct economical advantage for manufacture and distribution of vaccines, provided that immune response is elicited against each of the antigen in the formulation and no antigenic interference is observed to either of the antigen by the presence of an additional antigen. The vaccine antigens can either be administered from a single formulation or administered separately at the same time or in suitable time intervals so as to elicit an immune response to the cognate antigen. The recombinant Zika prME protein can be used in vaccine combination with inactivated JE and CHIKV vaccines in lieu of inactivated Zika virus vaccine.

Recombinant CHIKV VLP obtained by expressing the structural polyprotein of CHIKV comprising largely of the capsid, E2 and E1 and 6K proteins or E2, E1 and 6K polypeptides or E2 and E1 can be used in combination with inactivated Zika and JE vaccines as a combination.

The current invention also discloses the use of Zika virus antibodies for detection of Zika virus by ELISA or in any immunodiagnostic methods where the antibodies find an application for detection or diagnosis of Zika virus infections.

The current invention also discloses herein the use of Zika virus antibodies for prevention and treatment of Zika virus disease.

Abbreviations used in the invention: IM—intramuscular; mcg-microgram; TCID50-50% Tissue Culture Infectious Dose; PFU—Plaque forming unit

EXAMPLES

Example 1: Zika Virus Culture in Vero Cells

Vero cell line (ATCC No. CCL-81) was used as the cell substrate for culture of Zika virus.

Extensively characterized Vero cells obtained from BioReliance, USA was used in pilot scale production. Vero cells were grown in DMEM (Dulbecco's Modified Eagle Medium; Sigma-Aldrich Catalog #D5523 and used as per the manufacturer's instructions) or EMEM (Eagles Minimal Essential Medium) containing 5% fetal bovine serum (FBS) or New Born Calf Serum (NBCS) and incubated at 35° C. to 37° C. until reaching 80-100% confluence of the monolayer. Post-infection, the same medium containing 1% serum was used, or alternatively the virus was cultured in Vero cells adapted to serum free medium. Zika virus also could be grown in MRC-5 cell monolayer which were prepared in growth medium consisting of EMEM buffered to neutral pH with Hepes buffer with 5% serum and statically incubated at 35° C. to 37° C. for 6 to 8 days. Zika virus was cultured routinely in Vero cells. Zika virus MR766 strain (ATCC VR-84) procured from LGC Promochem, Bangalore was adapted to Vero cells by direct inoculation in Vero cells. Alternatively, the virus was adapted in C6/36 *Ae. albopictus* cells twice by serial passages, and the Zika virus in culture supernatant from these cells was used to infect Vero cells. Serial passage of Zika virus in C6/36 cells cultured at 25° C. to 28° C. increased the virus titer higher than 10e8.0 $TCID_{50}$/mL or 10e8.0 PFU/mL. This also obviated the need for subsequent repeat passages in Vero cells to obtain high titers. Virus adaptation by this method is useful to achieve high titers and subsequent higher yield in production. After culture in C6/36 cells, the virus was serially plaque purified twice from Vero cells, and the virus from a single well isolated plaque was amplified and extensively characterized to be free of adventitious agents (all known RNA and DNA viruses, bacteria, fungi, *mycoplasma* etc) using the NGS (Next Generation Sequencing) platform. The virus genomic RNA was sequenced by NGS platform, and complete nucleotide sequence of MR766 strain is provided in SEQ ID NO:5 and the corresponding deduced amino acid sequence is provided in SEQ ID NO:6. Sequencing showed the intact glycosylation site in the Envelope protein, which otherwise is lost if the cells are extensively passaged in mammalian cells. Zika virus produces cytopathic effect (CPE) in Vero cells, and at the optimal Multiplicity of Infection (MoI) and harvest conditions, virus titers above 10e8.5 TCID50/mL or 10e8.5 PFU/mL could be attained.

Example 2: Zika Virus Purification

For Zika virus culture at pilot scale, the virus culture was systematically scaled up from T-175 flasks to CS1 (cell stack 1), CS10 (cell stack 10) and CS40 (cell stack 40). Multiples of CS40 simultaneously infected with the virus at standardized MoI was used to scale up production. Use of multiples of CS40 enables quick and linear scale up to the desired volumes of production. The harvest volume from each CS40 was approximately 8-10 L. The virus was harvested at days 4-6 or whenever more than 90% CPE was achieved. Alternatively, disposable bioreactors under well standardized conditions of temperature 35° C. to 37° C., pH not less than 7.0, and optimally at pH 7.4, dissolved oxygen at 45 to 75 ppm, preferably 60 rpm and an agitation of 240 to 280 rpm and optimally controlled in-flow and out-flow rate optimized according to the scale of the culture volume from 1 L to 100

L was used to increase the cell density and virus harvest. The viral harvest was clarified either by microfiltration or using dual filters with cut off of 1.2 µM and 0.45 µM. The clarified viral harvest was then passed through Capto Core700 column (GE healthcare Life Sciences) in phosphate buffered saline, pH 7.4. The Zika virus containing fractions in the flow through was optionally concentrated by diafiltration using either 100 kDa or 300 kDa cut off membranes. The concentrated virus fraction was used for virus inactivation. In an alternate method, the clarified viral harvest was inactivated with either BPL or formalin according the methods described in the succeeding sections and then loaded on the column. The purity of the virus was checked on 12.5% SDS-PAGE. There was no significant difference in the yield or in purity in inactivating the virus before and after purification. The virus could also be purified using cellufine sulphate, DEAE-Sephadex CM-sephadex with salt gradient and by gel filtration on Sepharose CL-4B, ceramic hydroxyapatite column with gradient of 0.2M to 0.8M phosphate and in all cases followed by diafiltration using 100 or 300 kDa cut off membranes. The purity of the virus preparation was checked by silver staining of the virus sample in 12.5% of SDS-PAGE gel (See FIG. 1). Zika virus by the aforementioned methods could be purified to high purity suitable to be used as vaccine bulk antigen. The virus could also be purified by ultracentrifugation on a 20-60% sucrose gradient using P28S rotor in Hitachi HIMAC ultracentrifuge after centrifugation at 100,000×g for 6 to 8 hours.

Example 3: Zika Virus Inactivation

Zika virus sample was inactivated (killed) by various methods for use as vaccine antigens. Formalin inactivation was tested at various concentrations ranging from 1:1000 (formalin:virus, v/v) to 1:4000 (formalin:virus, v/v) at temperature 25±5° C., more specifically at 22° C. and the kinetics of virus inactivation was monitored every 24 hours for up to 10 days, and routinely the virus inactivation was carried out at 25±3° C., preferably at 22° C. for 7 days. The virus inactivation was effective at all concentrations from 1:1000 v/v formalin:virus, up to 1:3500 v/v formalin:virus, at the aforementioned temperatures and time intervals. A ratio of 1:4000 v/v of formalin:virus was effective in virus inactivation at higher temperatures up to 30 to 37° C. for 3 to 7 days. Formalin inactivation was effective at all the aforementioned ratios of formalin to virus at temperatures ranging from 2-8° C. when incubated for time intervals longer than 10 days. Hence formalin inactivation offers flexibility of virus inactivation at any temperature from 2° C. to 37° C. at time intervals ranging from 24 hours to more than 10 days depending upon the conditions used for inactivation. Zika virus inactivation with Beta propiolactone (BPL) was tested under various conditions. Zika virus was completely inactivated at BPL concentrations ranging from 1:1000 (BPL:virus, v/v) up to 1:3500 (BPL:virus, v/v) at temperatures from 25±5° C. for 24 to 48 hours. At higher concentration of BPL or at higher temperatures up to 37° C., complete inactivation was achieved in 24 hours or less, and can be used as a method for quick inactivation of the virus. Zika virus could also be inactivated at the aforementioned concentrations of BPL when incubated at 2 to 8° C. for 3 to 7 days. A combination of BPL inactivation at 1:3500 (BPL:virus, v/v) at 22-25° C. for 48 hours, followed by treatment with low concentrations of formalin from 1:3000 to 1:4000 v/v of formalin:virus for 24 hours was effective in both inactivating and stabilizing the virus. Any concentration of BPL and formalin could be used for both inactivation and stabilizing the virus, as long as inactivation is complete without deleterious effect on immunogenicity. Inactivation was tested from 0.005% up to 3% final concentration of Hydrogen peroxide at 20° C. to 25° C. for a period 2 hours. There was no deleterious effect on the immunogenicity of the virus at lower concentrations of hydrogen peroxide with very brief exposure times within minutes but was deleterious at prolonged concentrations at higher dose ranges tested. The inactivated virus samples after exposure to different time and dose concentrations were titered for infectious virus particles if any, by TCID50/mL from 5 minutes up to 6 hours at intervals of 5, 10, 20, 30 and 60 minutes and at 2, 4 and 6 hours. At higher concentrations, the virus was inactivated within seconds. At each time point, the reaction was stopped by addition of 10 U/mL of catalase that rapidly hydrolyses hydrogen peroxide. The optimum concentration for inactivation was 0.01% final for duration of 60 minutes or less as determined by titration for infectious particles by TCID50/mL and subsequent immunogenicity. Zika virus inactivation with hydrogen peroxide offers the flexibility of duration of exposure at different concentrations for different time points according to the concentration of virus particles in the sample.

The purified Zika virus sample was heat inactivated at temperatures 50° C. to 65° C. for up to 60 min. UV inactivation of the virus was carried out UV exposure at 254 nm for up to 120 minutes. Zika virus was inactivated by gamma irradiation by exposure from 20 kGy (Kilo Gray) up to 35 kGy from a $^{60}$Co source at the Gamma Agro Medical Processing Facility at Hyderabad. All the above inactivation methods were carried out in the presence and absence of virus stabilizing agents such as various concentrations of sugars such as sucrose, lactose, trehalose, maltose, mannose among others. The sugar alcohols used for conferring stabilizing effect were sorbitol and mannitol. The amino acids tested were selected from L-Histidine, L-Glutamic acid, L-Glycine and L-Aspartic acid and L-Glutamine and also human serum albumin and a combination of one or more of the aforementioned stabilizing agents. The most effective stabilizing agents were sorbitol at 0.5% to 2%, preferably 1.0% in combination with L-Glycine from 0.5% to 2%, preferably at 0.5%. Mannitol and L-glycine in combination was effective in stabilizing the virus sample during inactivation rather than Mannitol and L-glycine alone.

The Zika virus samples inactivated by all the aforementioned methods for use vaccine antigens were tested for completeness of inactivation by serially passaging the inactivated samples three times serially in Vero cells and testing for infectious virus at the end of inactivation period by TCID$_{50}$. In addition to that, the inactivated virus sample after three serial passages in vitro was injected intracranially in 2-day old mice and observed for mortality or growth abnormalities for 21 days and considered completely inactivated when it showed no adverse effects in vitro and in vivo testing. No infectivity was observed with the formalin and beta-propiolactone inactivated virions at the aforementioned range of concentrations and for the various time periods tested. The inactivation kinetics of Zika virus by formalin and BPL as a representative example of one of the methods disclosed above is provided in FIG. 2 (FIG. 2A and FIG. 2B)

Example 4: Recombinant Cloning and Expression of Zika Virus pRME Protein

Synthetic gene of the nucleotide sequence SEQ ID NO:1 encoding the Open Reading Frame (ORF) of the prME protein of SEQ ID NO:3 of Zika virus was synthesized at GenScript, NJ, USA. The gene was PCR amplified with the primers listed below to obtain a ~2.1 kb fragment of SEQ ID NO:1 encoding the prME protein of SEQ ID NO:3. See FIG. 3A.

```
FVFP: 5'AACTGCTCGAGGAATTCGGATCCAAC 3'

FVRP: 5' AATGGGCATGCCTGCAGGCGGCCGCTC 3'
```

The PCR amplified fragments was digested with EcoR1 and Not1 restriction enzymes and cloned into the EcoR1 and Not1 sites of the pFastBac plasmid vector (Life Technologies, Carlsbad, Calif., USA) under the control of the polyhedron promoter by the methods described in the User's manual of Bac to Bac Baculovirus expression system ("An efficient site-specific transposition system to generate baculovirus for high-level expression of recombinant proteins, Life Technologies, USA). In brief, the method utilizes a site specific transposition of the expression cassette such as the recombinant pFastBac vector with the cloned inserts as described above into a baculovirus shuttle vector (bacmid) propagated in E. coli. Recombinant pFastBac vector containing one of the inserts SEQ ID NO:1 or SEQ ID NO:2 cloned under the control of the polyhedron promoter is transformed into competent cells of E. coli Max Efficiency DH10Bac™, that contains a baculovirus shuttle vector (bMON14272) and a helper plasmid (pMON7124) that facilitates transposition to allow efficient re-generation of the recombinant bacmid The recombinant bacmids were selected on ampicillin, gentamicin and kanamycin containing plates by blue/white selection using bluo-gal or X-gal, and IPTG. The recombinant bacmids after confirmation by PCR for the presence of the gene inserts was isolated by standard protocols described in the aforementioned User manual. About 1 µg of the bacmid DNA was used for transfection with Lipofectamine in Spodoptera frugiperda Sf9 insect cells (Life Technologies, Carlsbad, USA) grown in serum free insect cell medium. The methods used for transfection, isolation and titration of P1 viral stocks are exactly as described in the User's manual of Bac-to-Bac Baculovirus Expression system as given above. The P1 stocks were serially amplified twice to obtain high titer P3 stocks for expression of the recombinant prME proteins in Sf9 cells. High titer baculovirus stocks for expression of the prME protein of SEQ ID NO:3 was expressed in 25 mL suspension culture of Sf9 cells and was further scaled up systematically up to 125 mL per 500 mL flask. Baculovirus infected cells from multiple flasks were harvested at 72 hours post-infection, pooled, washed once with 1×PBS, pH 7.6 and lysed in cell lysis buffer containing 10 mM phosphate, pH 7.6 with 50 mM NaCl, 1 mM PMSF and 5 mM EDTA. The cell lysate was centrifuged at 20,000 rpm for 30 minutes to remove the cell debris and the supernatant was concentrated using protein concentrators with 10 kDa cut off membrane. The concentrated sample was layered on pre-equilibrated 20% to 60% sucrose gradient and centrifuged at 100,000×g for 6-8 hours using P28S rotor in Hitachi HIMACultracentrifuge Fractions containing the recombinant Membrane and Envelope protein was isolated and confirmed by Western blot (FIG. 3B) using the rabbit MR766 polyclonal antisera. The purified recombinant protein is of the sequence of the contemporary Asian genotype of Zika virus expressed using the gene sequence SEQ ID NO:1, encoded the protein of SEQ ID NO:3. The recombinant ME protein cross reacted with MR766 antibodies in Western blot and in ELISA and was formulated as vaccine antigen for testing in Balb/c mice as described in sections below.

Example 5: Vaccine Formulations

Zika virus vaccine antigen of any of the aforementioned methods in the preceding Examples was tested for immunogenicity in laboratory animals with and without adjuvants. High binding (>95%) was observed to aluminum hydroxide (Alhydrogel® 2%, Brenntag) as the adjuvant, used at the dose range of 0.1 mg to 1.5 mg of aluminum (provided as aluminum hydroxide) per dose even when tested at the high antigen dose of 40 mcg. Binding was complete at all the concentrations of Zika virus antigens as well as vaccine combinations with CHIKV and JE antigens discussed in the succeeding sections that were used for testing in mice. Binding to aluminum hydroxide was carried out for three hours at ambient temperature. An aliquot of the formulation was centrifuged at 5000×g for 5 min and the supernatant was tested for completeness of binding by antigen ELISA. The binding of the antigen was complete as it could not be detected in the supernatant by ELISA. The buffer for the adjuvanted formulations was 10 mM phosphate buffer, containing 154 mM NaCl, pH 7.40±0.2 and optionally containing 1% sorbitol and 0.5% L-Glycine. Other buffers used for specific formulations are mentioned below. The adjuvants listed below were tested for comparative immunogenicity and in all cases concentrations are provided per dose of the vaccine. Inactivated Zika virus antigen was tested at 10 µg per dose:

a) Inulin (Orafti-HPX, Beneo) was tested at 0.5 mg per dose; gamma inulin was prepared by the methods described in (Cooper and Steele, 1988)
b) A combination of aluminum hydroxide and inulin. A combination of inulin and aluminum hydroxide, algammulin was prepared at a ratio of 10:1 (10 mg/mL inulin: 1 mg/mL aluminum as aluminum hydroxide) was tested at 0.5 mg per dose
c) Muramyl di peptide (L18-MDP) (tlrl-Imdp, Invivogen) at 10 µg per dose
d) MPL (lipid A, monophosphoryl from Salmonella enterica, L-6895-1 MG, Sigma Aldrich) at 25 µg per dose
e) Combination of 0.25 mg aluminum (as aluminum hydroxide) and 25 µg of MPL per dose
f) Oil in water emulsion (OWEM1) containing 9.75 mg of squalene (53626-100ML, Sigma Aldrich), 11.86 mg of alpha-tocopherol (T3251-5G, Sigma Aldrich), 4.58 mg of Tween-80 (61771205001730, Merck) in 10 mM phosphate buffer, pH 7.4±0.2.
g) Oil in water emulsion 3 (OWEM2) containing 9.75 mg squalene, 1.175 mg of tween-80, 1.175 mg Span-85 (S7135-250ML, Sigma Aldrich) in 10 mM citrate buffer, pH 7.0
h) Poly IC (polyinosinic polycytidylic acid, potassium salt, Cat. NO. P9582-5MG, Sigma Aldrich) at 25 µg per dose
i) Cholecalciferol (Arachitol, Abbot) at 0.75 mg per dose
j) Resiquimod (SML0196-10MG, Sigma Aldrich)+Poly IC, 25 µg each
k) Resiquimod (25+Oil in water emulsion 2 containing 9.75 mg squalene, 1.175 mg of tween-80, 1.175 mg Span-85 (S7135-250ML, Sigma Aldrich) in 10 mM citrate buffer, pH 7.0
l) Aluminum 0.25 mg and 0.5 mg per dose provided as aluminum hydroxide All the above formulations elicited high level of neutralizing antibodies and the results are depicted in FIG. 4. The individual components of the aforementioned adjuvants and any of their analogues, derivatives, side chain substitutions and any modifications of any of the above components at varying concentrations can be used as non-toxic vaccine adjuvant components as long as they have immunopotentiating effect. Formalin inactivated and recombinant Zika vaccine antigens as described in the aforementioned sections each at a concentration of 10 µg per dose was lyophilized in combination with either of the following excipients: 1% mannitol and 0.5% Glycine, 5% sucrose and 1% trehalose, 5% sucrose and 1% maltose and 2% mannitol and 0.5% Glycine. The dry lyophilized formulation could be easily reconstituted in aqueous solution with water, normal saline and 10 mM phosphate buffered saline, pH 7.4±0.2. The stability of the formulation was tested at 37° C. for two weeks. No change in the cake characteristics was observed indicating the stability of the formulations. The moisture content was below 1%.

Example 6: Effect of Stabilizing Agents

The stability of the formalin inactivated vaccine bulk for use as non-adjuvanted vaccine antigen was tested for stability with the following concentration of stabilizing agents: a) 2% sorbitol and 1% L-glycine; b) 1% sorbitol and 0.5% L-glycine c) 1% mannitol and 0.5% L-glycine; d) 1% mannitol and 0.5% L-glutamic acid e) 1% sorbitol and 0.5% L-glycine, 1% human serum albumin. Stability testing was done at 37° C. for 2 weeks and the antigen concentration was tested by ELISA before and after exposure at 37° C. 1 μg and 10 μg of the non-adjuvanted formulation with 1% sorbitol and 0.5% L-Glycine was tested for immunogenicity in Balb/c mice as discussed in the succeeding sections.

Example 7: Potency Testing of Vaccine Formulations in Animal Models

Zika vaccine antigen inactivated by the aforementioned methods was tested in Balb/c mice in dose ranges from 0.125 μg up to 40 μg of antigen per dose with 0.25 mg aluminum per dose (as aluminum hydroxide) in a volume of 100 μL (injected in two sites at 50 μL per site) by intramuscular route on days 0, 14, 28. Initial testing on the effect of aluminum (provided as aluminum hydroxide showed that alum adsorbed vaccine gave higher titer of neutralizing antibodies than non-adjuvanted vaccine. About 1 and 10 μg of inactivated vaccine antigen without alum contained 1% sorbitol and 0.5% L-glycine as the excipients to confer stability to the vaccine antigens. Blood was drawn from retro-orbital sinus on days 13, 21 and 35 for estimation of neutralizing antibody titers by $PRNT_{50}$, total Ab titer by ELISA, Ab avidity and cytokine profiles. Blood withdrawal and testing after each dose gave data on the potency and safety of single, two doses and three doses of the vaccine preparations. The animals were each challenged on day 36 with 10e5 PFU of Zika virus by intravenous route. The blood samples were monitored for up to 7 days at 24 hour intervals for formalin groups and at two points at 48 hours and 96 hours for BPL inactivation groups for protection against viremia by $TCID_{50}$ (50% Tissue Culture Infectious Dose) and the virus titers if any, were expressed as $TCID_{50}$/mL. Animal challenge studies showed complete protection from viremia in 1 μg to 40 μg of the dose groups tested. Hence the BPL and formalin inactivated vaccine formulations were further tested at 0.5 μg, and at 0.25 μg 0.125 μg per dose by the IM route in Balb/c mice and were found to be immunogenic even at low dilutions. For the alum adjuvanted formulations, 0.25 mg of aluminum (as aluminum hydroxide) per dose was used as the placebo control and for non-adjuvanted formulations, 10 mM phosphate buffer containing 154 mM NaCl, 1% sorbitol and 0.5% L-Glycine, pH 7.40 was used as the vehicle control. All the formalin and BPL inactivated formulations elicited high level of neutralizing antibodies and protected against viremia as depicted in FIG. 5A, FIG. 5B and FIG. 6. Antigen only formulations also elicited high level of neutralizing antibodies and was protected from virus challenge. Recombinant prME protein expressed in insect cells was formulated at two doses of 10 and 20 μg per dose with 0.25 mg aluminum (as aluminum hydroxide) per dose in Balb/c (8 nos) and injected intramuscularly at day 0 and day 21 elicited neutralizing antibodies and the data is provided in Table 1. Gamma irradiated and Hydrogen peroxide inactivated Zika virus antigen at dose concentration of 10 μg and formulated with 0.25 mg aluminum (as aluminum hydroxide) per dose was injected by IM route in Balb/c mice at day 0 and day 21 and blood was withdrawn on day 28 for estimation of neutralizing antibodies by $PRNT_{50}$. Formalin inactivated virus antigen at 10 μg was formulated with each of the adjuvants disclosed in Example 5 and was injected intramuscularly in 4-6 week old Balb/c mice (5 nos per dose group) and the blood was drawn at 21 days after vaccine administration for estimation of neutralizing antibodies and cytokines. Control groups was included for each of the adjuvants and no neutralizing antibodies (<10 by $PRNT_{50}$) could be detected and the data is not shown. Neutralizing antibody titers by $PRNT_{50}$ of the different adjuvanted formulations, used pooled sera from each group is presented in FIG. 4. High level of neutralizing antibodies were elicited by the aforementioned adjuvanted formulations. It is pertinent to mention that antibodies to recombinant Zika prME, which is the sequence of the Asian genotype efficiently cross neutralize the MR766 strain of the African genotype. The titers are provided in Table 1.

A combination vaccine of arbovirus antigens were prepared a the following concentrations and tested in Balb/c mice: a) 10 μg formalin inactivated Zika virus antigen, 20 μg of BPL inactivated Chikungunya virus antigen and 6 μg of formalin inactivated JE antigen in a trivalent vaccine combination b) 10 μg formalin inactivated Zika virus antigen and 20 μg of BPL inactivated CHIKV virus antigen c) 10 μg of formalin inactivated Zika virus antigen and 6 μg of JE virus antigen. Zika virus was inactivated by 1:2500 of formalin: virus v/v by methods disclosed in Example 3. CHIKV was inactivated by 1:1500 of BPL:virus v/v, and JEV by 1:2500 v/v of formalin:virus and tested for completeness of virus inactivation by aforementioned procedures. All the above vaccine combinations were tested with 0.25 mg aluminum (as aluminum hydroxide) per dose in Balb/c mice (8 nos each) with appropriate controls that included either of the aforementioned antigens alone, and also control animals that received equivalent amount of alum. The animals were boosted at 14 and at 21 days after the first immunization. Blood was collected at 7 days after the last booster injection. The sera samples were used for estimation of neutralizing antibody by $PRNT_{50}$ for Zika, CHIKV and JEV. The buffer used in all the formulations was 10 mM phosphate buffer, pH 7.2 to 7.6 containing 154 mM NaCl. All the methods disclosed above are applicable to any genotype/genotypic variants/serotypes and strains of Chikungunya virus, Zika virus and Japanese encephalitis viruses. See Table 1 for the results.

TABLE 1

Neutralizing antibodies elicited by various antigenic formulations as disclosed in the Examples.

| Test Groups | Neutralizing antibody titers as Log10PRNT$_{50}$ | | |
|---|---|---|---|
| | Zika A | CHIKV | JE |
| Recombinant Zika prME - 10 µg × 2 doses | 2.8 | — | — |
| Recombinant Zika prME - 20 µg × 2 doses | 3.22 | — | — |
| Hydrogen peroxide inactivated Zika antigen - 10 µg × 2 doses | 2.6 | — | — |
| Gamma irradiated Zika antigen 10 µg × 2 doses | 2.71 | — | — |
| Zika alum adsorbed - 10 µg × 3 doses | 3.06 | — | — |
| Chikungunya alum adsorbed - 20 µg × 3 doses | — | 2.808 | — |
| JE alum adsorbed - 6 µg × 3 doses | — | — | 3.06 |
| Zika (10 µg) + CHIKV (20 µg) × 3 doses | 2.95 | 2.68 | — |
| Zika (10 µg) + JE (6 µg) × 3 doses | 2.80 | — | 3.28 |
| Zika (10 µg) + CHIKV (20 µg) + JE (6 µg) × 3 doses | 2.79 | 2.63 | 3.21 |

Table 1 Legend:

Purified recombinant prME antigen of Zika virus and the hydrogen peroxide inactivated and gamma irradiated Zika virus antigens formulated with 0.25 mg of aluminum per dose elicited neutralizing antibodies in Balb/c mice. The titers are expressed as Log 10PRNT50 values. The vaccine combinations elicited neutralizing antibodies when two or more antigens were administered in a single formulation, and no significant antigenic interference was observed between JE, Zika and CHIKV viruses. The titers were estimated in pooled sera samples from each group.

Example 8: Passive Immunization Studies

The proof of concept that neutralizing antibodies are important immune correlates of protection against Zika virus infection was demonstrated by single injection of rabbit polyclonal Zika antisera with known titer, about 200 µL of antisera diluted 1:1 with PBS was injected intraperitoneally in Balb/c mice and challenged 8-24 hours later with 10e5 PFU of Zika virus by intravenous route in a volume of 100 µL. Equal no. of control animals received PBS, pH 7.4 and received the virus injection as the test animals. Blood was collected at 24, 48, 72, 96 and 144 hours post virus challenge for detection of viremia in both the group of animals. Passive immunization offered complete protection against viremia and infectious virus could not be detected by TCID50. See FIG. 7. Viremia was detected in the control animals that persisted up to 6 days after virus challenge. Zika antibodies could be used as a therapeutic to ameliorate, eradicate or prevent Zika virus infections.

Example 9: Assays for Neutralizing Antibody Titers

Animal sera from all the aforementioned vaccine testing in mice described in Example 7 which include all the monovalent Zika vaccines inactivated with different inactivating agents and formulated with different adjuvants, vaccine antisera from dose ranging studies as well combination vaccines with CHIKV and JEV described in the preceding sections were assayed for neutralizing antibodies by 50% Plaque Reduction Neutralization Test (PRNT$_{50}$) by standardized procedures. Briefly, one day prior to the assay, 6-well plates were seeded with 2.5×10$^3$ Vero cells (ATCC CCL-81) per well and the plates were incubated at 37° C. in a 5% CO$_2$ incubator. To 4-fold dilutions of the sera samples in MEM containing equal volume of the standardized Zika virus strain (10$^5$ pfu/mL) was added and incubated at 37° C. with 5% CO$_2$ for 90 min. The cells were washed twice with 1×PBS pH 7.4 (10 mM phosphate with 150 mM NaCl) and 0.30 ml of each dilution of the serum-virus mixture was added to the corresponding well and incubated for 90 min at 37° C. in a 5% CO$_2$ incubator. Each assay was carried out in triplicates. The cells were overlaid with 2 ml of 0.85% methyl cellulose in MEM with 1% penicillin-streptomycin and 1% L-glutamine. The plates were incubated at 37° C. in a 5% CO$_2$ incubator for 4 days. At the end of incubation, the plaques were fixed with 10% formalin, washed with 1×PBS, pH 7.4 and were visualized with 0.1% crystal violet. The highest dilution of serum causing 50% reduction in the number of plaques formed by the control virus sample was estimated as the PRNT$_{50}$ titer. Anti-CHIKV and anti-JE antibodies from the vaccine combinations were also estimated PRNT50. All the aforementioned vaccine antigens elicited high level of neutralizing antibodies as depicted in FIGS. 5 and 6

Example 10: Zika Virus Cross Neutralization Studies

Formalin inactivated vaccine antisera cross neutralized the homologous MR766 virus strain of the African genotype and FSS13025 Zika virus strain (GenBank Acc No. JN860885) of the Asian genotype with EQUAL efficiency with PRNT50 titers of 18105 and 18325 against MR766 and FS13025 strains respectively. (The study BS-3018 was contracted to IBT Biosciences, Gaithersburg, Md., USA). Briefly, both the MR766 and the FS13025 Zika virus strains were diluted to ~250 PFU in serum-free medium. Both the vaccine antisera and control sera (placebo) were serially diluted in two-fold dilutions. The virus samples were mixed 1:1 with serially diluted sera samples and incubated at 37° C. for 2 hours. Vero cells seeded in 24-well plates were infected with the dilutions for 1 hour and 0.85% methyl cellulose was added to each well and incubated for 3 days. Cells were fixed and analyzed by plaque assay. The plates were scanned and the plaque counts were used to calculate the PRNT$_{50}$ titers using a 4PL curve fit. Hence the method of vaccine antigen preparation, formulation and testing are entirely applicable across any genotype of Zika virus as the vaccine with one genotype 100% cross neutralizes the heterologous strain and this also proves that no serotypes of Zika virus exists and that inactivated vaccine of Zika using any strain will be equally protective and potent as vaccine prepared using any genotype, and genotypic variant or indeed any Zika virus strain. This fact was further corroborated when the antibodies raised against the recombinant protein expressed as prME (protein of SEQ ID NO:3) in insect cells cross neutralized the MR766 virus with high efficiency. The protein of SEQ ID No. 3 is derived from the prME sequence of the Zika virus strain H/PF/013, which is the more contemporary strain of the Asian genotype. Cross neutralization of the vaccine antisera of the homologous MR766 strain of nucleotide SEQ ID NO:5 encoding the complete ORF of SEQ ID NO:6 and the heterologous FSS13025 of the SEQ ID NO:7 encoding the complete ORF of SEQ ID NO: 8 is depicted in FIG. 8A and FIG. 8B.

Example 11: Antibody ELISA

Briefly, Zika virus antigen was coated at the standardized concentration in coating buffer in 96-well plates overnight at 2 to 8° C. The plate contents were discarded and the wells were blocked with blocking buffer and washed extensively before adding the vaccine antisera at serial dilutions. Each vaccine antisera was assayed in triplicates. The plates were incubated for 90 min at 37° C., before adding secondary antibody (anti mouse-IgG HRPO conjugate) diluted 1:2500 in antibody diluent buffer. Each of the wells were washed five times with washing buffer (PBST, pH 7.4) and three times with PBS (pH 7.4), 30 seconds each. About 100 µl/well of freshly prepared substrate solution was added and incubated at ambient temperature for 10 minutes for color development. The color development was stopped by addition of 50 µL/well stop solution. Absorbance was read at 492 nm and the results recorded. For each assay, antigen blank, primary and secondary antibody blanks were included as controls. Seroconversion cut off value=pre-exposure average titer+(3x standard deviation). The end point dilution of positively seroconverted sample which shows a titer equivalent to the pre-exposure level titer was identified. Reciprocal of the penultimate dilution of end point of a positively seroconverted sample was interpreted as the antibody end-point titer. Antibody titers to both BPL inactivated and formalin inactivated Zika vaccine formulations were higher with aluminum hydroxide than with antigens alone. Vaccine formulations of the formalin inactivated vaccine at all doses (FIG. 9A-9C) and all doses of BPL inactivated vaccine (data not shown) elicited high level of antibodies, after each dose of vaccine administration confirming that vaccine can be administered as a single dose or two or more doses for eliciting a robust immune response against Zika virus.

Example 12: Antibody Avidity

The quality of antibody responses to the vaccine was estimated by antibody avidity assays. The antigen-antibody binding avidities are the degree of affinity maturation in the B-cells. Higher antibody avidities correlate with neutralizing antibodies in several vaccine studies. Prior to determination of avidity index, titrations with sodium isothiocyanate (NaSCN) from 0 M to 6 M concentration in 0.25 M steps from 0 to 2.0 M were performed. After addition and incubation of primary antisera to the antigen coated plates, the plates were incubated with graded concentrations NaSCN for 15 min with intermittent shaking, washed and developed as in regular ELISA. The optical densities obtained at each of the concentrations were plotted. The highest OD (A) was plotted and halved (A/2), and the distance between the OD curves at A/2 was measured as the NaSCN shift value. The NaSCN shift was higher after the first booster dose compared to the prime dose and remained static or marginally increased further after second booster dose administration indicating that high affinity antibodies developed over time and with booster injections. A reference point in the ELISA titration was taken calculation of avidity index, (AI]) which is the ratio of antibody concentration (measured by absorbance) in ELISA of serum samples treated with and without the chaotropic agent NaSCN. Even at the lowest single dose concentration of 1 µg of formalin inactivated Zika vaccine, antibodies with high affinity binding to the antigen was detected, indicating the vaccine is potent even at low concentrations of the vaccine antigen (See FIG. 10).

Example 13: Cytokine Profiling

Both Th1 and Th2 cytokines were estimated in mice sera after administration of two doses of the formalin inactivated Zika antigen formulated with different adjuvants including aluminium hydroxide and in antigen only controls for comparison. The Mouse ELISA kit—Th1/Th2 (Catalog No. 88-7711-44, eBioscience) was used for the estimation of IL-2, IFN gamma, IL-4 and IL-10 by methods exactly as per the kit protocols using the standards provided in the kit. The concentration of the cytokines are expressed in µg/mL. The results for Th1 cytokine levels are depicted in FIG. 11A and FIG. 11B and Th2 cytokines in FIG. 12A and FIG. 12B.

Example 14: Estimation of Virus Titers

The amount of infectious virus particles in the upstream and downstream bioprocess samples, Zika virus titers for animal challenge studies were measured by TCID50 (50% Tissue Culture Infectious Dose) assay. This assay measures the dilution of the virus sample that generates cytopathic effect (CPE) in 50% of the cells. Vero cells were seeded in 96-well microplates and incubated in 5% $CO_2$ at 37° C. overnight. The cells were infected with 10-fold serial dilutions of virus sample, followed by incubation for 5 d in 5% $CO_2$ at 33° C. The cells were visually inspected for CPE and the TCID50 titer was calculated according to the method of Reed and Muench, 1938. The results are presented as a log 10 titer (10×TCID50 units/mL). Alternatively plaque assays were used and the titers were expressed as plaque forming units, PFU/mL. The protocol is similar to PRNT50 assays described in Example 9 except that the incubation of the virus with serially diluted sera samples is not carried out.

REFERENCES

1. Cooper P D, Steele E J. The adjuvanticity of gamma inulin. Immunol Cell Biol. 1988, 66:345-52.
2. Reed L J. Muench H. A simple method of estimating fifty percent endpoints. Am. J. Epidemiol. (1938) 27 (3): 493-497 4849-0458-9365, v. 1

We claim:

1. An immunogenic composition comprising a structural antigen of Zika virus and a structural antigen of Chikungunya virus,
   wherein the structural antigen of Zika virus comprises an amino acid sequence encoded by the sequence of SEQ ID NO: 1 or SEQ ID NO: 2 or the amino acid sequence as set forth in SEQ ID NO: 3 or SEQ ID NO: 4; and a pharmaceutically acceptable buffer;
   wherein the Zika virus and the Chikungunya virus are subjected to inactivation such that the composition is rendered non-infectious, and
   wherein the composition elicits an immune response to Zika virus and Chikungunya virus in mammals.

2. The composition according to claim 1, wherein the Zika virus and/or the Chikungunya virus is a whole virus.

3. The composition according to claim 2, wherein the inactivation was performed by exposure of the whole virus to one or more treatments selected from the group consisting of a treatment with a chemical inactivating agent, treatment with a physical inactivating agent, treatments with an irradiating agent, and heat treatments.

4. The composition according to claim 3, wherein the chemical inactivating agent is selected from the group consisting of formalin (formaldehyde), beta propiolactone (BPL) and hydrogen peroxide.

5. The composition according to claim 3, wherein the irradiating agent comprises gamma irradiation or UV irradiation.

6. The composition according to claim 1, wherein the Zika virus and/or the Chikungunya virus is purified and inactivation is carried out before or after purification.

7. The composition according to claim 1, wherein the Zika antigen comprises one or more antigens selected from envelope (E) protein, membrane (M) protein, and prME protein, obtained or derived from the Zika virus.

8. The composition according to claim 1, wherein the Chikungunya antigen comprises one or more antigens selected from the group consisting of capsid protein, E1 protein, E2 protein, and 6k protein, obtained or derived from the Chikungunya virus.

9. The composition according to claim 1, wherein the Zika antigen and/or the Chikungunya antigen are expressed as virus like particles in a prokaryotic or eukaryotic expression system.

10. The composition according to claim 1, wherein the composition elicits Th1 and/or Th2 immune response to infection by Zika virus and Chikungunya virus.

11. The composition according to claim 1, wherein the buffer is selected from the group consisting of a phosphate buffer, a sodium chloride buffer, a citrate buffer, a phosphate citrate buffer, a borate buffer, a tris(hydroxymethly)aminomethane (Tris) containing buffer, a succinate buffer, and buffers containing glycine or histidine as one of the buffering agents.

12. The composition according to claim 11, wherein the phosphate buffer comprises sodium phosphate at concentration of 5 mM up to 200 mM of phosphate ions at a pH of 6.5 to 9, or the sodium chloride buffer comprises sodium chloride at a concentration of 50 mM to 200 mM.

13. The composition according to claim 1, wherein the composition further comprises an adjuvant.

14. The composition according to claim 13, wherein the adjuvant is selected from the group consisting of: an aluminum salt; inulin; algammaulin; monophosphoryl lipid A (MPL); resiquimod; muramyl dipeptide (MDP); N-glycolyl dipeptide (GMDP); polyIC; CpG oligonucleotide; aluminum hydroxide with MPL; water in oil emulsion; oil in water emulsion; and combinations thereof.

15. The composition according to claim 14, wherein the composition comprises aluminum hydroxide at a concentration of from 0.1 mg to 1.5 mg of aluminum per vaccine dose.

16. The composition according to claim 1, which comprises 2-phenoxyethanol at a concentration of 2.5 to 5 mg/mL.

17. The composition according to claim 1, wherein the composition is in a liquid or a lyophilized form.

18. The composition according to claim 1, wherein the composition is contained within pre-filled syringes, microneedle patch, needle-free patch, and/or inhalation or nasal sprays.

19. An Immunogenic composition comprising:
one or more recombinant antigens of a structural protein of a Zika virus and one or more recombinant antigens of a structural protein nucleic acid of a Chikungunya virus, and
a pharmaceutically acceptable buffer,
wherein the structural protein of Zika virus comprises an amino acid sequence encoded by the sequence of SEQ ID NO: 1 or SEQ ID NO: 2 or the amino acid sequence as set forth in SEQ ID NO: 3 or SEQ ID NO: 4; and
wherein the composition elicits an immune response to infection by Zika virus and Chikungunya virus in a mammal.

20. The composition according to claim 19, wherein the one or more recombinant antigens are selected from the envelope (E) protein, membrane (M) protein, and prME protein, obtained or derived from the Zika virus, and one or more recombinant antigens are selected from capsid protein, E1 protein, E2 protein, and 6k protein, obtained or derived from the Chikungunya virus.

21. The composition according to claim 19, wherein the one or more recombinant antigens are expressed as virus like particles in a prokaryotic or eukaryotic expression system.

22. The composition according to claim 19, which elicits Th1 and/or Th2 immune response against infection by Zika virus and by Chikungunya virus in the mammal.

23. The composition according to claim 19, wherein the buffer is selected from the group consisting of a phosphate buffer, a sodium chloride buffer, a citrate buffer, a phosphate citrate buffer, a borate buffer, a tris(hydroxymethly)aminomethane (Tris) containing buffer, a succinate buffer, and buffers containing glycine or histidine as one of the buffering agents.

24. The composition according to claim 23, wherein the phosphate buffer comprises sodium phosphate at concentration of 5 mM up to 200 mM of phosphate ions at a pH of 6.5 to 9 or the sodium chloride buffer comprises sodium chloride at a concentration of 50 mM to 200 mM.

25. The composition according to claim 19, wherein the composition comprises an adjuvant.

26. The composition according to claim 25, wherein the adjuvant is selected from the group consisting of an aluminum, inulin, algammaulin, monophosphoryl lipid A (MPL), resiquimod, muramyl dipeptide (MDP), N-glycolyl dipeptide (GMDP), polyIC, CpG oligonucleotide, aluminum hydroxide with MPL, water in oil emulsion, oil in water emulsion, and combinations thereof.

27. The composition according to claim 26, wherein the adjuvant comprises aluminum hydroxide at a concentration of 0.1 mg to 1.5 mg of aluminum per vaccine dose.

28. The composition according to claim 19, wherein the composition comprises 2-phenoxyethanol at a concentration of 2.5 to 5 mg/mL.

29. The composition according to claim 19, which is aqueous or lyophilized.

30. The composition according to claim 19, which is contained within pre-filled syringes, microneedle patch, needle-free patch, and/or inhalation or nasal sprays.

31. The composition of claim 4, wherein the inactivation comprises a treatment selected from the group consisting of:
(a) treatment with formalin at a formalin to virus ratio of 1:500 to 1:4000 (v/v) at 8° C. to 37° C. for 1 to 7 days;
(b) treatment with formalin at a formalin to virus ratio of 1:500 to 1:4000 (v/v) at 2° C. to 8° C. for 10 to 30 days;
(c) treatment with formalin at a formalin to virus ratio of 1:500 to 1:4000 (v/v) at 25±3° C. for 1 to 7 days;
(d) treatment with Beta-propiolactone (BPL) at a BPL to virus ratio of 1:500 to 1:4000 (v/v) at 8° C. to 30° C. for 24 to 48 hours;
(e) treatment with BPL at a BPL to virus ratio of 1:500 to 1:4000 (v/v) at 2° C. to 8° C. for 3 to 7 days;
(f) treatment with BPL at a BPL to virus ratio of 1:500 to 1:4000 (v/v) at 25±3° C. for 48 hours;
(g) treatment with formalin as set forth in a, b, or c, plus treatment with BPL as set forth in d, e, or f;
(h) treatment with formalin at a formalin to virus ratio of 1:3000 (v/v) at 15° C. to 30° C. for 24 to 48 hours plus treatment with BPL and BPL to virus ration of 1:3000 (v/v) at 15° C. to 30° C. for 24 hours;
(i) treatment with formalin at a formalin to virus ratio of 1:3000 at 25±3° C. for 24 to 48 hours plus treatment with BPL at a BPL to virus ration of 1:3000 (v/v) at 25±3° C. for 24 hours;
(j) treatment with hydrogen peroxide at a hydrogen peroxide concentration of 0.1% to 3% at 20° C. to 30° C. for 5 minutes to 120 minutes; and
(k) treatment with hydrogen peroxide at a hydrogen peroxide concentration of 0.1% to 1% at 20° C. to 30° C. for 5 minutes to 120 minutes.

32. An immunogenic composition comprising an antigen obtained or derived from a Zika Virus, and a pharmaceutically acceptable buffer, wherein the antigen is rendered non infectious through inactivation and/or is recombinantly engineered from the nucleic acid of a Zika virus; and the antigen contains the amino acid sequence of SEQ ID NO 3 and/or SEQ ID NO 4.

33. The immunogenic composition of claim 32, wherein the Zika virus and the CHIKV virus are inactivated and inactivation comprises a treatment selected from the group consisting of:
 (a) treatment with formalin at a formalin to virus ratio of 1:500 to 1:4000 (v/v) at 8° C. to 37° C. for 1 to 7 days;
 (b) treatment with formalin at a formalin to virus ratio of 1:500 to 1:4000 (v/v) at 2° C. to 8° C. for 10 to 30 days;
 (c) treatment with formalin at a formalin to virus ratio of 1:500 to 1:4000 (v/v) at 25±3° C. for 1 to 7 days;
 (d) treatment with Beta-propiolactone (BPL) at a BPL to virus ratio of 1:500 to 1:4000 (v/v) at 8° C. to 30° C. for 24 to 48 hours;
 (e) treatment with BPL at a BPL to virus ratio of 1:500 to 1:4000 (v/v) at 2° C. to 8° C. for 3 to 7 days;
 (f) treatment with BPL at a BPL to virus ratio of 1:500 to 1:4000 (v/v) at 25±3° C. for 48 hours;
 (g) treatment with formalin as set forth in a, b, or c, plus treatment with BPL as set forth in d, e, or f;
 (h) treatment with formalin at a formalin to virus ratio of 1:3000 (v/v) at 15° C. to 30° C. for 24 to 48 hours plus treatment with BPL and BPL to virus ration of 1:3000 (v/v) at 15° C. to 30° C. for 24 hours;
 (i) treatment with formalin at a formalin to virus ratio of 1:3000 at 25±3° C. for 24 to 48 hours plus treatment with BPL at a BPL to virus ration of 1:3000 (v/v) at 25±3° C. for 24 hours;
 (j) treatment with hydrogen peroxide at a hydrogen peroxide concentration of 0.1% to 3% at 20° C. to 30° C. for 5 minutes to 120 minutes; and
 (k) treatment with hydrogen peroxide at a hydrogen peroxide concentration of 0.1% to 1% at 20° C. to 30° C. for 5 minutes to 120 minutes.

34. The composition of claim 14, wherein the aluminum salt comprises aluminum hydroxide, aluminum phosphate or aluminum sulfate phosphate.

35. The composition of claim 26, wherein the aluminum salt comprises aluminum hydroxide, aluminum phosphate or aluminum sulfate phosphate.

* * * * *

SEQUENCE LISTING

```
<160> NUMBER OF SEQ ID NOS: 8

<210> SEQ ID NO 1
<211> LENGTH: 2121
<212> TYPE: DNA
<213> ORGANISM: Zika virus

<400> SEQUENCE: 1
```

-continued

```
ctcgaggaat tcggatccaa ctcctaaaaa accgccacca tggcagatac cagcgtcggc         60
atcgtcggac tcttgttgat taccacggca atggcagcag aagtgacccg cagggggcagc       120
gcctactaca tgtacctcga caggaacgat gcgggagagg ctatcagctt ccctaccact       180
ttgggcatga acaagtgtta catccagatt atggacctgg gtcacatgtg cgatgctacc       240
atgtcttacg aatgtcctat gctggacgag ggcgtggaac ccgacgatgt cgattgctgg       300
tgtaacacaa cgagtacttg ggtggtgtac ggtacatgtc accataagaa aggtgaagct       360
aggcgttcga ggagagctgt gacgctcccc agtcactcga ccaggaagtt gcagactaga       420
agtcaaacat ggctggagtc gcgcgaatac acaaaacatc tgatcagggt cgaaaactgg       480
attttcagaa accctggatt cgctctcgct gccgcagcga tcgcttggct gctcggttcc       540
agcacctccc aaaaggttat ttacctggtc atgatcttgc tgattgctcc cgcctactcc       600
atccgctgca ttggcgttag caaccgtgac ttcgtggagg aatgagcgg tggcacttgg       660
gtggatgttg tgttggaaca cggaggttgt gtcacggtta tggctcagga caagccaacc       720
gttgatatcg agctggtcac cactacagtt tctaacatgg ctgaggtcag gtcatactgc       780
tacgaagcct ccatcagcga catggcatct gattcaagat gtccgaccca aggtgaagct       840
tacctcgaca agcagtcaga tactcaatac gtctgcaaac gcacattggt tgaccgtggc       900
tggggaaacg gttgtggcct cttcggaaag ggtagtttgg tcacgtgcgc caaattcgca       960
tgtagtaaga aaatgaccgg caagtcgatc cagccagaga acctggaata ccgcattatg      1020
ctctctgtgc acggaagtca acattcgggt atgatcgtca cgacacggg ccacgagacc       1080
gatgaaaacc gcgccaaggt ggagatcacg cctaactctc cccgtgcaga agctaccctc      1140
ggcggattcg gatcactggg tctcgactgc gagccccgta ctggcttgga cttctcagat      1200
ttgtactacc tgacaatgaa caacaagcac tggctcgtcc ataaagaatg gttccacgac      1260
atcccactgc cttggcacgc tggagctgat actggcaccc ctcactggaa caacaaggag      1320
gccctggtgg agttcaagga cgcacatgcg aaacgccaga cagtcgttgt gctcggctcc      1380
caagaaggag ctgtgcacac tgctctggcc ggtgctctgg aggccgaaat ggacggcgca      1440
aagggacgtc tgtcttcagg ccatttgaaa tgcaggctga agatggacaa attgagactg      1500
aagggagtga gttactcgtt gtgtacggct gccttcactt tcacaaaaat ccctgctgag      1560
actctgcacg gcacggtgac cgtcgaagtt cagtacgccg gtactgacgg accatgcaag      1620
gtgccggctc agatggctgt cgatatgcaa actttgacac cagtcggcag gctgatcaca      1680
gctaaccccg gttattacga gtctaccgaa aactcaaaga tgatgctgga gctgacccct      1740
cctttcggag attcctacat cgtgattggc gtcggagaaa agaaaatcac ccaccattgg      1800
cacagatccg gtagcactat tggcaaggcc ttcgaggcaa cagttcgcgg tgcgaaacgt      1860
atggctgtgc tgggagacac tgcctgggat ttcggttccg tgggtggtgc tctgaactcc      1920
ctgggcaagg gcatccacca gattttcgga gcagcgttca aaagcctgtt cggaggtatg      1980
tcctggttca gccaaatcct cattggtact ctcttgatgt ggctgggcct caacacaaag      2040
aacggatcta tctcactgat gtgcttggct ttgggaggtg ttttgatctt cttgtctact      2100
gctgtgagcg ccgatgtggg a                                                 2121
```

<210> SEQ ID NO 2
<211> LENGTH: 2079
<212> TYPE: DNA
<213> ORGANISM: Zika virus

<400> SEQUENCE: 2

-continued

```
atggcagaca ccagcatcgg aatcattggc ctcctgctga ctacagccat ggcagcagag    60
atcactagac gcgggagtgc atactacatg tacttggata ggagcgatgc cgggaaggcc   120
atttcgtttg ctaccacatt gggagtgaac aagtgccacg tacagatcat ggacctcggg   180
cacatgtgtg acgccaccat gagttatgag tgccctatgc tggatgaggg agtggaacca   240
gatgatgtcg attgctggtg caacacgaca tcaacttggg ttgtgtacgg aacctgtcat   300
cacaaaaaag gtgaggcacg gcgatctaga agagccgtga cgctcccttc tcactctaca   360
aggaagttgc aaacgcggtc gcagacctgg ttagaatcaa gagaatacac gaagcacttg   420
atcaaggttg aaaactggat attcaggaac cccgggtttg cgctagtggc cgttgccatt   480
gcctggcttt gggaagctc gacgagccaa aaagtcatat acttggtcat gatactgctg   540
attgccccgg catacagtat caggtgcatt ggagtcagca atagagactt cgtggagggc   600
atgtcaggtg ggacctgggt tgatgttgtc ttggaacatg gaggctgcgt taccgtgatg   660
gcacaggaca agccaacagt tgacatagag ttggtcacga cgacggttag taacatggcc   720
gaggtaagat cctattgcta cgaggcatcg atatcggaca tggcttcgga cagtcgttgc   780
ccaacacaag gtgaagccta ccttgacaag caatcagaca ctcaatatgt ctgcaaaaga   840
acattagtgg acagaggttg gggaaacggt tgtggacttt ttggcaaagg gagcttggtg   900
acatgtgcca gtttacgtg ttctaagaag atgaccggga gagcattca accgaaaat   960
ctggagtatc ggataatgct atcagtgcat ggctcccagc atagcgggat gattgtcaat  1020
gatacaggat atgaaactga cgaaaataga gcgaaagtcg aggttacgcc taattcacca  1080
agagcggaag caaccttggg aggctttgga agcttaggac ttgactgtga accaaggaca  1140
ggccttgact tttcagatct gtattacctg accatgaaca ataagcattg gttggtgcac  1200
aaagagtggt tcatgacat cccattgcct tggcatgctg gggcagacac cggaactcca  1260
cactggaaca caaagaggc attggtagaa ttcaaggatg cccacgccaa gaggcaaacc  1320
gtcgtcgttc tggggagcca ggaaggagcc gttcacacgg ctctcgctgg agctctagag  1380
gctgagatgg atggtgcaaa gggaaagctg ttctctggcc atttgaaatg ccgcctaaaa  1440
atggacaagc ttagattgaa gggcgtgtca tattccttgt gcactgcggc attcacattc  1500
accaaggtcc cagctgaaac actgcatgga acagtcacag tggaggtgca gtatgcaggg  1560
acagatggac cctgcaagat cccagtccag atggcggtgg acatgcagac cctgacccca  1620
gttggaaggc tgataaccgc caaccccgtg attactgaaa gcactgagaa ctcaaagatg  1680
atgttggagc ttgaccccac atttgggat tcttacattg tcataggagt tggggacaag  1740
aaaatcaccc accactggca taggagtggt agcaccatcg gaaaggcatt tgaggccact  1800
gtgagaggcg ccaagagaat ggcagtcctg ggggatacag cctgggactt cggatcagtc  1860
gggggtgtgt tcaactcact gggtaagggc attcaccaga ttttggagc agccttcaaa  1920
tcactgtttg gaggaatgtc ctggttctca cagatcctca taggcacgct gctagtgtgg  1980
ttaggtttga acacaaagaa tggatctatc tccctcacat gcttggccct gggggagtg  2040
atgatcttcc tctccacggc tgtttctgct gacgtgggg                         2079
```

<210> SEQ ID NO 3
<211> LENGTH: 694
<212> TYPE: PRT
<213> ORGANISM: Zika virus

<400> SEQUENCE: 3

-continued

```
Met Ala Asp Thr Ser Val Gly Ile Val Gly Leu Leu Leu Ile Thr Thr
1               5                   10                  15

Ala Met Ala Ala Glu Val Thr Arg Arg Gly Ser Ala Tyr Tyr Met Tyr
            20                  25                  30

Leu Asp Arg Asn Asp Ala Gly Glu Ala Ile Ser Phe Pro Thr Thr Leu
        35                  40                  45

Gly Met Asn Lys Cys Tyr Ile Gln Ile Met Asp Leu Gly His Met Cys
    50                  55                  60

Asp Ala Thr Met Ser Tyr Glu Cys Pro Met Leu Asp Glu Gly Val Glu
65                  70                  75                  80

Pro Asp Asp Val Asp Cys Trp Cys Asn Thr Thr Ser Thr Trp Val Val
                85                  90                  95

Tyr Gly Thr Cys His His Lys Lys Gly Glu Ala Arg Arg Ser Arg Arg
            100                 105                 110

Ala Val Thr Leu Pro Ser His Ser Thr Arg Lys Leu Gln Thr Arg Ser
            115                 120                 125

Gln Thr Trp Leu Glu Ser Arg Glu Tyr Thr Lys His Leu Ile Arg Val
        130                 135                 140

Glu Asn Trp Ile Phe Arg Asn Pro Gly Phe Ala Leu Ala Ala Ala Ala
145                 150                 155                 160

Ile Ala Trp Leu Leu Gly Ser Ser Thr Ser Gln Lys Val Ile Tyr Leu
                165                 170                 175

Val Met Ile Leu Leu Ile Ala Pro Ala Tyr Ser Ile Arg Cys Ile Gly
            180                 185                 190

Val Ser Asn Arg Asp Phe Val Glu Gly Met Ser Gly Gly Thr Trp Val
        195                 200                 205

Asp Val Val Leu Glu His Gly Gly Cys Val Thr Val Met Ala Gln Asp
    210                 215                 220

Lys Pro Thr Val Asp Ile Glu Leu Val Thr Thr Thr Val Ser Asn Met
225                 230                 235                 240

Ala Glu Val Arg Ser Tyr Cys Tyr Glu Ala Ser Ile Ser Asp Met Ala
                245                 250                 255

Ser Asp Ser Arg Cys Pro Thr Gln Gly Glu Ala Tyr Leu Asp Lys Gln
            260                 265                 270

Ser Asp Thr Gln Tyr Val Cys Lys Arg Thr Leu Val Asp Arg Gly Trp
        275                 280                 285

Gly Asn Gly Cys Gly Leu Phe Gly Lys Gly Ser Leu Val Thr Cys Ala
    290                 295                 300

Lys Phe Ala Cys Ser Lys Lys Met Thr Gly Lys Ser Ile Gln Pro Glu
305                 310                 315                 320

Asn Leu Glu Tyr Arg Ile Met Leu Ser Val His Gly Ser Gln His Ser
                325                 330                 335

Gly Met Ile Val Asn Asp Thr Gly His Glu Thr Asp Glu Asn Arg Ala
            340                 345                 350

Lys Val Glu Ile Thr Pro Asn Ser Pro Arg Ala Glu Ala Thr Leu Gly
        355                 360                 365

Gly Phe Gly Ser Leu Gly Leu Asp Cys Glu Pro Arg Thr Gly Leu Asp
    370                 375                 380

Phe Ser Asp Leu Tyr Tyr Leu Thr Met Asn Asn Lys His Trp Leu Val
385                 390                 395                 400

His Lys Glu Trp Phe His Asp Ile Pro Leu Pro Trp His Ala Gly Ala
                405                 410                 415

Asp Thr Gly Thr Pro His Trp Asn Asn Lys Glu Ala Leu Val Glu Phe
```

```
                420             425             430
Lys Asp Ala His Ala Lys Arg Gln Thr Val Val Leu Gly Ser Gln
            435             440             445

Glu Gly Ala Val His Thr Ala Leu Ala Gly Ala Leu Glu Ala Glu Met
        450                 455             460

Asp Gly Ala Lys Gly Arg Leu Ser Ser Gly His Leu Lys Cys Arg Leu
465             470                 475             480

Lys Met Asp Lys Leu Arg Leu Lys Gly Val Ser Tyr Ser Leu Cys Thr
                485             490             495

Ala Ala Phe Thr Phe Thr Lys Ile Pro Ala Glu Thr Leu His Gly Thr
            500             505             510

Val Thr Val Glu Val Gln Tyr Ala Gly Thr Asp Gly Pro Cys Lys Val
        515             520             525

Pro Ala Gln Met Ala Val Asp Met Gln Thr Leu Thr Pro Val Gly Arg
        530             535             540

Leu Ile Thr Ala Asn Pro Val Ile Thr Glu Ser Thr Glu Asn Ser Lys
545             550             555             560

Met Met Leu Glu Leu Asp Pro Pro Phe Gly Asp Ser Tyr Ile Val Ile
                565             570             575

Gly Val Gly Glu Lys Lys Ile Thr His His Trp His Arg Ser Gly Ser
            580             585             590

Thr Ile Gly Lys Ala Phe Glu Ala Thr Val Arg Gly Ala Lys Arg Met
        595             600             605

Ala Val Leu Gly Asp Thr Ala Trp Asp Phe Gly Ser Val Gly Gly Ala
        610             615             620

Leu Asn Ser Leu Gly Lys Gly Ile His Gln Ile Phe Gly Ala Ala Phe
625             630             635             640

Lys Ser Leu Phe Gly Gly Met Ser Trp Phe Ser Gln Ile Leu Ile Gly
                645             650             655

Thr Leu Leu Met Trp Leu Gly Leu Asn Thr Lys Asn Gly Ser Ile Ser
            660             665             670

Leu Met Cys Leu Ala Leu Gly Gly Val Leu Ile Phe Leu Ser Thr Ala
        675             680             685

Val Ser Ala Asp Val Gly
        690

<210> SEQ ID NO 4
<211> LENGTH: 693
<212> TYPE: PRT
<213> ORGANISM: Zika virus

<400> SEQUENCE: 4

Met Ala Asp Thr Ser Ile Gly Ile Ile Gly Leu Leu Leu Thr Thr Ala
1               5                   10                  15

Met Ala Ala Glu Ile Thr Arg Arg Gly Ser Ala Tyr Tyr Met Tyr Leu
            20                  25                  30

Asp Arg Ser Asp Ala Gly Lys Ala Ile Ser Phe Ala Thr Thr Leu Gly
        35                  40                  45

Val Asn Lys Cys His Val Gln Ile Met Asp Leu Gly His Met Cys Asp
    50                  55                  60

Ala Thr Met Ser Tyr Glu Cys Pro Met Leu Asp Glu Gly Val Glu Pro
65                  70                  75                  80

Asp Asp Val Asp Cys Trp Cys Asn Thr Thr Ser Thr Trp Val Val Tyr
                85                  90                  95
```

```
Gly Thr Cys His His Lys Lys Gly Glu Ala Arg Arg Ser Arg Arg Ala
            100                 105                 110

Val Thr Leu Pro Ser His Ser Thr Arg Lys Leu Gln Thr Arg Ser Gln
        115                 120                 125

Thr Trp Leu Glu Ser Arg Glu Tyr Thr Lys His Leu Ile Lys Val Glu
    130                 135                 140

Asn Trp Ile Phe Arg Asn Pro Gly Phe Ala Leu Val Ala Val Ala Ile
145                 150                 155                 160

Ala Trp Leu Leu Gly Ser Ser Thr Ser Gln Lys Val Ile Tyr Leu Val
                165                 170                 175

Met Ile Leu Leu Ile Ala Pro Ala Tyr Ser Ile Arg Cys Ile Gly Val
            180                 185                 190

Ser Asn Arg Asp Phe Val Glu Gly Met Ser Gly Gly Thr Trp Val Asp
        195                 200                 205

Val Val Leu Glu His Gly Gly Cys Val Thr Val Met Ala Gln Asp Lys
    210                 215                 220

Pro Thr Val Asp Ile Glu Leu Val Thr Thr Val Ser Asn Met Ala
225                 230                 235                 240

Glu Val Arg Ser Tyr Cys Tyr Glu Ala Ser Ile Ser Asp Met Ala Ser
                245                 250                 255

Asp Ser Arg Cys Pro Thr Gln Gly Glu Ala Tyr Leu Asp Lys Gln Ser
            260                 265                 270

Asp Thr Gln Tyr Val Cys Lys Arg Thr Leu Val Asp Arg Gly Trp Gly
        275                 280                 285

Asn Gly Cys Gly Leu Phe Gly Lys Gly Ser Leu Val Thr Cys Ala Lys
    290                 295                 300

Phe Thr Cys Ser Lys Lys Met Thr Gly Lys Ser Ile Gln Pro Glu Asn
305                 310                 315                 320

Leu Glu Tyr Arg Ile Met Leu Ser Val His Gly Ser Gln His Ser Gly
                325                 330                 335

Met Ile Val Asn Asp Thr Gly Tyr Glu Thr Asp Glu Asn Arg Ala Lys
            340                 345                 350

Val Glu Val Thr Pro Asn Ser Pro Arg Ala Glu Ala Thr Leu Gly Gly
        355                 360                 365

Phe Gly Ser Leu Gly Leu Asp Cys Glu Pro Arg Thr Gly Leu Asp Phe
    370                 375                 380

Ser Asp Leu Tyr Tyr Leu Thr Met Asn Asn Lys His Trp Leu Val His
385                 390                 395                 400

Lys Glu Trp Phe His Asp Ile Pro Leu Pro Trp His Ala Gly Ala Asp
                405                 410                 415

Thr Gly Thr Pro His Trp Asn Asn Lys Glu Ala Leu Val Glu Phe Lys
            420                 425                 430

Asp Ala His Ala Lys Arg Gln Thr Val Val Val Leu Gly Ser Gln Glu
        435                 440                 445

Gly Ala Val His Thr Ala Leu Ala Gly Ala Leu Glu Ala Glu Met Asp
    450                 455                 460

Gly Ala Lys Gly Lys Leu Phe Ser Gly His Leu Lys Cys Arg Leu Lys
465                 470                 475                 480

Met Asp Lys Leu Arg Leu Lys Gly Val Ser Tyr Ser Leu Cys Thr Ala
                485                 490                 495

Ala Phe Thr Phe Thr Lys Val Pro Ala Glu Thr Leu His Gly Thr Val
            500                 505                 510

Thr Val Glu Val Gln Tyr Ala Gly Thr Asp Gly Pro Cys Lys Ile Pro
```

-continued

```
        515                 520                 525

Val Gln Met Ala Val Asp Met Gln Thr Leu Thr Pro Val Gly Arg Leu
    530                 535                 540

Ile Thr Ala Asn Pro Val Ile Thr Glu Ser Thr Glu Asn Ser Lys Met
545                 550                 555                 560

Met Leu Glu Leu Asp Pro Pro Phe Gly Asp Ser Tyr Ile Val Ile Gly
                565                 570                 575

Val Gly Asp Lys Lys Ile Thr His His Trp His Arg Ser Gly Ser Thr
            580                 585                 590

Ile Gly Lys Ala Phe Glu Ala Thr Val Arg Gly Ala Lys Arg Met Ala
        595                 600                 605

Val Leu Gly Asp Thr Ala Trp Asp Phe Gly Ser Val Gly Gly Val Phe
    610                 615                 620

Asn Ser Leu Gly Lys Gly Ile His Gln Ile Phe Gly Ala Ala Phe Lys
625                 630                 635                 640

Ser Leu Phe Gly Gly Met Ser Trp Phe Ser Gln Ile Leu Ile Gly Thr
                645                 650                 655

Leu Leu Val Trp Leu Gly Leu Asn Thr Lys Asn Gly Ser Ile Ser Leu
            660                 665                 670

Thr Cys Leu Ala Leu Gly Gly Val Met Ile Phe Leu Ser Thr Ala Val
        675                 680                 685

Ser Ala Asp Val Gly
    690

<210> SEQ ID NO 5
<211> LENGTH: 10269
<212> TYPE: DNA
<213> ORGANISM: Zika virus

<400> SEQUENCE: 5
atgaaaaacc caaagaagaa atccggagga ttccggattg tcaatatgct aaaacgcgga      60
gtagcccgtg taaacccctt gggaggtttg aagaggttgc cagccggact tctgctgggt     120
catggaccca tcagaatggt tttggcgata ctagcctttt tgagatttac agcaatcaag     180
ccatcactgg gccttatcaa cagatggggt tccgtgggga aaaaagaggc tatggaaata     240
ataaagaagt tcaagaaaga tcttgctgcc atgttgagaa taatcaatgc taggaaagag     300
aggaagagac gtggcgcaga caccagcatc ggaatcattg gcctcctgct gactacagcc     360
atggcagcag agatcactag acgcgggagt gcatactaca tgtacttgga taggagcgat     420
gccgggaagg ccatttcgtt tgctaccaca ttgggagtga acaagtgcca cgtacagatc     480
atggacctcg ggcacatgtg tgacgccacc atgagttatg agtgccctat gctggatgag     540
ggagtggaac cagatgatgt cgattgctgg tgcaacacga catcaacttg ggttgtgtac     600
ggaacctgtc atcacaaaaa aggtgaggca cggcgatcta gaagagccgt gacgctccct     660
tctcactcta caaggaagtt gcaaacgcgg tcgcagacct ggttagaatc aagagaatac     720
acgaagcact tgatcaaggt tgaaaactgg atattcagga accccgggtt tgcgctagtg     780
gccgttgcca ttgcctggct tttgggaagc tcgacgagcc aaaaagtcat atacttggtc     840
atgatactgc tgattgcccc ggcatacagt atcaggtgca ttggagtcag caatagagac     900
ttcgtggagg gcatgtcagg tgggacctgg gttgatgttg tcttggaaca tggaggctgc     960
gttaccgtga tggcacagga caagccaaca gttgacatag agttggtcac gacgacggtt    1020
agtaacatgg ccgaggtaag atcctattgc tacgaggcat cgatatcgga catggcttcg    1080
```

```
gacagtcgtt gcccaacaca aggtgaagcc taccttgaca agcaatcaga cactcaatat   1140
gtctgcaaaa gaacattagt ggacagaggt tggggaaacg gttgtggact ttttggcaaa   1200
gggagcttgg tgacatgtgc caagtttacg tgttctaaga agatgaccgg gaagagcatt   1260
caaccggaaa atctggagta tcggataatg ctatcagtgc atggctccca gcatagcggg   1320
atgattgtca atgatacagg atatgaaact gacgaaaata gagcgaaagt cgaggttacg   1380
cctaattcac caagagcgga agcaaccttg ggaggctttg gaagcttagg acttgactgt   1440
gaaccaagga caggccttga cttttcagat ctgtattacc tgaccatgaa caataagcat   1500
tggttggtgc acaaagagtg gtttcatgac atcccattgc cttggcatgc tggggcagac   1560
accggaactc cacactggaa caacaaagag gcattggtag aattcaagga tgcccacgcc   1620
aagaggcaaa ccgtcgtcgt tctggggagc caggaaggag ccgttcacac ggctctcgct   1680
ggagctctag aggctgagat ggatggtgca aagggaaagc tgttctctgg ccatttgaaa   1740
tgccgcctaa aaatgacaaa gcttagattg aagggcgtgt catattcctt gtgcactgcg   1800
gcattcacat tcaccaaggt cccagctgaa acactgcatg gaacagtcac agtggaggtg   1860
cagtatgcag ggacagatgg accctgcaag atcccagtcc agatggcggt ggacatgcag   1920
accctgaccc cagttggaag gctgataacc gccaaccccg tgattactga aagcactgag   1980
aactcaaaga tgatgttgga gcttgaccca ccatttgggg attcttacat tgtcatagga   2040
gttggggaca gaaaaatcac ccaccactgg cataggagtg gtagcaccat cggaaaggca   2100
tttgaggcca ctgtgagagg cgccaagaga atggcagtcc tgggggatac agcctgggac   2160
ttcggatcag tcgggggtgt gttcaactca ctgggtaagg gcattcacca gattttgga   2220 gcagccttca aatcactgtt tggaggaatg tcctggttct cacagatcct cataggcacg   2280
ctgctagtgt ggttaggttt gaacacaaag aatggatcta tctccctcac atgcttggcc   2340 ctgggggag tgatgatctt cctctccacg gctgtttctg ctgacgtggg gtgctcagtg   2400
gacttctcaa aaaaggaaac gagatgtggc acggggtat tcatctataa tgatgttgaa   2460
gcctggaggg accggtacaa gtaccatcct gactccccc gcagattggc agcagcagtc   2520
aagcaggcct gggaagaggg gatctgtggg atctcatccg tttcaagaat ggaaaacatc   2580
atgtggaaat cagtagaagg ggagctcaat gctatcctag aggagaatgg agttcaactg   2640
acagttgttg tgggatctgt aaaaaacccc atgtggagag gtccacaaag attgccagtg   2700
cctgtgaatg agctgcccca tggctggaaa gcctggggga atcgtatttt gttagggcg   2760 gcaaagacca caacagtttt tgttgtcgac ggtgacacac tgaaggaatg tccgcttgag   2820
cacagagcat ggaatagttt tcttgtggag gatcacgggt ttgagtcttc cacaccagt   2880 gtctggctta aggtcagaga agattactca ttagaatgtg acccagccgt cataggaaca   2940
gctgttaagg gaagggaggc cgcgcacagt gatctgggct attggattga aagtgaaaag   3000
aatgacacat ggaggctgaa gagggcccac ctgattgaga tgaaaacatg tgaatggcca   3060
aagtctcaca cattgtggac agatggagta aagaaaagtg atcttatcat acccaagtct   3120
ttagctggtc cactcagcca ccacaacacc agagagggtt acagaaccca agtgaaaggg   3180
ccatggcaca gtgaagagct tgaaatccgg tttgaggaat gtccaggcac caaggtttac   3240
gtggaggaga catgcggaac tagaggacca tctctgagat caactactgc aagtggaagg   3300
gtcattgagg aatggtgctg tagggaatgc acaatgcccc cactatcgtt tcgagcaaaa   3360
gacggctgct ggtatggaat ggagataagg cccaggaaag aaccagagag caacttagtg   3420
aggtcaatgg tgacagcggg gtcaaccgat catatggacc acttctctct tggagtgctt   3480
```

```
gtgattctac tcatggtgca ggaggggttg aagaagagaa tgaccacaaa gatcatcatg    3540
agcacatcaa tggcagtgct ggtagtcatg atcttgggag gattttcaat gagtgacctg    3600
gccaagcttg tgatcctgat gggtgctact ttcgcagaaa tgaacactgg aggagatgta    3660
gctcacttgg cattggtagc ggcatttaaa gtcagaccag ccttgctggt ctccttcatt    3720
ttcagagcca attggacacc ccgtgagagc atgctgctag ccctggcttc gtgtcttctg    3780
caaactgcga tctctgctct tgaaggtgac ttgatggtcc tcattaatgg atttgctttg    3840
gcctggttgg caattcgagc aatggccgtg ccacgcactg acaacatcgc tctaccaatc    3900
ttggctgctc taacaccact agctcgaggc acactgctcg tggcatggag agcgggcctg    3960
gctacttgtg gagggatcat gctcctctcc ctgaaaggga aggtagtgt gaagaagaac     4020 ctgccatttg tcatggccct gggattgaca gctgtgaggg tagtagaccc tattaatgtg    4080
gtaggactac tgttactcac aaggagtggg aagcggagct ggcccccctag tgaagttctc   4140 acagccgttg gcctgatatg tgcactggcc ggagggtttg ccaaggcaga cattgagatg    4200
gctggaccca tggctgcagt aggcttgcta attgtcagct atgtggtctc gggaaagagt    4260
gtggacatgt acattgaaag agcaggtgac atcacatggg aaaaggacgc ggaagtcact    4320
ggaaacagtc ctcggcttga cgtggcactg gatgagagtg gtgatttctc cttggtagag    4380
gaagatggtc cacccatgag agagatcata ctcaaggtgg tcctgatggc catctgtggc    4440
atgaacccaa tagctatacc ttttgctgca ggagcgtggt atgtgtatgt gaagactggg    4500
aaaaggagtg gcgccctctg ggacgtgcct gctcccaaag aagtgaagaa aggagagacc    4560
acagatggag tgtacagagt gatgactcgc agactgctag gttcaacaca ggttggagtg    4620
ggagtcatgc aagagggagt cttccacacc atgtggcacg ttacaaaagg agccgcactg    4680
aggagcggtg agggaagact tgatccatac tgggggatg tcaagcagga cttggtgtca    4740
tactgtgggc cttggaagtt ggatgcagct tgggatggac tcagcgaggt acagcttttg    4800
gccgtacctc ccggagagag ggccagaaac attcagaccc tgcctggaat attcaagaca    4860
aaggacgggg acatcggagc agttgctctg gactaccctg cagggacctc aggatctccg    4920
atcctagaca aatgtggaag agtgataggaa ctctatggca atgggttgt gatcaagaat    4980 ggaagctatg ttagtgctat aacccaggga aagagggagg aggagactcc ggttgaatgt    5040
ttcgaaccct cgatgctgaa gaagaagcag ctaactgtct tggatctgca tccaggagcc    5100
ggaaaaacca ggagagttct tcctgaaata gtccgtgaag ccataaaaaa gagactccgg    5160
acagtgatct tggcaccaac tagggttgtc gctgctgaga tggaggaggc cttgagagga    5220
cttccggtgc gttacatgac aacagcagtc aacgtcaccc attctgggac agaaatcgtt    5280
gatttgatgt gccatgccac tttcacttca cgcttactac aacccatcag agtccctaat    5340
tacaatctct acatcatgga tgaagcccac ttcacagacc cctcaagtat agctgcaaga    5400
ggatacatat caacaagggt tgaaatgggc gaggcggctg ccatttttat gactgccaca    5460
ccaccaggaa cccgtgatgc gtttcctgac tctaactcac caatcatgga cacagaagtg    5520
gaagtcccag agagagcctg gagctcaggc tttgattggg tgacagacca ttctgggaaa    5580
acagtttggt tcgttccaag cgtgagaaac ggaaatgaaa tcgcagcctg tctgacaaag    5640
gctggaaagc gggtcataca gctcagcagg aagactttgt agacagaatt cagaaaaca    5700 aaaaatcaag agtgggactt tgtcataaca actgacatct cagagatggg cgccaacttc    5760
aaggctgacc gggtcataga ctctaggaga tgcctaaaac cagtcatact tgatggtgag    5820
```

-continued

| | | |
|---|---|---|
| agagtcatct tggctgggcc catgcctgtc acgcatgcta gtgctgctca gaggagagga | 5880 |
| cgtataggca ggaaccctaa caaacctgga gatgagtaca tgtatggagg tgggtgtgca | 5940 |
| gagactgatg aaggccatgc acactggctt gaagcaagaa tgcttcttga caacatctac | 6000 |
| ctccaggatg gcctcatagc ctcgctctat cggcctgagg ccgataaggt agccgccatt | 6060 |
| gagggagagt ttaagctgag gacagagcaa aggaagacct tcgtggaact catgaagaga | 6120 |
| ggagaccttc ccgtctggct agcctatcag gttgcatctg ccggaataac ttacacagac | 6180 |
| agaagatggt gctttgatgg cacaaccaac aacaccataa tggaagacag cgtaccagca | 6240 |
| gaggtgtgga caaagtatgg agagaagaga gtgctcaaac cgagatggat ggatgctagg | 6300 |
| gtctgttcag accatgcggc cctgaagtcg ttcaaagaat cgccgctgg aaaaagagga | 6360 |
| gcggctttgg gagtaatgga ggccctggga cactgccag acacatgac agagaggttt | 6420 |
| caggaagcca ttgacaacct cgccgtgctc atgcgagcag agactggaag caggccttat | 6480 |
| aaggcagcgg cagcccaact gccggagacc ctagagacca ttatgctctt aggtttgctg | 6540 |
| ggaacagttt cactggggat cttcttcgtc ttgatgcgga ataagggcat cgggaagatg | 6600 |
| ggctttggaa tggtaaccct tggggccagt catggctca tgtggctttc ggaaattgaa | 6660 |
| ccagccagaa ttgcatgtgt cctcattgtt gtgtttttat tactggtggt gctcataccc | 6720 |
| gagccagaga agcaaagatc tccccaagat aaccagatgg caattatcat catggtggca | 6780 |
| gtgggccttc taggtttgat aactgcaaac gaacttggat ggctgaaag aacaaaaaat | 6840 |
| gacatagctc atctaatggg aaggagagaa gaaggagcaa ccatgggatt ctcaatggac | 6900 |
| attgatctgc ggccagcctc cgcctgggct atctatgccg cattgacaac tctcatcacc | 6960 |
| ccagctgtcc aacatgcggt aaccacttca tacaacaact actccttaat ggcgatggcc | 7020 |
| acacaagctg gagtgctgtt tggcatgggc aaagggatgc cattttatgc atgggacctt | 7080 |
| ggagtcccgc tgctaatgat gggttgctat tcacaattaa caccctgac tctgatagta | 7140 |
| gctatcattc tgcttgtggc gcactacatg tacttgatcc caggcctaca agcggcagca | 7200 |
| gcgcgtgctg cccagaaaag gacagcagct ggcatcatga agaatcccgt tgtggatgga | 7260 |
| atagtggtaa ctgacattga cacaatgaca atagaccccc aggtggagaa gaagatggga | 7320 |
| caagtgttac tcatagcagt agccatctcc agtgctgtgc tgctgcggac cgcctgggga | 7380 |
| tgggggagg ctggagctct gatcacagca gcgacctcca ccttgtggga aggtctccca | 7440 |
| aacaaatact ggaactcctc tacagccacc tcactgtgca acatcttcag aggaagctat | 7500 |
| ctggcaggag cttcccttat ctatacagtg acgagaaacg ctggcctggt taagagacgt | 7560 |
| ggaggtggga cggagagac tctgggagag aagtggaaag ctcgtctgaa tcagatgtcg | 7620 |
| gccctggagt tctactctta taaaaagtca ggtatcactg aagtgtgtag agaggaggct | 7680 |
| cgccgtgccc tcaaggatgg agtggccaca ggaggacatg ccgtatcccg ggaagtgca | 7740 |
| aagctcagat ggttggtgga gagaggatat ctgcagccct atgggaaggt tgttgacctc | 7800 |
| ggatgtgca gaggggctg gagctattat gccgccacca tccgcaaagt gcaggaggtg | 7860 |
| agaggataca caaagggagg tcccggtcat gaagaaccca tgctggtgca aagctatggg | 7920 |
| tggaacatag ttcgtctcaa gagtggagtg gacgtcttcc acatggcggc tgagccgtgt | 7980 |
| gacactctgc tgtgtgacat aggtgagtca tcatctagtc ctgaagtgga agagacacga | 8040 |
| acactcagag tgctctctat ggtggggac tggcttgaaa aaagaccagg ggccttctgt | 8100 |
| ataaaggtgc tgtgcccata caccagcact atgatggaaa ccatgagcg actgcaacgt | 8160 |
| aggcatgggg gaggattagt cagagtgcca ttgtctcgca actccacaca tgagatgtac | 8220 |

-continued

```
tgggtctctg gggcaaagag caacatcata aaaagtgtgt ccaccacaag tcagctcctc    8280
ctgggacgca tggatggccc caggaggcca gtgaaatatg aggaggatgt gaacctcggc    8340
tcgggtacac gagctgtggc aagctgtgct gaggctccta acatgaaaat catcggcagg    8400
cgcattgaga gaatccgcaa tgaacatgca gaaacatggt tcttgatgaa aaccaccca     8460 tacaggacat gggcctacca tgggagctac gaagcccca cgcaaggatc agcgtcttcc    8520
ctcgtgaacg gggttgttag actcctgtca aagccttggg acgtggtgac tggagttaca    8580
ggaatagcca tgactgacac cacaccatac ggccaacaaa gagtcttcaa agaaaaagtg    8640
gacaccaggg tgccagatcc ccaagaaggc actcgccagg taatgaacat agtctcttcc    8700
tggctgtgga aggagctggg gaaacgcaag cggccacgcg tctgcaccaa agaagagttt    8760
atcaacaagg tgcgcagcaa tgcagcactg ggagcaatat ttgaagagga aaaagaatgg    8820
aagacggctg tggaagctgt gaatgatcca aggttttggg ccctagtgga tagggagaga    8880
gaacaccacc tgagaggaga gtgtcacagc tgtgtgtaca acatgatggg aaaaagagaa    8940
aagaagcaag gagagttcgg gaaagcaaaa ggtagccgcg ccatctggta catgtggttg    9000
ggagccagat tcttggagtt tgaagccctt ggattcttga acgaggacca ttggatggga    9060
agagaaaact caggaggtgg agtcgaaggg ttaggattgc aaagacttgg atacattcta    9120
gaagaaatga tcgggcacc aggaggaaag atgtacgcag atgacactgc tggctgggac    9180
acccgcatta gtaagtttga tctggagaat gaagctctga ttaccaacca aatggaggaa    9240
gggcacagaa ctctggcgtt ggccgtgatt aaatacacat accaaaacaa agtggtgaag    9300
gttctcagac cagctgaagg aggaaaaaca gttatggaca tcatttcaag acaagaccag    9360
agagggagtg gacaagttgt cacttatgct ctcaacacat tcaccaactt ggtggtgcag    9420
cttatccgga acatggaagc tgaggaagtg ttagagatgc aagacttatg gttgttgagg    9480
aagccagaga agtgaccag atggttgcag agcaatggat gggatagact caaacgaatg    9540
gcggtcagtg gagatgactg cgttgtgaag ccaatcgatg ataggtttgc acatgccctc    9600
aggttcttga tgacatggg aaaagttagg aaagacacac aggagtggaa accctcgact    9660
ggatggagca attgggaaga agtccgttc tgctcccacc acttcaacaa gctgtacctc    9720
aaggatggga gatccattgt ggtcccttgc cgccaccaag atgaactgat tggccgagct    9780
cgcgtctcac caggggcagg atggagcatc cgggagactg cctgtcttgc aaaatcatat    9840
gcgcagatgt ggcagctcct ttatttccac agaagagacc ttcgactgat ggctaatgcc    9900
atttgctcgg ctgtgccagt tgactgggta ccaactggga aaccacctg gtcaatccat    9960 ggaaagggag aatggatgac cactgaggac atgctcatgg tgtggaatag agtgtggatt   10020
gaggagaacg accatatgga ggacaagact cctgtaacaa aatggacaga cattccctat   10080 ctaggaaaa gggaggactt atggtgtgga tcccttatag ggcacagacc ccgcaccact   10140
tgggctgaaa acatcaaaga cacagtcaac atggtgcgca ggatcatagg tgatgaagaa   10200
aagtacatgg actatctatc cacccaagtc cgctacttgg gtgaggaagg gtccacaccc   10260
ggagtgttg                                                         10269
```

<210> SEQ ID NO 6
<211> LENGTH: 3423
<212> TYPE: PRT
<213> ORGANISM: Zika virus

<400> SEQUENCE: 6

-continued

```
Met Lys Asn Pro Lys Lys Ser Gly Gly Phe Arg Ile Val Asn Met
1               5                   10                  15

Leu Lys Arg Gly Val Ala Arg Val Asn Pro Leu Gly Gly Leu Lys Arg
            20                  25                  30

Leu Pro Ala Gly Leu Leu Leu Gly His Gly Pro Ile Arg Met Val Leu
            35                  40                  45

Ala Ile Leu Ala Phe Leu Arg Phe Thr Ala Ile Lys Pro Ser Leu Gly
    50                  55                  60

Leu Ile Asn Arg Trp Gly Ser Val Gly Lys Lys Glu Ala Met Glu Ile
65                  70                  75                  80

Ile Lys Lys Phe Lys Lys Asp Leu Ala Ala Met Leu Arg Ile Ile Asn
                85                  90                  95

Ala Arg Lys Glu Arg Lys Arg Gly Ala Asp Thr Ser Ile Gly Ile
                100                 105                 110

Ile Gly Leu Leu Leu Thr Thr Ala Met Ala Ala Glu Ile Thr Arg Arg
            115                 120                 125

Gly Ser Ala Tyr Tyr Met Tyr Leu Asp Arg Ser Asp Ala Gly Lys Ala
    130                 135                 140

Ile Ser Phe Ala Thr Thr Leu Gly Val Asn Lys Cys His Val Gln Ile
145                 150                 155                 160

Met Asp Leu Gly His Met Cys Asp Ala Thr Met Ser Tyr Glu Cys Pro
                165                 170                 175

Met Leu Asp Glu Gly Val Glu Pro Asp Asp Val Asp Cys Trp Cys Asn
            180                 185                 190

Thr Thr Ser Thr Trp Val Val Tyr Gly Thr Cys His His Lys Lys Gly
            195                 200                 205

Glu Ala Arg Arg Ser Arg Arg Ala Val Thr Leu Pro Ser His Ser Thr
    210                 215                 220

Arg Lys Leu Gln Thr Arg Ser Gln Thr Trp Leu Glu Ser Arg Glu Tyr
225                 230                 235                 240

Thr Lys His Leu Ile Lys Val Glu Asn Trp Ile Phe Arg Asn Pro Gly
                245                 250                 255

Phe Ala Leu Val Ala Val Ala Ile Ala Trp Leu Leu Gly Ser Ser Thr
            260                 265                 270

Ser Gln Lys Val Ile Tyr Leu Val Met Ile Leu Leu Ile Ala Pro Ala
    275                 280                 285

Tyr Ser Ile Arg Cys Ile Gly Val Ser Asn Arg Asp Phe Val Glu Gly
    290                 295                 300

Met Ser Gly Gly Thr Trp Val Asp Val Val Leu Glu His Gly Gly Cys
305                 310                 315                 320

Val Thr Val Met Ala Gln Asp Lys Pro Thr Val Asp Ile Glu Leu Val
                325                 330                 335

Thr Thr Thr Val Ser Asn Met Ala Glu Val Arg Ser Tyr Cys Tyr Glu
            340                 345                 350

Ala Ser Ile Ser Asp Met Ala Ser Asp Ser Arg Cys Pro Thr Gln Gly
    355                 360                 365

Glu Ala Tyr Leu Asp Lys Gln Ser Asp Thr Gln Tyr Val Cys Lys Arg
    370                 375                 380

Thr Leu Val Asp Arg Gly Trp Gly Asn Gly Cys Gly Leu Phe Gly Lys
385                 390                 395                 400

Gly Ser Leu Val Thr Cys Ala Lys Phe Thr Cys Ser Lys Lys Met Thr
            405                 410                 415

Gly Lys Ser Ile Gln Pro Glu Asn Leu Glu Tyr Arg Ile Met Leu Ser
```

```
            420                 425                 430
Val His Gly Ser Gln His Ser Gly Met Ile Val Asn Asp Thr Gly Tyr
            435                 440                 445
Glu Thr Asp Glu Asn Arg Ala Lys Val Glu Val Thr Pro Asn Ser Pro
450                 455                 460
Arg Ala Glu Ala Thr Leu Gly Gly Phe Gly Ser Leu Gly Leu Asp Cys
465                 470                 475                 480
Glu Pro Arg Thr Gly Leu Asp Phe Ser Asp Leu Tyr Tyr Leu Thr Met
                    485                 490                 495
Asn Asn Lys His Trp Leu Val His Lys Glu Trp Phe His Asp Ile Pro
            500                 505                 510
Leu Pro Trp His Ala Gly Ala Asp Thr Gly Thr Pro His Trp Asn Asn
        515                 520                 525
Lys Glu Ala Leu Val Glu Phe Lys Asp Ala His Ala Lys Arg Gln Thr
    530                 535                 540
Val Val Val Leu Gly Ser Gln Glu Gly Ala Val His Thr Ala Leu Ala
545                 550                 555                 560
Gly Ala Leu Glu Ala Glu Met Asp Gly Ala Lys Gly Lys Leu Phe Ser
                    565                 570                 575
Gly His Leu Lys Cys Arg Leu Lys Met Asp Lys Leu Arg Leu Lys Gly
                580                 585                 590
Val Ser Tyr Ser Leu Cys Thr Ala Ala Phe Thr Phe Thr Lys Val Pro
            595                 600                 605
Ala Glu Thr Leu His Gly Thr Val Thr Val Glu Val Gln Tyr Ala Gly
        610                 615                 620
Thr Asp Gly Pro Cys Lys Ile Pro Val Gln Met Ala Val Asp Met Gln
625                 630                 635                 640
Thr Leu Thr Pro Val Gly Arg Leu Ile Thr Ala Asn Pro Val Ile Thr
                    645                 650                 655
Glu Ser Thr Glu Asn Ser Lys Met Met Leu Glu Leu Asp Pro Pro Phe
                660                 665                 670
Gly Asp Ser Tyr Ile Val Ile Gly Val Gly Asp Lys Lys Ile Thr His
            675                 680                 685
His Trp His Arg Ser Gly Ser Thr Ile Gly Lys Ala Phe Glu Ala Thr
        690                 695                 700
Val Arg Gly Ala Lys Arg Met Ala Val Leu Gly Asp Thr Ala Trp Asp
705                 710                 715                 720
Phe Gly Ser Val Gly Gly Val Phe Asn Ser Leu Gly Lys Gly Ile His
                    725                 730                 735
Gln Ile Phe Gly Ala Ala Phe Lys Ser Leu Phe Gly Gly Met Ser Trp
                740                 745                 750
Phe Ser Gln Ile Leu Ile Gly Thr Leu Leu Val Trp Leu Gly Leu Asn
            755                 760                 765
Thr Lys Asn Gly Ser Ile Ser Leu Thr Cys Leu Ala Leu Gly Gly Val
        770                 775                 780
Met Ile Phe Leu Ser Thr Ala Val Ser Ala Asp Val Gly Cys Ser Val
785                 790                 795                 800
Asp Phe Ser Lys Lys Glu Thr Arg Cys Gly Thr Gly Val Phe Ile Tyr
                    805                 810                 815
Asn Asp Val Glu Ala Trp Arg Asp Arg Tyr Lys Tyr His Pro Asp Ser
                820                 825                 830
Pro Arg Arg Leu Ala Ala Ala Val Lys Gln Ala Trp Glu Glu Gly Ile
            835                 840                 845
```

```
Cys Gly Ile Ser Ser Val Ser Arg Met Glu Asn Ile Met Trp Lys Ser
850                 855                 860

Val Glu Gly Glu Leu Asn Ala Ile Leu Glu Glu Asn Gly Val Gln Leu
865                 870                 875                 880

Thr Val Val Gly Ser Val Lys Asn Pro Met Trp Arg Gly Pro Gln
                885                 890                 895

Arg Leu Pro Val Pro Val Asn Glu Leu Pro His Gly Trp Lys Ala Trp
                900                 905                 910

Gly Lys Ser Tyr Phe Val Arg Ala Ala Lys Thr Asn Asn Ser Phe Val
                915                 920                 925

Val Asp Gly Asp Thr Leu Lys Glu Cys Pro Leu Glu His Arg Ala Trp
930                 935                 940

Asn Ser Phe Leu Val Glu Asp His Gly Phe Gly Val Phe His Thr Ser
945                 950                 955                 960

Val Trp Leu Lys Val Arg Glu Asp Tyr Ser Leu Glu Cys Asp Pro Ala
                965                 970                 975

Val Ile Gly Thr Ala Val Lys Gly Arg Glu Ala Ala His Ser Asp Leu
                980                 985                 990

Gly Tyr Trp Ile Glu Ser Glu Lys Asn Asp Thr Trp Arg Leu Lys Arg
                995                 1000                1005

Ala His Leu Ile Glu Met Lys Thr Cys Glu Trp Pro Lys Ser His
1010                1015                1020

Thr Leu Trp Thr Asp Gly Val Glu Glu Ser Asp Leu Ile Ile Pro
1025                1030                1035

Lys Ser Leu Ala Gly Pro Leu Ser His His Asn Thr Arg Glu Gly
1040                1045                1050

Tyr Arg Thr Gln Val Lys Gly Pro Trp His Ser Glu Glu Leu Glu
1055                1060                1065

Ile Arg Phe Glu Glu Cys Pro Gly Thr Lys Val Tyr Val Glu Glu
1070                1075                1080

Thr Cys Gly Thr Arg Gly Pro Ser Leu Arg Ser Thr Thr Ala Ser
1085                1090                1095

Gly Arg Val Ile Glu Glu Trp Cys Cys Arg Glu Cys Thr Met Pro
1100                1105                1110

Pro Leu Ser Phe Arg Ala Lys Asp Gly Cys Trp Tyr Gly Met Glu
1115                1120                1125

Ile Arg Pro Arg Lys Glu Pro Glu Ser Asn Leu Val Arg Ser Met
1130                1135                1140

Val Thr Ala Gly Ser Thr Asp His Met Asp His Phe Ser Leu Gly
1145                1150                1155

Val Leu Val Ile Leu Leu Met Val Gln Glu Gly Leu Lys Lys Arg
1160                1165                1170

Met Thr Thr Lys Ile Ile Met Ser Thr Ser Met Ala Val Leu Val
1175                1180                1185

Val Met Ile Leu Gly Gly Phe Ser Met Ser Asp Leu Ala Lys Leu
1190                1195                1200

Val Ile Leu Met Gly Ala Thr Phe Ala Glu Met Asn Thr Gly Gly
1205                1210                1215

Asp Val Ala His Leu Ala Leu Val Ala Ala Phe Lys Val Arg Pro
1220                1225                1230

Ala Leu Leu Val Ser Phe Ile Phe Arg Ala Asn Trp Thr Pro Arg
1235                1240                1245
```

-continued

| | | | | | | | | | | | | | |
|---|---|---|---|---|---|---|---|---|---|---|---|---|---|
|Glu|Ser|Met|Leu|Leu|Ala|Leu|Ala|Ser|Cys|Leu|Leu|Gln|Thr|Ala|
| |1250| | | |1255| | | |1260| | | | |

Glu Ser Met Leu Leu Ala Leu Ala Ser Cys Leu Leu Gln Thr Ala
    1250                1255               1260

Ile Ser Ala Leu Glu Gly Asp Leu Met Val Leu Ile Asn Gly Phe
    1265                1270               1275

Ala Leu Ala Trp Leu Ala Ile Arg Ala Met Ala Val Pro Arg Thr
    1280                1285               1290

Asp Asn Ile Ala Leu Pro Ile Leu Ala Ala Leu Thr Pro Leu Ala
    1295                1300               1305

Arg Gly Thr Leu Leu Val Ala Trp Arg Ala Gly Leu Ala Thr Cys
    1310                1315               1320

Gly Gly Ile Met Leu Leu Ser Leu Lys Gly Lys Gly Ser Val Lys
    1325                1330               1335

Lys Asn Leu Pro Phe Val Met Ala Leu Gly Leu Thr Ala Val Arg
    1340                1345               1350

Val Val Asp Pro Ile Asn Val Val Gly Leu Leu Leu Leu Thr Arg
    1355                1360               1365

Ser Gly Lys Arg Ser Trp Pro Pro Ser Glu Val Leu Thr Ala Val
    1370                1375               1380

Gly Leu Ile Cys Ala Leu Ala Gly Gly Phe Ala Lys Ala Asp Ile
    1385                1390               1395

Glu Met Ala Gly Pro Met Ala Ala Val Gly Leu Leu Ile Val Ser
    1400                1405               1410

Tyr Val Val Ser Gly Lys Ser Val Asp Met Tyr Ile Glu Arg Ala
    1415                1420               1425

Gly Asp Ile Thr Trp Glu Lys Asp Ala Glu Val Thr Gly Asn Ser
    1430                1435               1440

Pro Arg Leu Asp Val Ala Leu Asp Glu Ser Gly Asp Phe Ser Leu
    1445                1450               1455

Val Glu Glu Asp Gly Pro Pro Met Arg Glu Ile Ile Leu Lys Val
    1460                1465               1470

Val Leu Met Ala Ile Cys Gly Met Asn Pro Ile Ala Ile Pro Phe
    1475                1480               1485

Ala Ala Gly Ala Trp Tyr Val Tyr Val Lys Thr Gly Lys Arg Ser
    1490                1495               1500

Gly Ala Leu Trp Asp Val Pro Ala Pro Lys Glu Val Lys Lys Gly
    1505                1510               1515

Glu Thr Thr Asp Gly Val Tyr Arg Val Met Thr Arg Arg Leu Leu
    1520                1525               1530

Gly Ser Thr Gln Val Gly Val Gly Val Met Gln Glu Gly Val Phe
    1535                1540               1545

His Thr Met Trp His Val Thr Lys Gly Ala Ala Leu Arg Ser Gly
    1550                1555               1560

Glu Gly Arg Leu Asp Pro Tyr Trp Gly Asp Val Lys Gln Asp Leu
    1565                1570               1575

Val Ser Tyr Cys Gly Pro Trp Lys Leu Asp Ala Ala Trp Asp Gly
    1580                1585               1590

Leu Ser Glu Val Gln Leu Leu Ala Val Pro Pro Gly Glu Arg Ala
    1595                1600               1605

Arg Asn Ile Gln Thr Leu Pro Gly Ile Phe Lys Thr Lys Asp Gly
    1610                1615               1620

Asp Ile Gly Ala Val Ala Leu Asp Tyr Pro Ala Gly Thr Ser Gly
    1625                1630               1635

Ser Pro Ile Leu Asp Lys Cys Gly Arg Val Ile Gly Leu Tyr Gly

-continued

```
            1640                1645                1650
Asn Gly Val Val Ile Lys Asn Gly Ser Tyr Val Ser Ala Ile Thr
            1655                1660                1665
Gln Gly Lys Arg Glu Glu Glu Thr Pro Val Glu Cys Phe Glu Pro
            1670                1675                1680
Ser Met Leu Lys Lys Lys Gln Leu Thr Val Leu Asp Leu His Pro
            1685                1690                1695
Gly Ala Gly Lys Thr Arg Arg Val Leu Pro Glu Ile Val Arg Glu
            1700                1705                1710
Ala Ile Lys Lys Arg Leu Arg Thr Val Ile Leu Ala Pro Thr Arg
            1715                1720                1725
Val Val Ala Ala Glu Met Glu Glu Ala Leu Arg Gly Leu Pro Val
            1730                1735                1740
Arg Tyr Met Thr Thr Ala Val Asn Val Thr His Ser Gly Thr Glu
            1745                1750                1755
Ile Val Asp Leu Met Cys His Ala Thr Phe Thr Ser Arg Leu Leu
            1760                1765                1770
Gln Pro Ile Arg Val Pro Asn Tyr Asn Leu Tyr Ile Met Asp Glu
            1775                1780                1785
Ala His Phe Thr Asp Pro Ser Ser Ile Ala Ala Arg Gly Tyr Ile
            1790                1795                1800
Ser Thr Arg Val Glu Met Gly Glu Ala Ala Ile Phe Met Thr
            1805                1810                1815
Ala Thr Pro Pro Gly Thr Arg Asp Ala Phe Pro Asp Ser Asn Ser
            1820                1825                1830
Pro Ile Met Asp Thr Glu Val Glu Val Pro Glu Arg Ala Trp Ser
            1835                1840                1845
Ser Gly Phe Asp Trp Val Thr Asp His Ser Gly Lys Thr Val Trp
            1850                1855                1860
Phe Val Pro Ser Val Arg Asn Gly Asn Glu Ile Ala Ala Cys Leu
            1865                1870                1875
Thr Lys Ala Gly Lys Arg Val Ile Gln Leu Ser Arg Lys Thr Phe
            1880                1885                1890
Glu Thr Glu Phe Gln Lys Thr Lys Asn Gln Glu Trp Asp Phe Val
            1895                1900                1905
Ile Thr Thr Asp Ile Ser Glu Met Gly Ala Asn Phe Lys Ala Asp
            1910                1915                1920
Arg Val Ile Asp Ser Arg Arg Cys Leu Lys Pro Val Ile Leu Asp
            1925                1930                1935
Gly Glu Arg Val Ile Leu Ala Gly Pro Met Pro Val Thr His Ala
            1940                1945                1950
Ser Ala Ala Gln Arg Arg Gly Arg Ile Gly Arg Asn Pro Asn Lys
            1955                1960                1965
Pro Gly Asp Glu Tyr Met Tyr Gly Gly Gly Cys Ala Glu Thr Asp
            1970                1975                1980
Glu Gly His Ala His Trp Leu Glu Ala Arg Met Leu Leu Asp Asn
            1985                1990                1995
Ile Tyr Leu Gln Asp Gly Leu Ile Ala Ser Leu Tyr Arg Pro Glu
            2000                2005                2010
Ala Asp Lys Val Ala Ala Ile Glu Gly Glu Phe Lys Leu Arg Thr
            2015                2020                2025
Glu Gln Arg Lys Thr Phe Val Glu Leu Met Lys Arg Gly Asp Leu
            2030                2035                2040
```

-continued

```
Pro Val Trp Leu Ala Tyr Gln Val Ala Ser Ala Gly Ile Thr Tyr
    2045                2050                2055

Thr Asp Arg Arg Trp Cys Phe Asp Gly Thr Thr Asn Asn Thr Ile
    2060                2065                2070

Met Glu Asp Ser Val Pro Ala Glu Val Trp Thr Lys Tyr Gly Glu
    2075                2080                2085

Lys Arg Val Leu Lys Pro Arg Trp Met Asp Ala Arg Val Cys Ser
    2090                2095                2100

Asp His Ala Ala Leu Lys Ser Phe Lys Glu Phe Ala Ala Gly Lys
    2105                2110                2115

Arg Gly Ala Ala Leu Gly Val Met Glu Ala Leu Gly Thr Leu Pro
    2120                2125                2130

Gly His Met Thr Glu Arg Phe Gln Glu Ala Ile Asp Asn Leu Ala
    2135                2140                2145

Val Leu Met Arg Ala Glu Thr Gly Ser Arg Pro Tyr Lys Ala Ala
    2150                2155                2160

Ala Ala Gln Leu Pro Glu Thr Leu Glu Thr Ile Met Leu Leu Gly
    2165                2170                2175

Leu Leu Gly Thr Val Ser Leu Gly Ile Phe Phe Val Leu Met Arg
    2180                2185                2190

Asn Lys Gly Ile Gly Lys Met Gly Phe Gly Met Val Thr Leu Gly
    2195                2200                2205

Ala Ser Ala Trp Leu Met Trp Leu Ser Glu Ile Glu Pro Ala Arg
    2210                2215                2220

Ile Ala Cys Val Leu Ile Val Val Phe Leu Leu Leu Val Val Leu
    2225                2230                2235

Ile Pro Glu Pro Glu Lys Gln Arg Ser Pro Gln Asp Asn Gln Met
    2240                2245                2250

Ala Ile Ile Ile Met Val Ala Val Gly Leu Leu Gly Leu Ile Thr
    2255                2260                2265

Ala Asn Glu Leu Gly Trp Leu Glu Arg Thr Lys Asn Asp Ile Ala
    2270                2275                2280

His Leu Met Gly Arg Arg Glu Glu Gly Ala Thr Met Gly Phe Ser
    2285                2290                2295

Met Asp Ile Asp Leu Arg Pro Ala Ser Ala Trp Ala Ile Tyr Ala
    2300                2305                2310

Ala Leu Thr Thr Leu Ile Thr Pro Ala Val Gln His Ala Val Thr
    2315                2320                2325

Thr Ser Tyr Asn Asn Tyr Ser Leu Met Ala Met Ala Thr Gln Ala
    2330                2335                2340

Gly Val Leu Phe Gly Met Gly Lys Gly Met Pro Phe Tyr Ala Trp
    2345                2350                2355

Asp Leu Gly Val Pro Leu Leu Met Met Gly Cys Tyr Ser Gln Leu
    2360                2365                2370

Thr Pro Leu Thr Leu Ile Val Ala Ile Ile Leu Leu Val Ala His
    2375                2380                2385

Tyr Met Tyr Leu Ile Pro Gly Leu Gln Ala Ala Ala Arg Ala
    2390                2395                2400

Ala Gln Lys Arg Thr Ala Ala Gly Ile Met Lys Asn Pro Val Val
    2405                2410                2415

Asp Gly Ile Val Val Thr Asp Ile Asp Thr Met Thr Ile Asp Pro
    2420                2425                2430
```

-continued

```
Gln Val Glu Lys Lys Met Gly Gln Val Leu Leu Ile Ala Val Ala
2435                2440                2445

Ile Ser Ser Ala Val Leu Leu Arg Thr Ala Trp Gly Trp Gly Glu
2450                2455                2460

Ala Gly Ala Leu Ile Thr Ala Ala Thr Ser Thr Leu Trp Glu Gly
2465                2470                2475

Ser Pro Asn Lys Tyr Trp Asn Ser Ser Thr Ala Thr Ser Leu Cys
2480                2485                2490

Asn Ile Phe Arg Gly Ser Tyr Leu Ala Gly Ala Ser Leu Ile Tyr
2495                2500                2505

Thr Val Thr Arg Asn Ala Gly Leu Val Lys Arg Arg Gly Gly Gly
2510                2515                2520

Thr Gly Glu Thr Leu Gly Glu Lys Trp Lys Ala Arg Leu Asn Gln
2525                2530                2535

Met Ser Ala Leu Glu Phe Tyr Ser Tyr Lys Lys Ser Gly Ile Thr
2540                2545                2550

Glu Val Cys Arg Glu Ala Arg Arg Ala Leu Lys Asp Gly Val
2555                2560                2565

Ala Thr Gly Gly His Ala Val Ser Arg Gly Ser Ala Lys Leu Arg
2570                2575                2580

Trp Leu Val Glu Arg Gly Tyr Leu Gln Pro Tyr Gly Lys Val Val
2585                2590                2595

Asp Leu Gly Cys Gly Arg Gly Gly Trp Ser Tyr Tyr Ala Ala Thr
2600                2605                2610

Ile Arg Lys Val Gln Glu Val Arg Gly Tyr Thr Lys Gly Gly Pro
2615                2620                2625

Gly His Glu Glu Pro Met Leu Val Gln Ser Tyr Gly Trp Asn Ile
2630                2635                2640

Val Arg Leu Lys Ser Gly Val Asp Val Phe His Met Ala Ala Glu
2645                2650                2655

Pro Cys Asp Thr Leu Leu Cys Asp Ile Gly Glu Ser Ser Ser Ser
2660                2665                2670

Pro Glu Val Glu Glu Thr Arg Thr Leu Arg Val Leu Ser Met Val
2675                2680                2685

Gly Asp Trp Leu Glu Lys Arg Pro Gly Ala Phe Cys Ile Lys Val
2690                2695                2700

Leu Cys Pro Tyr Thr Ser Thr Met Met Glu Thr Met Glu Arg Leu
2705                2710                2715

Gln Arg Arg His Gly Gly Gly Leu Val Arg Val Pro Leu Ser Arg
2720                2725                2730

Asn Ser Thr His Glu Met Tyr Trp Val Ser Gly Ala Lys Ser Asn
2735                2740                2745

Ile Ile Lys Ser Val Ser Thr Thr Ser Gln Leu Leu Leu Gly Arg
2750                2755                2760

Met Asp Gly Pro Arg Arg Pro Val Lys Tyr Glu Glu Asp Val Asn
2765                2770                2775

Leu Gly Ser Gly Thr Arg Ala Val Ala Ser Cys Ala Glu Ala Pro
2780                2785                2790

Asn Met Lys Ile Ile Gly Arg Arg Ile Glu Arg Ile Arg Asn Glu
2795                2800                2805

His Ala Glu Thr Trp Phe Leu Asp Glu Asn His Pro Tyr Arg Thr
2810                2815                2820

Trp Ala Tyr His Gly Ser Tyr Glu Ala Pro Thr Gln Gly Ser Ala
```

-continued

```
            2825                2830                2835

Ser  Ser  Leu  Val  Asn  Gly  Val  Arg  Leu  Leu  Ser  Lys  Pro  Trp
     2840                2845                2850

Asp  Val  Val  Thr  Gly  Val  Thr  Gly  Ile  Ala  Met  Thr  Asp  Thr  Thr
     2855                2860                2865

Pro  Tyr  Gly  Gln  Gln  Arg  Val  Phe  Lys  Glu  Lys  Val  Asp  Thr  Arg
     2870                2875                2880

Val  Pro  Asp  Pro  Gln  Glu  Gly  Thr  Arg  Gln  Val  Met  Asn  Ile  Val
     2885                2890                2895

Ser  Ser  Trp  Leu  Trp  Lys  Glu  Leu  Gly  Lys  Arg  Lys  Arg  Pro  Arg
     2900                2905                2910

Val  Cys  Thr  Lys  Glu  Glu  Phe  Ile  Asn  Lys  Val  Arg  Ser  Asn  Ala
     2915                2920                2925

Ala  Leu  Gly  Ala  Ile  Phe  Glu  Glu  Lys  Glu  Trp  Lys  Thr  Ala
     2930                2935                2940

Val  Glu  Ala  Val  Asn  Asp  Pro  Arg  Phe  Trp  Ala  Leu  Val  Asp  Arg
     2945                2950                2955

Glu  Arg  Glu  His  His  Leu  Arg  Gly  Glu  Cys  His  Ser  Cys  Val  Tyr
     2960                2965                2970

Asn  Met  Met  Gly  Lys  Arg  Glu  Lys  Lys  Gln  Gly  Glu  Phe  Gly  Lys
     2975                2980                2985

Ala  Lys  Gly  Ser  Arg  Ala  Ile  Trp  Tyr  Met  Trp  Leu  Gly  Ala  Arg
     2990                2995                3000

Phe  Leu  Glu  Phe  Glu  Ala  Leu  Gly  Phe  Leu  Asn  Glu  Asp  His  Trp
     3005                3010                3015

Met  Gly  Arg  Glu  Asn  Ser  Gly  Gly  Gly  Val  Glu  Gly  Leu  Gly  Leu
     3020                3025                3030

Gln  Arg  Leu  Gly  Tyr  Ile  Leu  Glu  Glu  Met  Asn  Arg  Ala  Pro  Gly
     3035                3040                3045

Gly  Lys  Met  Tyr  Ala  Asp  Asp  Thr  Ala  Gly  Trp  Asp  Thr  Arg  Ile
     3050                3055                3060

Ser  Lys  Phe  Asp  Leu  Glu  Asn  Glu  Ala  Leu  Ile  Thr  Asn  Gln  Met
     3065                3070                3075

Glu  Glu  Gly  His  Arg  Thr  Leu  Ala  Leu  Ala  Val  Ile  Lys  Tyr  Thr
     3080                3085                3090

Tyr  Gln  Asn  Lys  Val  Val  Lys  Val  Leu  Arg  Pro  Ala  Glu  Gly  Gly
     3095                3100                3105

Lys  Thr  Val  Met  Asp  Ile  Ile  Ser  Arg  Gln  Asp  Gln  Arg  Gly  Ser
     3110                3115                3120

Gly  Gln  Val  Val  Thr  Tyr  Ala  Leu  Asn  Thr  Phe  Thr  Asn  Leu  Val
     3125                3130                3135

Val  Gln  Leu  Ile  Arg  Asn  Met  Glu  Ala  Glu  Glu  Val  Leu  Glu  Met
     3140                3145                3150

Gln  Asp  Leu  Trp  Leu  Leu  Arg  Lys  Pro  Glu  Lys  Val  Thr  Arg  Trp
     3155                3160                3165

Leu  Gln  Ser  Asn  Gly  Trp  Asp  Arg  Leu  Lys  Arg  Met  Ala  Val  Ser
     3170                3175                3180

Gly  Asp  Asp  Cys  Val  Val  Lys  Pro  Ile  Asp  Asp  Arg  Phe  Ala  His
     3185                3190                3195

Ala  Leu  Arg  Phe  Leu  Asn  Asp  Met  Gly  Lys  Val  Arg  Lys  Asp  Thr
     3200                3205                3210

Gln  Glu  Trp  Lys  Pro  Ser  Thr  Gly  Trp  Ser  Asn  Trp  Glu  Glu  Val
     3215                3220                3225
```

```
Pro Phe Cys Ser His His Phe Asn Lys Leu Tyr Leu Lys Asp Gly
    3230                3235                3240

Arg Ser Ile Val Val Pro Cys Arg His Gln Asp Glu Leu Ile Gly
    3245                3250                3255

Arg Ala Arg Val Ser Pro Gly Ala Gly Trp Ser Ile Arg Glu Thr
    3260                3265                3270

Ala Cys Leu Ala Lys Ser Tyr Ala Gln Met Trp Gln Leu Leu Tyr
    3275                3280                3285

Phe His Arg Arg Asp Leu Arg Leu Met Ala Asn Ala Ile Cys Ser
    3290                3295                3300

Ala Val Pro Val Asp Trp Val Pro Thr Gly Arg Thr Thr Trp Ser
    3305                3310                3315

Ile His Gly Lys Gly Glu Trp Met Thr Thr Glu Asp Met Leu Met
    3320                3325                3330

Val Trp Asn Arg Val Trp Ile Glu Glu Asn Asp His Met Glu Asp
    3335                3340                3345

Lys Thr Pro Val Thr Lys Trp Thr Asp Ile Pro Tyr Leu Gly Lys
    3350                3355                3360

Arg Glu Asp Leu Trp Cys Gly Ser Leu Ile Gly His Arg Pro Arg
    3365                3370                3375

Thr Thr Trp Ala Glu Asn Ile Lys Asp Thr Val Asn Met Val Arg
    3380                3385                3390

Arg Ile Ile Gly Asp Glu Glu Lys Tyr Met Asp Tyr Leu Ser Thr
    3395                3400                3405

Gln Val Arg Tyr Leu Gly Glu Glu Gly Ser Thr Pro Gly Val Leu
    3410                3415                3420

<210> SEQ ID NO 7
<211> LENGTH: 10269
<212> TYPE: DNA
<213> ORGANISM: Zika virus
<220> FEATURE:
<221> NAME/KEY: misc_feature
<222> LOCATION: (4429)..(4429)
<223> OTHER INFORMATION: n is a, c, g, t or u
<220> FEATURE:
<221> NAME/KEY: misc_feature
<222> LOCATION: (6882)..(6882)
<223> OTHER INFORMATION: n is a, c, g, t or u

<400> SEQUENCE: 7
atgaaaaacc caaagaagaa atccggagga ttccggattg tcaatatgct aaaacgcgga    60
gtagcccgtg tgagccccct tgggggcttg aagaggctgc cagccggact tctgctgggt   120
catgggccca tcaggatggt cttggcgatt ctagcctttt tgagattcac ggcaatcaag   180
ccatcactgg gtctcatcaa tagatggggt tcagtgggga aaaagaggc tatggaaata    240 ataaagaagt ttaagaaaga tctggctgcc atgctgagaa taatcaatgc taggaaggag   300
aagaagagac gaggcacaga tactagtgtc ggaattgttg cctcctgct gaccacagcc    360 atggcagtgg aggtcactag acgtgggaat gcatactata tgtacttgga cagaagcgat   420
gctggggagg ccatatcttt tccaaccaca atggggatga taagtgttta tacagatc     480 atggatcttg acacatgtg tgatgccacc atgagctatg aatgccctat gctggatgag   540
ggggtagaac cagatgacgt cgattgttgg tgcaacacga cgtcaacttg ggttgtgtac   600
ggaacctgcc accacaaaaa aggtgaagca cggagatcta aagagctgt gacgctcccc   660 tcccattcca ctaggaagct gcaaacgcgg tcgcagacct ggttggaatc aagagaatac   720
```

```
acaaagcacc tgattagagt cgaaaattgg atattcagga accctggctt cgcgttagca      780
gcagctgcca tcgcttggct tttgggaagc tcaacgagcc aaaaagtcat atacttggtc      840
atgatactgc tgattgcccc ggcatacagc atcaggtgca taggagtcag caatagggac      900
tttgtggaag gtatgtcagg tgggacttgg gttgatgttg tcttggaaca tggaggttgt      960
gttaccgtaa tggcacagga caaaccgact gtcgacatag agctggttac aacaacagtc     1020
agcaacatgg cggaggtaag atcctactgc tatgaggcat caatatcgga catggcttcg     1080
gacagccgct gcccaacaca aggtgaagcc taccttgaca agcaatcaga cactcaatat     1140
gtctgcaaaa gaacgttagt ggacagaggc tggggaaatg gatgtggact ttttggcaaa     1200
gggagcctgg tgacatgcgc taagtttgct tgctctaaga aaatgaccgg gaagagcatc     1260
cagccagaga atctggagta ccggataatg ctgtcagttc atggctccca gcacagtggg     1320
atgatcgtta atgatacagg acatgaaact gatgagaata gagcgaaggt tgagataacg     1380
cccaattcac caagagccga agccaccctg ggggttttg gaagcctagg acttgattgt     1440
gaaccgagga caggccttga cttttcagat ttgtattact tgactatgaa taacaagcac     1500
tggttggttc acaaggagtg gttccacgac attccattac cttggcatgc tggggcagac     1560
accggaactc cacactggaa caacaaagaa gcactggtag agttcaagga cgcacatgcc     1620
aaaaggcaga ctgtcgtggt tctagggagt caagaaggag cagttcacac ggcccttgct     1680
ggagctctgg aggctgagat ggatggtgca aagggaaggc tgtcctctgg ccacttgaaa     1740
tgtcgcctga aaatggataa acttagattg aagggcgtgt catactcctt gtgtaccgca     1800
gcgttcacat tcactaagat cccggctgaa acactgcacg ggacagtcac agtggaggta     1860
cagtacgcag ggacagatgg accttgcaag gttccagctc agatggcggt ggacatgcaa     1920
actctgaccc cagttgggag gttgataacc gctaaccctg taatcactga aagcactgag     1980
aactccaaga tgatgctgga actggatcca ccatttgggg actcttacat tgtcatagga     2040 gtcgggaaa agaagatcac ccaccactgg cacaggagtg gcagcaccat tggaaaagca     2100
tttgaagcca ctgtgagagg tgccaagaga atggcagtct gggagacac agcctgggac     2160 tttggatcag ttgggggtgc tctcaactca ctgggcaagg gcatccatca aattttgga     2220 gcagctttca atcattgtt tggaggaatg tcctggttct cacaaattct cattggaacg     2280
ttgctggtgt ggttgggtct gaatacaaag aatggatcta tttcccttat gtgcttggcc     2340
ttagggggag tgttgatctt cttatccaca gccgtctctg ctgatgtggg gtgctcggtg     2400
gacttctcaa agaaggaaac gagatgcggt acagggggtgt tcgtctataa cgacgttgaa     2460
gcttggaggg acaggtacaa gtaccatcct gactcccctc gtagattggc agcagcagtc     2520
aagcaagcct gggaagatgg gatctgtggg atctcctctg tttcaagaat ggaaaacatc     2580
atgtggagat cagtagaagg ggagctcaac gcaatcctgg aagagaatgg agttcaactg     2640
acggtcgttg tgggatctgt aaaaaacccc atgtggagag gtccacagag attgcccgtg     2700
cctgtgaacg agctgcccca tggctggaag gcttggggga atcgtacttt cgtcagggca     2760
gcaaagacaa ataacagctt tgtcgtggat ggtgacacac tgaaggaatg cccactcaaa     2820
catagagcat ggaacagctt tcttgtggag gatcatgggt tcggggtatt tcacactagt     2880
gtctggctca aggttagaga agattattca ttagagtgtg atccagccgt cattggaaca     2940
gccgctaagg gaaaggaggc tgtgcacagt gatctaggct actggattga gagtgagaag     3000
aacgacacat ggaggctgaa gagggcccac ctgatcgaga tgaaaacatg tgaatggcca     3060
```

-continued

| | |
|---|---|
| aagtcccaca cattgtggac agatggaata gaagaaagtg atctgatcat acccaagtct | 3120 |
| ttagctgggc cactcagcca tcacaacacc agagagggct acaggaccca aatgaaaggg | 3180 |
| ccatggcata gtgaagagct tgaaattcgg tttgaggaat gcccaggcac taaggtccac | 3240 |
| gtggaggaaa catgtggaac aagaggacca tctctgagat caaccactgc aagcggaagg | 3300 |
| gtgatcgagg aatggtgctg cagggagtgc acaatgcccc cactgtcgtt ccgggctaaa | 3360 |
| gatggttgtt ggtatggaat ggagataagg cccaggaaag aaccagaaag taacttagta | 3420 |
| aggtcaatgg tgactgcagg atcaactgat cacatggatc acttctccct ggagtgctt | 3480 |
| gtgattctgc tcatggtaca ggaagggcta agaagagaa tgaccacaaa gatcatcata | 3540 |
| agcacatcaa tggcagtgct ggtagctatg atcctgggag attttcaat gagtgacctg | 3600 |
| gctaagcttg caattttgat gggtgccacc ttcgcgaaaa tgaacactgg aggagatgtt | 3660 |
| gctcatctgg cgctgatagc ggcattcaaa gtcagacctg cgttgctggt atctttcatt | 3720 |
| ttcagagcta attggacacc ccgtgagagc atgctgctgg ccttggcctc gtgtcttctg | 3780 |
| caaactgcga tctccgcctt ggaaggcgac ctgatggttc ccatcaatgg ttttgctttg | 3840 |
| gcctggttgg caatacgagc gatggttgtt ccacgcactg acaacatcac cttggcaatc | 3900 |
| ctggctgctc tgacaccact ggcccggggc acactgcttg tggcgtggag agcaggcctt | 3960 |
| gctacttgcg gggggttcat gctcctttct ctgaagggga aaggcagtgt gaagaagaac | 4020 |
| ttaccatttg tcatggccct gggactaacc gctgtgaggc tggtcgaccc catcaacgtg | 4080 |
| gtgggactgc tgttgctcac aaggagtggg aagcggagct ggcccccctag tgaagtactc | 4140 |
| acagctgttg gcctgatatg cgcattggct ggagggttcg ccaaggcgga tatagagatg | 4200 |
| gctgggccca tggccgcggt cggtctgcta attgtcagtt acgtggtctc aggaaagagt | 4260 |
| gtggacatgt acattgaaag agcaggtgac atcacatggg aaaaagatgc ggaagtcact | 4320 |
| ggaaacagtc ccggctcga tgtggcacta gatgagagtg gtgatttctc cctagtggag | 4380 |
| gatgatggtc ccccatgag agagatcata ctcaaagtgg tcctgatgnc catctgtggc | 4440 |
| atgaacccaa tagccatacc ctttgcagct ggagcgtggt acgtgtatgt gaagactgga | 4500 |
| aaaaggagtg tgctctatg ggatgtgcct gctcccaagg aagtaaaaaa gggggagacc | 4560 |
| acagatggag tgtacagagt aatgactcgt agactgctag gttcaacaca agttggagtg | 4620 |
| ggagtcatgc aagagggggt cttccacact atgtggcacg tcacaaaagg atccgcgctg | 4680 |
| agaagcggtg aagggagact tgatccatac tggggagatg tcaagcagga tctggtgtca | 4740 |
| tactgtggtc catggaagct agatgccgcc tgggacgggc acagcgaggt gcagctcttg | 4800 |
| gccgtgcccc ccggagagag agcgaggaac atccagactc tgcccggaat atttaagaca | 4860 |
| aaggatgggg acattggagc agttgcgctg gactacccag caggaacttc aggatctcca | 4920 |
| atcctagata agtgtgggag agtgatagga ctctatggta tggggtcgt gatcaaaaat | 4980 |
| gggagttacg ttagtgccat cacccaaggg aggaggagg aagagactcc tgttgagtgc | 5040 |
| ttcgagcctt cgatgctgaa gaagaagcag ctaactgtct tagacttgca tcctggagct | 5100 |
| gggaaaacca ggagagttct tcctgaaata gtccgtgaag ccataaaaac aagactccgc | 5160 |
| actgtgatct tagctccaac cagggttgtc gctgctgaaa tggaggaagc ccttagaggg | 5220 |
| cttccagtgc gttatatgac aacagcagtc aatgtcaccc attctgggac agaaatcgtt | 5280 |
| gacttaatgt gccatgccac cttcacttca cgtctactac agccaatcag agtccccaac | 5340 |
| tataatctgt atattatgga tgaggcccac ttcacagatc cctcaagtat agcagcaaga | 5400 |
| ggatacattt caacaagggt tgagatgggc gaggcggctg ccatcttcat gactgccacg | 5460 |

```
ccaccaggaa cccgtgacgc attcccggac tccaactcac caattatgga caccgaagtg   5520
gaagtcccag agagagcctg gagctcaggc tttgattggg tgacggatca ttctggaaaa   5580
acagtttggt ttgttccaag cgtgaggaat ggcaatgaga tcgcagcttg tctgacaaag   5640
gctggaaaac gggtcataca gctcagcaga aagactttg  agacagagtt ccagaaaaca   5700
aaacatcaag agtgggactt cgtcgtgaca actgacattt cagagatggg cgccaacttt   5760
aaagctgacc gtgtcataga ttccaggaga tgcctaaagc cggtcatact tgatggcgag   5820
agagtcattc tggctggacc catgcctgtc acacatgcca gcgctgccca gaggagggg    5880
cgcataggca ggaaccccaa caaacctgga gatgagtatc tgtatggagg tgggtgcgca   5940
gagactgatg aagaccatgc acactggctt gaagcaagaa tgcttcttga caacatttac   6000
ctccaagatg gcctcatagc ctcgctctat cgacctgagg ccgacaaagt agcagctatt   6060
gagggagagt tcaagcttag gacggagcaa aggaagacct tgtggaact  catgaaaaga   6120
ggagatcttc ctgtttggct ggcctatcag gttgcatctg ccggaataac ctacacagat   6180
agaagatggt gctttgatgg cacgaccaac aacaccataa tggaagacag tgtgccggca   6240
gaggtgtgga ccagatacgg agagaaaaga gtgctcaaac cgaggtggat ggacgccaga   6300
gtttgttcag atcatgcggc cctgaagtca ttcaaagagt ttgccgctgg gaaaagagga   6360
gcggcctttg gagtgatgga agccctggga acactgccag acatatgac  agagagattc   6420
caggaggcca ttgacaacct cgctgtgctc atgcgggcag agactggaag caggccctac   6480
aaagccgcgg cggcccaatt accggagacc ctagagacta tcatgctttt ggggttgctg   6540
ggaacagtct cgctgggaat ctttttcgtc ttgatgcgga acaagggcat agggaagatg   6600
ggctttggaa tggtgactct tggggccagc gcatggctta tgtggctctc ggaaattgag   6660
ccagccagaa ttgcatgtgt cctcattgtt gtgttcctat tgctggtggt gctcataccc   6720
gagccagaaa agcaaagatc tccccaggac aaccaaatgg caatcatcat catggtagca   6780
gtgggtcttc tgggcttgat taccgccaat gaactcggat ggttggagag aacaaagagt   6840
gacctaagcc atctaatggg aaggagagag gaggggcaa  cnataggatt ctcaatggac   6900
attgacctgc ggccagcctc agcttgggct atctatgctg ctctgacaac tttcattacc   6960
ccagccgtcc aacatgcagt gaccacttca tacaacaact actccttaat ggcgatggcc   7020
acgcaagctg gagtgttgtt cggtatgggt aaagggatgc cattctatgc atgggacttt   7080
ggagtcccgc tgctaatgat aggttgctac tcacaattaa cacccctgac cctaatagtg   7140
gccatcattt tgctcgtggc gcactacatg tacttgatcc cagggctgca ggcagcagct   7200
gcgcgtgctg cccagaagag aacggcagct ggcatcatga agaaccctgt tgtggatgga   7260
atagtggtga ctgacattga cacaatgaca attgaccccc aagtgagaa  aaagatggga   7320
caggtgctac tcatagcagt agctgtctcc agcgccatac tgtcgcggac cgcctggggg   7380
tgggtgagg  ctgggccct  gatcacagct gcaacttcca ctttgtggga gggctctccg   7440
aacaagtact ggaactcctc cacagccacc tcactgtgta acatttttag ggaagctac   7500
ttggctggag cttctctaat ctacacagta acaagaaacg ctggcttggt caagagacgt   7560
gggggtggaa cggagagac  cctggagag  aaatggaagg cccgcctgaa ccagatgtcg   7620
gccctggagt tctactccta caaaaagtca ggcatcaccg aggtgtgcag agaagaggcc   7680
cgccgcgccc tcaaggacgg tgtggcaacg ggaggcacg  ctgtgtcccg aggaagtgca   7740
aagctgagat ggttggtgga gagggatac  ctgcagccct atggaaaggt cattgatctt   7800
```

-continued

```
ggatgtggca gaggggctg gagttactat gccgccacca tccgcaaagt tcaagaagtg    7860
aaaggataca caaaggagg ccctggtcat gaagaaccca tgttggtgca aagctatggg    7920
tggaacatag tccgtcttaa gagtggggtg gacgtctttc atatggcggc tgagccgtgt   7980
gacacgttgc tgtgtgatat aggtgagtca tcatctagtc ctgaagtgga agaagcacgg   8040
acgctcagag tcctctccat ggtgggggat tggcttgaaa aaagaccagg agccttttgt   8100
ataaaagtgt tgtgcccata caccagcact atgatggaaa ccctggagcg actgcagcgt   8160
aggtatgggg gaggactggt cagagtgcca ctctcccgca actctacaca tgagatgtac   8220
tgggtctctg gagcgaaaag caacaccata aaaagtgtgt ccaccacgag ccagctcctt   8280
ttggggcgca tggacgggcc caggaggcca gtgaaatatg aagaggatgt gaatctcggc   8340
tctggcacgc gggctgtggt aagctgcgct gaagctccca acatgaagat cattggtaac   8400
cgcattgaga ggatccgcag tgagcacgcg gaaacgtggt ctttgacga gaaccaccca    8460
tataggacat gggcttacca tggaagctac gaggccccca cacaagggtc agcgtcctct   8520
ctaataaacg gggttgtcag gctcctgtca aaaccctggg atgtggtgac tggagtcaca   8580
ggaatagcca tgaccgacac cacaccgtat ggtcagcaaa gagttttcaa ggaaaaagtg   8640
gacactaggg tgccagaccc ccaagaaggc actcgtcagg ttatgagcat ggtctcttcc   8700
tggttgtgga aagagttagg caaacacaaa cggccacgag tctgtaccaa gaagagttc    8760
atcaacaagg ttcgtagcaa cgcagcatta ggggcaatat ttgaagagga aaagagtgg    8820
aagactgcag tggaagctgt gaacgatcca aggttctggg ctctagtgga caaggaaaga   8880
gagcaccacc tgagggaga gtgccagagc tgtgtgtaca acatgatggg aaaaagagaa    8940
aagaaacaag gggaatttgg aaaggccaag ggcagccgcg ccatctggta catgtggcta   9000
gggctagat ttctagagtt cgaagccctt ggattcttga cgaggatca ctggatgggg     9060
agagagaatt caggaggtgg tgttgaaggg ctaggattac aaagactcgg atatgtctta   9120
gaagagatga gtcgcatacc aggaggaagg atgtatgcag atgatactgc tggctgggac   9180
acccgcatca gcaggtttga tctggagaat gaagctctaa tcaccaacca aatggagaaa   9240
gggcacaggg ccttggcatt ggccataatc aagtacacat accaaaacaa agtggtaaag   9300
gtccttagac cagctgaaaa agggaagaca gttatggaca ttatttcaag acaagaccaa   9360
agggggagcg gacaagttgt cacttacgct cttaatacat ttaccaacct agtggtgcag   9420
ctcattcgga atatggaggc tgaggaagtt ctagagatgc aagacttgtg gctgctgcgg   9480
aggtcagaga aagtgaccaa ctggttgcag agcaatggat gggataggct caaacgaatg   9540
gcagtcagtg gagatgattg cgttgtgaaa ccaattgatg ataggtttgc acatgctctc   9600
aggttcttga atgatatggg aaaagttagg aaggacacac aagagtggaa gccctcaact   9660
ggatgggaca actgggaaga agttccgttt tgctcccacc acttcaacaa gctccatctc   9720
aaggacggga ggtccattgt ggttccctgc cgccaccaag atgaactgat tggccgagct   9780
cgcgtctcac cggggcggg atggagcatc cgggagactg cttgcctagc aaaatcatat   9840
gcgcaaatgt ggcagctcct ttatttccac agaaaggacc tccgactgat ggccaatgcc   9900
atttgttcat ctgtgccagt tgactgggtt ccaactggga gaactacctg gtcaatccat   9960
ggaaagggag aatggatgac cactgaagac atgcttgtgg tgtggaacag agtgtggatt   10020
gaggagaacg accacatgga agacaagacc ccagttacga aatggacaga cattccctat   10080
ttgggaaaaa gggaagactt gtggtgtggg tctctcatag gcacagacc gcgcaccacc   10140
tgggctgaga acattaaaaa cacagtcaac atgatgcgta ggatcatagg tgatgaagaa   10200
```

```
aagtacgtgg actacctatc cacccaagtt cgctacttgg gcgaagaagg gtccacacct    10260
ggagtgcta                                                             10269
```

<210> SEQ ID NO 8
<211> LENGTH: 3423
<212> TYPE: PRT
<213> ORGANISM: Zika virus

<400> SEQUENCE: 8

```
Met Lys Asn Pro Lys Lys Lys Ser Gly Gly Phe Arg Ile Val Asn Met
1               5                   10                  15

Leu Lys Arg Gly Val Ala Arg Val Ser Pro Phe Gly Gly Leu Lys Arg
            20                  25                  30

Leu Pro Ala Gly Leu Leu Leu Gly His Gly Pro Ile Arg Met Val Leu
        35                  40                  45

Ala Ile Leu Ala Phe Leu Arg Phe Thr Ala Ile Lys Pro Ser Leu Gly
    50                  55                  60

Leu Ile Asn Arg Trp Gly Ser Val Gly Lys Lys Glu Ala Met Glu Ile
65                  70                  75                  80

Ile Lys Lys Phe Lys Lys Asp Leu Ala Ala Met Leu Arg Ile Ile Asn
                85                  90                  95

Ala Arg Lys Glu Lys Lys Arg Arg Gly Thr Asp Thr Ser Val Gly Ile
            100                 105                 110

Val Gly Leu Leu Leu Thr Thr Ala Met Ala Val Glu Val Thr Arg Arg
        115                 120                 125

Gly Asn Ala Tyr Tyr Met Tyr Leu Asp Arg Ser Asp Ala Gly Glu Ala
    130                 135                 140

Ile Ser Phe Pro Thr Thr Met Gly Met Asn Lys Cys Tyr Ile Gln Ile
145                 150                 155                 160

Met Asp Leu Gly His Met Cys Asp Ala Thr Met Ser Tyr Glu Cys Pro
                165                 170                 175

Met Leu Asp Glu Gly Val Glu Pro Asp Asp Val Asp Cys Trp Cys Asn
            180                 185                 190

Thr Thr Ser Thr Trp Val Val Tyr Gly Thr Cys His His Lys Lys Gly
        195                 200                 205

Glu Ala Arg Arg Ser Arg Arg Ala Val Thr Leu Pro Ser His Ser Thr
    210                 215                 220

Arg Lys Leu Gln Thr Arg Ser Gln Thr Trp Leu Glu Ser Arg Glu Tyr
225                 230                 235                 240

Thr Lys His Leu Ile Arg Val Glu Asn Trp Ile Phe Arg Asn Pro Gly
                245                 250                 255

Phe Ala Leu Ala Ala Ala Ala Ile Ala Trp Leu Leu Gly Ser Ser Thr
            260                 265                 270

Ser Gln Lys Val Ile Tyr Leu Val Met Ile Leu Leu Ile Ala Pro Ala
        275                 280                 285

Tyr Ser Ile Arg Cys Ile Gly Val Ser Asn Arg Asp Phe Val Glu Gly
    290                 295                 300

Met Ser Gly Gly Thr Trp Val Asp Val Val Leu Glu His Gly Gly Cys
305                 310                 315                 320

Val Thr Val Met Ala Gln Asp Lys Pro Thr Val Asp Ile Glu Leu Val
                325                 330                 335

Thr Thr Thr Val Ser Asn Met Ala Glu Val Arg Ser Tyr Cys Tyr Glu
            340                 345                 350
```

-continued

```
Ala Ser Ile Ser Asp Met Ala Ser Asp Ser Arg Cys Pro Thr Gln Gly
            355                 360                 365

Glu Ala Tyr Leu Asp Lys Gln Ser Asp Thr Gln Tyr Val Cys Lys Arg
370                 375                 380

Thr Leu Val Asp Arg Gly Trp Gly Asn Gly Cys Gly Leu Phe Gly Lys
385                 390                 395                 400

Gly Ser Leu Val Thr Cys Ala Lys Phe Ala Cys Ser Lys Lys Met Thr
                405                 410                 415

Gly Lys Ser Ile Gln Pro Glu Asn Leu Glu Tyr Arg Ile Met Leu Ser
                420                 425                 430

Val His Gly Ser Gln His Ser Gly Met Ile Val Asn Asp Thr Gly His
            435                 440                 445

Glu Thr Asp Glu Asn Arg Ala Lys Val Glu Ile Thr Pro Asn Ser Pro
450                 455                 460

Arg Ala Glu Ala Thr Leu Gly Gly Phe Gly Ser Leu Gly Leu Asp Cys
465                 470                 475                 480

Glu Pro Arg Thr Gly Leu Asp Phe Ser Asp Leu Tyr Tyr Leu Thr Met
                485                 490                 495

Asn Asn Lys His Trp Leu Val His Lys Glu Trp Phe His Asp Ile Pro
                500                 505                 510

Leu Pro Trp His Ala Gly Ala Asp Thr Gly Thr Pro His Trp Asn Asn
            515                 520                 525

Lys Glu Ala Leu Val Glu Phe Lys Asp Ala His Ala Lys Arg Gln Thr
            530                 535                 540

Val Val Val Leu Gly Ser Gln Glu Gly Ala Val His Thr Ala Leu Ala
545                 550                 555                 560

Gly Ala Leu Glu Ala Glu Met Asp Gly Ala Lys Gly Arg Leu Ser Ser
                565                 570                 575

Gly His Leu Lys Cys Arg Leu Lys Met Asp Lys Leu Arg Leu Lys Gly
            580                 585                 590

Val Ser Tyr Ser Leu Cys Thr Ala Ala Phe Thr Phe Thr Lys Ile Pro
            595                 600                 605

Ala Glu Thr Leu His Gly Thr Val Thr Val Glu Val Gln Tyr Ala Gly
610                 615                 620

Thr Asp Gly Pro Cys Lys Val Pro Ala Gln Met Ala Val Asp Met Gln
625                 630                 635                 640

Thr Leu Thr Pro Val Gly Arg Leu Ile Thr Ala Asn Pro Val Ile Thr
                645                 650                 655

Glu Ser Thr Glu Asn Ser Lys Met Met Leu Glu Leu Asp Pro Pro Phe
                660                 665                 670

Gly Asp Ser Tyr Ile Val Ile Gly Val Gly Glu Lys Lys Ile Thr His
                675                 680                 685

His Trp His Arg Ser Gly Ser Thr Ile Gly Lys Ala Phe Glu Ala Thr
            690                 695                 700

Val Arg Gly Ala Lys Arg Met Ala Val Leu Gly Asp Thr Ala Trp Asp
705                 710                 715                 720

Phe Gly Ser Val Gly Gly Ala Leu Asn Ser Leu Gly Lys Gly Ile His
                725                 730                 735

Gln Ile Phe Gly Ala Ala Phe Lys Ser Leu Phe Gly Gly Met Ser Trp
                740                 745                 750

Phe Ser Gln Ile Leu Ile Gly Thr Leu Leu Val Trp Leu Gly Leu Asn
            755                 760                 765

Thr Lys Asn Gly Ser Ile Ser Leu Met Cys Leu Ala Leu Gly Gly Val
```

```
                770             775             780
Leu Ile Phe Leu Ser Thr Ala Val Ser Ala Asp Val Gly Cys Ser Val
785             790             795             800

Asp Phe Ser Lys Lys Glu Thr Arg Cys Gly Thr Gly Val Phe Val Tyr
            805             810             815

Asn Asp Val Glu Ala Trp Arg Asp Arg Tyr Lys Tyr His Pro Asp Ser
            820             825             830

Pro Arg Arg Leu Ala Ala Ala Val Lys Gln Ala Trp Glu Asp Gly Ile
            835             840             845

Cys Gly Ile Ser Ser Val Ser Arg Met Glu Asn Ile Met Trp Arg Ser
            850             855             860

Val Glu Gly Glu Leu Asn Ala Ile Leu Glu Glu Asn Gly Val Gln Leu
865             870             875             880

Thr Val Val Val Gly Ser Val Lys Asn Pro Met Trp Arg Gly Pro Gln
            885             890             895

Arg Leu Pro Val Pro Val Asn Glu Leu Pro His Gly Trp Lys Ala Trp
            900             905             910

Gly Lys Ser Tyr Phe Val Arg Ala Ala Lys Thr Asn Asn Ser Phe Val
            915             920             925

Val Asp Gly Asp Thr Leu Lys Glu Cys Pro Leu Lys His Arg Ala Trp
            930             935             940

Asn Ser Phe Leu Val Glu Asp His Gly Phe Gly Val Phe His Thr Ser
945             950             955             960

Val Trp Leu Lys Val Arg Glu Asp Tyr Ser Leu Glu Cys Asp Pro Ala
            965             970             975

Val Ile Gly Thr Ala Ala Lys Gly Lys Glu Ala Val His Ser Asp Leu
            980             985             990

Gly Tyr Trp Ile Glu Ser Glu Lys Asn Asp Thr Trp Arg Leu Lys Arg
            995             1000            1005

Ala His Leu Ile Glu Met Lys Thr Cys Glu Trp Pro Lys Ser His
    1010            1015            1020

Thr Leu Trp Thr Asp Gly Ile Glu Glu Ser Asp Leu Ile Ile Pro
    1025            1030            1035

Lys Ser Leu Ala Gly Pro Leu Ser His His Asn Thr Arg Glu Gly
    1040            1045            1050

Tyr Arg Thr Gln Met Lys Gly Pro Trp His Ser Glu Glu Leu Glu
    1055            1060            1065

Ile Arg Phe Glu Glu Cys Pro Gly Thr Lys Val His Val Glu Glu
    1070            1075            1080

Thr Cys Gly Thr Arg Gly Pro Ser Leu Arg Ser Thr Thr Ala Ser
    1085            1090            1095

Gly Arg Val Ile Glu Glu Trp Cys Cys Arg Glu Cys Thr Met Pro
    1100            1105            1110

Pro Leu Ser Phe Arg Ala Lys Asp Gly Cys Trp Tyr Gly Met Glu
    1115            1120            1125

Ile Arg Pro Arg Lys Glu Pro Glu Ser Asn Leu Val Arg Ser Met
    1130            1135            1140

Val Thr Ala Gly Ser Thr Asp His Met Asp His Phe Ser Leu Gly
    1145            1150            1155

Val Leu Val Ile Leu Leu Met Val Gln Glu Gly Leu Lys Lys Arg
    1160            1165            1170

Met Thr Thr Lys Ile Ile Ile Ser Thr Ser Met Ala Val Leu Val
    1175            1180            1185
```

```
Ala Met Ile Leu Gly Gly Phe Ser Met Ser Asp Leu Ala Lys Leu
    1190            1195            1200

Ala Ile Leu Met Gly Ala Thr Phe Ala Glu Met Asn Thr Gly Gly
    1205            1210            1215

Asp Val Ala His Leu Ala Leu Ile Ala Ala Phe Lys Val Arg Pro
    1220            1225            1230

Ala Leu Leu Val Ser Phe Ile Phe Arg Ala Asn Trp Thr Pro Arg
    1235            1240            1245

Glu Ser Met Leu Leu Ala Leu Ala Ser Cys Leu Leu Gln Thr Ala
    1250            1255            1260

Ile Ser Ala Leu Glu Gly Asp Leu Met Val Pro Ile Asn Gly Phe
    1265            1270            1275

Ala Leu Ala Trp Leu Ala Ile Arg Ala Met Val Val Pro Arg Thr
    1280            1285            1290

Asp Asn Ile Thr Leu Ala Ile Leu Ala Ala Leu Thr Pro Leu Ala
    1295            1300            1305

Arg Gly Thr Leu Leu Val Ala Trp Arg Ala Gly Leu Ala Thr Cys
    1310            1315            1320

Gly Gly Phe Met Leu Leu Ser Leu Lys Gly Lys Gly Ser Val Lys
    1325            1330            1335

Lys Asn Leu Pro Phe Val Met Ala Leu Gly Leu Thr Ala Val Arg
    1340            1345            1350

Leu Val Asp Pro Ile Asn Val Val Gly Leu Leu Leu Thr Arg
    1355            1360            1365

Ser Gly Lys Arg Ser Trp Pro Pro Ser Glu Val Leu Thr Ala Val
    1370            1375            1380

Gly Leu Ile Cys Ala Leu Ala Gly Gly Phe Ala Lys Ala Asp Ile
    1385            1390            1395

Glu Met Ala Gly Pro Met Ala Ala Val Gly Leu Leu Ile Val Ser
    1400            1405            1410

Tyr Val Val Ser Gly Lys Ser Val Asp Met Tyr Ile Glu Arg Ala
    1415            1420            1425

Gly Asp Ile Thr Trp Glu Lys Asp Ala Glu Val Thr Gly Asn Ser
    1430            1435            1440

Pro Arg Leu Asp Val Ala Leu Asp Glu Ser Gly Asp Phe Ser Leu
    1445            1450            1455

Val Glu Asp Asp Gly Pro Pro Met Arg Glu Ile Ile Leu Lys Val
    1460            1465            1470

Val Leu Met Ala Ile Cys Gly Met Asn Pro Ile Ala Ile Pro Phe
    1475            1480            1485

Ala Ala Gly Ala Trp Tyr Val Tyr Val Lys Thr Gly Lys Arg Ser
    1490            1495            1500

Gly Ala Leu Trp Asp Val Pro Ala Pro Lys Glu Val Lys Lys Gly
    1505            1510            1515

Glu Thr Thr Asp Gly Val Tyr Arg Val Met Thr Arg Arg Leu Leu
    1520            1525            1530

Gly Ser Thr Gln Val Gly Val Gly Val Met Gln Glu Gly Val Phe
    1535            1540            1545

His Thr Met Trp His Val Thr Lys Gly Ser Ala Leu Arg Ser Gly
    1550            1555            1560

Glu Gly Arg Leu Asp Pro Tyr Trp Gly Asp Val Lys Gln Asp Leu
    1565            1570            1575
```

```
Val Ser Tyr Cys Gly Pro Trp Lys Leu Asp Ala Ala Trp Asp Gly
    1580                1585                1590

His Ser Glu Val Gln Leu Leu Ala Val Pro Pro Gly Glu Arg Ala
    1595                1600                1605

Arg Asn Ile Gln Thr Leu Pro Gly Ile Phe Lys Thr Lys Asp Gly
    1610                1615                1620

Asp Ile Gly Ala Val Ala Leu Asp Tyr Pro Ala Gly Thr Ser Gly
    1625                1630                1635

Ser Pro Ile Leu Asp Lys Cys Gly Arg Val Ile Gly Leu Tyr Gly
    1640                1645                1650

Asn Gly Val Val Ile Lys Asn Gly Ser Tyr Val Ser Ala Ile Thr
    1655                1660                1665

Gln Gly Arg Arg Glu Glu Glu Thr Pro Val Glu Cys Phe Glu Pro
    1670                1675                1680

Ser Met Leu Lys Lys Lys Gln Leu Thr Val Leu Asp Leu His Pro
    1685                1690                1695

Gly Ala Gly Lys Thr Arg Arg Val Leu Pro Glu Ile Val Arg Glu
    1700                1705                1710

Ala Ile Lys Thr Arg Leu Arg Thr Val Ile Leu Ala Pro Thr Arg
    1715                1720                1725

Val Val Ala Ala Glu Met Glu Glu Ala Leu Arg Gly Leu Pro Val
    1730                1735                1740

Arg Tyr Met Thr Thr Ala Val Asn Val Thr His Ser Gly Thr Glu
    1745                1750                1755

Ile Val Asp Leu Met Cys His Ala Thr Phe Thr Ser Arg Leu Leu
    1760                1765                1770

Gln Pro Ile Arg Val Pro Asn Tyr Asn Leu Tyr Ile Met Asp Glu
    1775                1780                1785

Ala His Phe Thr Asp Pro Ser Ser Ile Ala Ala Arg Gly Tyr Ile
    1790                1795                1800

Ser Thr Arg Val Glu Met Gly Glu Ala Ala Ala Ile Phe Met Thr
    1805                1810                1815

Ala Thr Pro Pro Gly Thr Arg Asp Ala Phe Pro Asp Ser Asn Ser
    1820                1825                1830

Pro Ile Met Asp Thr Glu Val Glu Val Pro Glu Arg Ala Trp Ser
    1835                1840                1845

Ser Gly Phe Asp Trp Val Thr Asp His Ser Gly Lys Thr Val Trp
    1850                1855                1860

Phe Val Pro Ser Val Arg Asn Gly Asn Glu Ile Ala Ala Cys Leu
    1865                1870                1875

Thr Lys Ala Gly Lys Arg Val Ile Gln Leu Ser Arg Lys Thr Phe
    1880                1885                1890

Glu Thr Glu Phe Gln Lys Thr Lys His Gln Glu Trp Asp Phe Val
    1895                1900                1905

Val Thr Thr Asp Ile Ser Glu Met Gly Ala Asn Phe Lys Ala Asp
    1910                1915                1920

Arg Val Ile Asp Ser Arg Arg Cys Leu Lys Pro Val Ile Leu Asp
    1925                1930                1935

Gly Glu Arg Val Ile Leu Ala Gly Pro Met Pro Val Thr His Ala
    1940                1945                1950

Ser Ala Ala Gln Arg Arg Gly Arg Ile Gly Arg Asn Pro Asn Lys
    1955                1960                1965

Pro Gly Asp Glu Tyr Leu Tyr Gly Gly Gly Cys Ala Glu Thr Asp
```

```
               1970                1975                1980
Glu  Asp  His  Ala  His  Trp  Leu  Glu  Ala  Arg  Met  Leu  Leu  Asp  Asn
               1985                1990                1995

Ile  Tyr  Leu  Gln  Asp  Gly  Leu  Ile  Ala  Ser  Leu  Tyr  Arg  Pro  Glu
               2000                2005                2010

Ala  Asp  Lys  Val  Ala  Ala  Ile  Glu  Gly  Glu  Phe  Lys  Leu  Arg  Thr
               2015                2020                2025

Glu  Gln  Arg  Lys  Thr  Phe  Val  Glu  Leu  Met  Lys  Arg  Gly  Asp  Leu
               2030                2035                2040

Pro  Val  Trp  Leu  Ala  Tyr  Gln  Val  Ala  Ser  Ala  Gly  Ile  Thr  Tyr
               2045                2050                2055

Thr  Asp  Arg  Arg  Trp  Cys  Phe  Asp  Gly  Thr  Thr  Asn  Asn  Thr  Ile
               2060                2065                2070

Met  Glu  Asp  Ser  Val  Pro  Ala  Glu  Val  Trp  Thr  Arg  Tyr  Gly  Glu
               2075                2080                2085

Lys  Arg  Val  Leu  Lys  Pro  Arg  Trp  Met  Asp  Ala  Arg  Val  Cys  Ser
               2090                2095                2100

Asp  His  Ala  Ala  Leu  Lys  Ser  Phe  Lys  Glu  Phe  Ala  Ala  Gly  Lys
               2105                2110                2115

Arg  Gly  Ala  Ala  Phe  Gly  Val  Met  Glu  Ala  Leu  Gly  Thr  Leu  Pro
               2120                2125                2130

Gly  His  Met  Thr  Glu  Arg  Phe  Gln  Glu  Ala  Ile  Asp  Asn  Leu  Ala
               2135                2140                2145

Val  Leu  Met  Arg  Ala  Glu  Thr  Gly  Ser  Arg  Pro  Tyr  Lys  Ala  Ala
               2150                2155                2160

Ala  Ala  Gln  Leu  Pro  Glu  Thr  Leu  Glu  Thr  Ile  Met  Leu  Leu  Gly
               2165                2170                2175

Leu  Leu  Gly  Thr  Val  Ser  Leu  Gly  Ile  Phe  Phe  Val  Leu  Met  Arg
               2180                2185                2190

Asn  Lys  Gly  Ile  Gly  Lys  Met  Gly  Phe  Gly  Met  Val  Thr  Leu  Gly
               2195                2200                2205

Ala  Ser  Ala  Trp  Leu  Met  Trp  Leu  Ser  Glu  Ile  Glu  Pro  Ala  Arg
               2210                2215                2220

Ile  Ala  Cys  Val  Leu  Ile  Val  Val  Phe  Leu  Leu  Leu  Val  Val  Leu
               2225                2230                2235

Ile  Pro  Glu  Pro  Glu  Lys  Gln  Arg  Ser  Pro  Gln  Asp  Asn  Gln  Met
               2240                2245                2250

Ala  Ile  Ile  Ile  Met  Val  Ala  Val  Gly  Leu  Leu  Gly  Leu  Ile  Thr
               2255                2260                2265

Ala  Asn  Glu  Leu  Gly  Trp  Leu  Glu  Arg  Thr  Lys  Ser  Asp  Leu  Ser
               2270                2275                2280

His  Leu  Met  Gly  Arg  Arg  Glu  Glu  Gly  Ala  Thr  Ile  Gly  Phe  Ser
               2285                2290                2295

Met  Asp  Ile  Asp  Leu  Arg  Pro  Ala  Ser  Ala  Trp  Ala  Ile  Tyr  Ala
               2300                2305                2310

Ala  Leu  Thr  Thr  Phe  Ile  Thr  Pro  Ala  Val  Gln  His  Ala  Val  Thr
               2315                2320                2325

Thr  Ser  Tyr  Asn  Asn  Tyr  Ser  Leu  Met  Ala  Met  Ala  Thr  Gln  Ala
               2330                2335                2340

Gly  Val  Leu  Phe  Gly  Met  Gly  Lys  Gly  Met  Pro  Phe  Tyr  Ala  Trp
               2345                2350                2355

Asp  Phe  Gly  Val  Pro  Leu  Leu  Met  Ile  Gly  Cys  Tyr  Ser  Gln  Leu
               2360                2365                2370
```

```
Thr Pro Leu Thr Leu Ile Val Ala Ile Ile Leu Leu Val Ala His
    2375            2380            2385

Tyr Met Tyr Leu Ile Pro Gly Leu Gln Ala Ala Ala Arg Ala
    2390            2395            2400

Ala Gln Lys Arg Thr Ala Ala Gly Ile Met Lys Asn Pro Val Val
    2405            2410            2415

Asp Gly Ile Val Val Thr Asp Ile Asp Thr Met Thr Ile Asp Pro
    2420            2425            2430

Gln Val Glu Lys Lys Met Gly Gln Val Leu Leu Ile Ala Val Ala
    2435            2440            2445

Val Ser Ser Ala Ile Leu Ser Arg Thr Ala Trp Gly Trp Gly Glu
    2450            2455            2460

Ala Gly Ala Leu Ile Thr Ala Ala Thr Ser Thr Leu Trp Glu Gly
    2465            2470            2475

Ser Pro Asn Lys Tyr Trp Asn Ser Ser Thr Ala Thr Ser Leu Cys
    2480            2485            2490

Asn Ile Phe Arg Gly Ser Tyr Leu Ala Gly Ala Ser Leu Ile Tyr
    2495            2500            2505

Thr Val Thr Arg Asn Ala Gly Leu Val Lys Arg Arg Gly Gly Gly
    2510            2515            2520

Thr Gly Glu Thr Leu Gly Glu Lys Trp Lys Ala Arg Leu Asn Gln
    2525            2530            2535

Met Ser Ala Leu Glu Phe Tyr Ser Tyr Lys Lys Ser Gly Ile Thr
    2540            2545            2550

Glu Val Cys Arg Glu Glu Ala Arg Arg Ala Leu Lys Asp Gly Val
    2555            2560            2565

Ala Thr Gly Gly His Ala Val Ser Arg Gly Ser Ala Lys Leu Arg
    2570            2575            2580

Trp Leu Val Glu Arg Gly Tyr Leu Gln Pro Tyr Gly Lys Val Ile
    2585            2590            2595

Asp Leu Gly Cys Gly Arg Gly Gly Trp Ser Tyr Tyr Ala Ala Thr
    2600            2605            2610

Ile Arg Lys Val Gln Glu Val Lys Gly Tyr Thr Lys Gly Gly Pro
    2615            2620            2625

Gly His Glu Glu Pro Met Leu Val Gln Ser Tyr Gly Trp Asn Ile
    2630            2635            2640

Val Arg Leu Lys Ser Gly Val Asp Val Phe His Met Ala Ala Glu
    2645            2650            2655

Pro Cys Asp Thr Leu Leu Cys Asp Ile Gly Glu Ser Ser Ser Ser
    2660            2665            2670

Pro Glu Val Glu Glu Ala Arg Thr Leu Arg Val Leu Ser Met Val
    2675            2680            2685

Gly Asp Trp Leu Glu Lys Arg Pro Gly Ala Phe Cys Ile Lys Val
    2690            2695            2700

Leu Cys Pro Tyr Thr Ser Thr Met Met Glu Thr Leu Glu Arg Leu
    2705            2710            2715

Gln Arg Arg Tyr Gly Gly Gly Leu Val Arg Val Pro Leu Ser Arg
    2720            2725            2730

Asn Ser Thr His Glu Met Tyr Trp Val Ser Gly Ala Lys Ser Asn
    2735            2740            2745

Thr Ile Lys Ser Val Ser Thr Thr Ser Gln Leu Leu Leu Gly Arg
    2750            2755            2760
```

```
Met Asp Gly Pro Arg Arg Pro Val Lys Tyr Glu Glu Asp Val Asn
2765                2770                2775

Leu Gly Ser Gly Thr Arg Ala Val Val Ser Cys Ala Glu Ala Pro
2780                2785                2790

Asn Met Lys Ile Ile Gly Asn Arg Ile Glu Arg Ile Arg Ser Glu
2795                2800                2805

His Ala Glu Thr Trp Phe Phe Asp Glu Asn His Pro Tyr Arg Thr
2810                2815                2820

Trp Ala Tyr His Gly Ser Tyr Glu Ala Pro Thr Gln Gly Ser Ala
2825                2830                2835

Ser Ser Leu Ile Asn Gly Val Val Arg Leu Leu Ser Lys Pro Trp
2840                2845                2850

Asp Val Val Thr Gly Val Thr Gly Ile Ala Met Thr Asp Thr Thr
2855                2860                2865

Pro Tyr Gly Gln Gln Arg Val Phe Lys Glu Lys Val Asp Thr Arg
2870                2875                2880

Val Pro Asp Pro Gln Glu Gly Thr Arg Gln Val Met Ser Met Val
2885                2890                2895

Ser Ser Trp Leu Trp Lys Glu Leu Gly Lys His Lys Arg Pro Arg
2900                2905                2910

Val Cys Thr Lys Glu Glu Phe Ile Asn Lys Val Arg Ser Asn Ala
2915                2920                2925

Ala Leu Gly Ala Ile Phe Glu Glu Lys Glu Trp Lys Thr Ala
2930                2935                2940

Val Glu Ala Val Asn Asp Pro Arg Phe Trp Ala Leu Val Asp Lys
2945                2950                2955

Glu Arg Glu His His Leu Arg Gly Glu Cys Gln Ser Cys Val Tyr
2960                2965                2970

Asn Met Met Gly Lys Arg Glu Lys Lys Gln Gly Glu Phe Gly Lys
2975                2980                2985

Ala Lys Gly Ser Arg Ala Ile Trp Tyr Met Trp Leu Gly Ala Arg
2990                2995                3000

Phe Leu Glu Phe Glu Ala Leu Gly Phe Leu Asn Glu Asp His Trp
3005                3010                3015

Met Gly Arg Glu Asn Ser Gly Gly Gly Val Glu Gly Leu Gly Leu
3020                3025                3030

Gln Arg Leu Gly Tyr Val Leu Glu Glu Met Ser Arg Ile Pro Gly
3035                3040                3045

Gly Arg Met Tyr Ala Asp Asp Thr Ala Gly Trp Asp Thr Arg Ile
3050                3055                3060

Ser Arg Phe Asp Leu Glu Asn Glu Ala Leu Ile Thr Asn Gln Met
3065                3070                3075

Glu Lys Gly His Arg Ala Leu Ala Leu Ala Ile Ile Lys Tyr Thr
3080                3085                3090

Tyr Gln Asn Lys Val Val Lys Val Leu Arg Pro Ala Glu Lys Gly
3095                3100                3105

Lys Thr Val Met Asp Ile Ile Ser Arg Gln Asp Gln Arg Gly Ser
3110                3115                3120

Gly Gln Val Val Thr Tyr Ala Leu Asn Thr Phe Thr Asn Leu Val
3125                3130                3135

Val Gln Leu Ile Arg Asn Met Glu Ala Glu Glu Val Leu Glu Met
3140                3145                3150

Gln Asp Leu Trp Leu Leu Arg Arg Ser Glu Lys Val Thr Asn Trp
```

-continued

```
                3155                    3160                    3165
Leu Gln Ser Asn Gly Trp Asp Arg Leu Lys Arg Met Ala Val Ser
            3170                    3175                3180

Gly Asp Asp Cys Val Val Lys Pro Ile Asp Asp Arg Phe Ala His
            3185                    3190                3195

Ala Leu Arg Phe Leu Asn Asp Met Gly Lys Val Arg Lys Asp Thr
            3200                    3205                3210

Gln Glu Trp Lys Pro Ser Thr Gly Trp Asp Asn Trp Glu Glu Val
            3215                    3220                3225

Pro Phe Cys Ser His His Phe Asn Lys Leu His Leu Lys Asp Gly
            3230                    3235                3240

Arg Ser Ile Val Val Pro Cys Arg His Gln Asp Glu Leu Ile Gly
            3245                    3250                3255

Arg Ala Arg Val Ser Pro Gly Ala Gly Trp Ser Ile Arg Glu Thr
            3260                    3265                3270

Ala Cys Leu Ala Lys Ser Tyr Ala Gln Met Trp Gln Leu Leu Tyr
            3275                    3280                3285

Phe His Arg Arg Asp Leu Arg Leu Met Ala Asn Ala Ile Cys Ser
            3290                    3295                3300

Ser Val Pro Val Asp Trp Val Pro Thr Gly Arg Thr Thr Trp Ser
            3305                    3310                3315

Ile His Gly Lys Gly Glu Trp Met Thr Thr Glu Asp Met Leu Val
            3320                    3325                3330

Val Trp Asn Arg Val Trp Ile Glu Glu Asn Asp His Met Glu Asp
            3335                    3340                3345

Lys Thr Pro Val Thr Lys Trp Thr Asp Ile Pro Tyr Leu Gly Lys
            3350                    3355                3360

Arg Glu Asp Leu Trp Cys Gly Ser Leu Ile Gly His Arg Pro Arg
            3365                    3370                3375

Thr Thr Trp Ala Glu Asn Ile Lys Asn Thr Val Asn Met Met Arg
            3380                    3385                3390

Arg Ile Ile Gly Asp Glu Glu Lys Tyr Val Asp Tyr Leu Ser Thr
            3395                    3400                3405

Gln Val Arg Tyr Leu Gly Glu Glu Gly Ser Thr Pro Gly Val Leu
            3410                    3415                3420
```